US010604750B2

(12) United States Patent
Greenfield et al.

(10) Patent No.: US 10,604,750 B2
(45) Date of Patent: Mar. 31, 2020

(54) ACETYL-COA CARBOXYLASE VARIANTS

(71) Applicant: REG Life Sciences, LLC, Ames, IA (US)

(72) Inventors: Derek L. Greenfield, South San Francisco, CA (US); Donald E. Trimbur, South San Francisco, CA (US); Andreas W. Schirmer, South San Francisco, CA (US); Cindy Chang, South San Francisco, CA (US); Behnaz Behrouzian, South San Francisco, CA (US); Jessica Winger, South San Francisco, CA (US)

(73) Assignee: GENOMATICA, INC., San Diego, CA (US)

( * ) Notice: Subject to any disclaimer, the term of this patent is extended or adjusted under 35 U.S.C. 154(b) by 0 days.

(21) Appl. No.: 15/021,515

(22) PCT Filed: Sep. 12, 2014

(86) PCT No.: PCT/US2014/055510
§ 371 (c)(1),
(2) Date: Mar. 11, 2016

(87) PCT Pub. No.: WO2015/038970
PCT Pub. Date: Mar. 19, 2015

(65) Prior Publication Data
US 2016/0230164 A1    Aug. 11, 2016

Related U.S. Application Data

(60) Provisional application No. 61/877,418, filed on Sep. 13, 2013, provisional application No. 61/892,242, filed on Oct. 17, 2013.

(51) Int. Cl.
*C07K 14/245* (2006.01)
*C12N 9/00* (2006.01)
*C12P 7/64* (2006.01)

(52) U.S. Cl.
CPC .............. *C12N 9/93* (2013.01); *C07K 14/245* (2013.01); *C12P 7/649* (2013.01); *C12Y 604/01002* (2013.01)

(58) Field of Classification Search
None
See application file for complete search history.

(56) References Cited

U.S. PATENT DOCUMENTS

| | | | |
|---|---|---|---|
| 417,721 A | 10/1889 | Haberkorn | |
| 5,965,408 A | 10/1999 | Short | |
| 7,169,588 B2 | 1/2007 | Burch et al. | |
| 8,097,439 B2 | 1/2012 | Alibhai et al. | |
| 8,110,093 B2 | 2/2012 | Friedman et al. | |
| 8,110,670 B2 | 2/2012 | Hu et al. | |
| 8,183,028 B2 | 5/2012 | Alibhai et al. | |
| 8,268,599 B2 | 9/2012 | Schirmer et al. | |
| 8,283,143 B2 | 10/2012 | Hu et al. | |
| 8,313,934 B2 | 11/2012 | Bhatia et al. | |
| 8,323,924 B2 | 12/2012 | Schirmer et al. | |
| 8,372,610 B2 | 2/2013 | Lee et al. | |
| 8,530,221 B2 | 9/2013 | Hu et al. | |
| 8,535,916 B2 | 9/2013 | Del Cardayre et al. | |
| 8,597,922 B2 | 12/2013 | Alibhai et al. | |
| 8,658,404 B2 | 2/2014 | Schirmer et al. | |
| 2003/0110533 A1 | 6/2003 | Cahoon et al. | |
| 2003/0143685 A1* | 7/2003 | Hu | C07K 14/315 435/69.1 |
| 2010/0105963 A1 | 4/2010 | Hu | |
| 2010/0298612 A1 | 11/2010 | Behrouzian et al. | |
| 2011/0165637 A1* | 7/2011 | Pfleger | C12N 9/16 435/134 |
| 2011/0256599 A1* | 10/2011 | Hu | C10L 1/02 435/157 |

OTHER PUBLICATIONS

Guzman et al., Tight Regulation, Modulation, and High-Level Expression by Vectors Containing the Arabinose PBAD Promoter, J. Biol. Chem., 1995, 177, 4121-30.*
Choi-Rhee et al., The Biotin Carboxylase-Biotin Carboxyl Carrier Protein Complex of *Escherichia coli* Acetyl-CoA Carboxylase, J. Biol. Chem., 2003, 278, 30806-12.*
Hugler et al., Characterization of acetyl-CoA/propionyl-CoA carboxylase in Metallosphaera sedula, Eur. J. Biochem., 2003, 270, 736-44.*
GenBank, Accession No. Q8J2Z3, 2011, www.uniprot.org.*
Guo et al., Protein tolerance to random amino acid change, Proc. Natl. Acad. Sci. USA, 2004, 101, 9205-10.*
GenBank, Accession No. NP_417721.1, 2012, www.ncbi.nlm.nih.gov.*
Abdel-Hamid et al., "Coordinate Expression of the Acetyl Coenzyme A Carboxylase Genes, accB and accC, Is Necessary for Normal Regulation of Biotin Synthesis in *Escherichia coli*," Journal of Bacteriology, vol. 189, No. 2, Jan. 15, 2007, pp. 369-376.
Altschul et al. "Basic Local Alignment Search Tool," (1990) J. Mol. Biol. 215(3):403-410.
Altschul et al. "Protein Database Searches Using Compositionally Adjusted Substitution Matrices," (2005) FEBS J. 272(20):5101-5109.
Arkin et al., "An algorithm for protein engineering: Simulations of recursive ensemble mutagenesis," Proc. Natl. Acad. Sci. U.S.A., vol. 89, pp. 7811-7815 (1992).
Arnold, "Protein engineering for unusual environments," Curr. Opin. Biotech. 4: 450-455 (1993).
Barrick et al., "Quantitative Analysis of ribosome binding sites in *E. coli*," Nucleic Acids Res. 22(7): 1287-1295 (1994).

(Continued)

*Primary Examiner* — Robert B Mondesi
*Assistant Examiner* — Todd M Epstein
(74) *Attorney, Agent, or Firm* — Foley & Lardner LLP

(57) ABSTRACT

The disclosure relates to acetyl-CoA carboxylase (ACC) variants and host cells expressing them for the production of malonyl-CoA derived compounds including fatty acid derivatives. Further contemplated are methods of producing increased amounts of malonyl-CoA derived compounds and related cell cultures.

13 Claims, 5 Drawing Sheets

Specification includes a Sequence Listing.

(56) References Cited

OTHER PUBLICATIONS

Braun, "Minireviews—FhuA (TonA), the Career of a Protein," J. Bacteriol. 191(11): 3431-3436 (2009).
Broussard et al., "The Three-Dimensional Structure of the Biotin Carboxylase-Biotin Carboxyl Carrier Protein Complex of *E. coli* Acetyl-CoA Carboxylase," Structure, vol. 21, No. 4, Apr. 1, 2013, pp. 650-657.
Chapman-Smith et al., "Molecular Recognitionin a Post-translational Modification of Exceptional specificity: Mutants of the Biotinylated Domain of Acetyl-CoA Carboxylase Defective in Recognition by Biotin Protein Ligase," Journal of Biological Chemistry, vol. 274, No. 3, Jan. 15, 1999, pp. 1449-1457.
Clark, "Regulation of Fatty Acid Degration in *Escherichia coli*: Analysis by Operon Fusion," J Bacteriol. 148(2): 521-526 (1981).
Communication issued on EP Application 14781729.0, dated Mar. 24, 2016.
Cronan et al., "Multi-subunit acetyl-CoA carboxylases," Progress in Lipid Research, vol. 41, No. 5, Sep. 1, 2002, pp. 407-435.
Currie, "Source Apportionment of Atmospheric Particles", Characterization of Environmental Particles, J. Buffle and H.P. van Leeuwen, Eds., Vol. I of the IUPAC Environmental Analytical Chemistry Series, Lewis Publishers, Inc., pp. 3-74 (1992).
Datsenko et al., "One-step Inactivation of Chromosomal Genes in *Escherichia coli* K-12 using PCR Products," Proc. Natl. Acad. Sci. U.S.A., 97(12): 6640-6645 (2000).
Davis et al., "Inhibition of *Escherichia coli* Acetyl Coenzyme a Carboxylase by Acyl-Acyl Carrier Protein," (2001) Journal of Bacteriology 183(4):1499-1503.
Delegrave et al., "Searching Sequence Space to Engineer Proteins: Exponential Ensemble Mutagenesis," Biotech. Res, 11: 1548-1552 (1993).
Ecker, et al., "Chemical synthesis and expression of a cassette adapted ubiquitin gene," J. Biol. Chem. 262(8):3524-3527 (1987).
Gentz et al., "Promoters recognized by *Escherichia coli* RNA polymerase selected by function: highly efficient promoters from bacteriophage T5," Journal of Bacteriology, vol. 164, No. 1, Oct. 1985, pp. 70-77.
Grosjean et al., "Preferential codon usage in prokaryotic genes: the optimal codon-anticodon interaction energy and the selective codon usage in efficiently expressed genes," Gene 18:199-209 (1982).
International Search Report on PCT/US2014/055510, dated Jun. 10, 2015.
James et al., "Expression of Two *Escherichia coli* Acetyl-CoA Carboxylase Subunits is Autoregulated," The Journal of Biological Chemistry, vol. 279, No. 4, Jan. 23, 2004, pp. 2520-2527.
Kegler-Ebo et al., "Codon cassette mutagenesis: a general method to insert or replace individual codons by using universal mutagenic cassettes," Nucleic Acids Res. 22(9): 1593-1599 (1994).
Maniatis et al., "Regulation of Inducible and Tissue-Specific Gene Expression," Science 236: 1237-1245 (1987).
Marrakchi, et al., "Mechanistic Diversity and Regulation of Type II Fatty Acid Synthesis," Biochem. Soc. Trans. 30(6): 1050-1055 (2002).
Needleman and Wunsch, J. Mol. Biol., 48: 444-453 (1970).
Richards et al., "Cassette mutagenesis shows its strength," Nature 323: 187 (1986).
Rosenberg, "Multiple Sequence Alignment Accuracy and Evolutionary Distance Estimation," BMC Bioinformatics 6: 278 (2005).
Stemmer, "DNA shuffling by random fragmentation and reassembly: in vitro recombination for molecular evolution," Proc. Natl. Acad. Sci. USA. 91: 10747-10751 (1994).
Wilson et al., "Increased Protein Expression Through Improved Ribosome-Binding Sites Obtained by Library Mutagenesis," Biotechniques 17(5):944-953 (1994).
Notice of Reasons for Rejection issued on Japanese Application 2016-542833, dated Oct. 23, 2017.
Jeon, et al., "Development of *Escherichia coli* MG1655 strains to produce long chain fatty acids by engineering fatty acid synthesis (FAS) metabolism," Enzyme Microb Technol., Jun. 10, 2011, vol. 49, No. 1, pp. 44-51.
Park, Sy et al. "An analysis of the concentration change of intermediate metabolites by gene manipulation in fatty acid biosynthesis." Enzyme Microb Technol, Jul. 15, 2012, vol. 51, No. 2, pp. 95-99.
Preliminary Office Action in BR Patent Application No. 1120160068599 dated Oct. 23, 2019 (with English translation) (7 pages).
Davis, et al., Overproduction of Acetyl-CoA Carboxylase Activity Increases the Rate of Fatty Acid Biosynthesis in *Escherichia coli*,: Journal of Biological Chemistry, Sep. 15, 2000, vol. 275, No. 37, pp. 28593-28598.
Notice of Reasons for Rejection in JP Patent Application No. 2019-027399 dated Feb. 5, 2020 (with English translation) (11 pages).

\* cited by examiner

| | | |
|---|---|---|
| Escherichia coli | 106 | GQKVNVGDTLCIVEAMKVMNQIEADKSGTV |
| Lactobacillus brevis | 89 | GDHVEKGDVVCVVEAMKMINEVKSDLTGTL |
| Stenotrophomonas maltophilia | 109 | GQQVKEGETLAIIEAMKMFNPIEADTSGTI |
| Pseudomonas putida | 103 | GQSVKKGDTLCIVEAMKVMNHIEADIGGVI |
| Bacillus subtilis | 107 | GSKVNENTVVCIVEAMKIFNEIEAEVKGEI |
| Corynebacterium glutamicum | 541 | GAEVNEGDTVVLEAMKVENPVKAHKSGTV |
| Saccharomyces cerevisiae | 719 | GEHIIKGQPYAEIEVMKMQMPLVSQENGIV |

Figure 2

ACETYL-CoA CARBOXYLASE VARIANTS

CROSS-REFERENCE TO RELATED APPLICATIONS

This application is a U.S. National Stage under 35 U.S.C. § 371 of International Application Serial No. PCT/US2014/055510, filed Sep. 12, 2014, which claims the benefit of U.S. Provisional Application No. 61/877,418, filed Sep. 13, 2013, and U.S. Provisional Application No. 61/892,242, filed Oct. 17, 2013, the entire disclosures of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Sep. 12, 2014, is named LS00050PCT_SL.txt and is 128,259 bytes in size.

FIELD

The disclosure relates to acetyl-CoA carboxylase (ACC) variants for production of a malonyl-CoA derived compound including a fatty acid derivative. Further contemplated are host cells that express the ACC variants and related cell cultures. Still encompassed are methods of producing malonyl-CoA derived compounds by employing the host cells expressing the ACC variants.

BACKGROUND

Petroleum is a limited, natural resource found in the earth in liquid, gaseous, or solid forms. However, petroleum products are developed at considerable costs, both financial and environmental. In its natural form, crude petroleum extracted from the Earth has few commercial uses. It is a mixture of hydrocarbons, e.g., paraffins (or alkanes), olefins (or alkenes), alkynes, napthenes (or cylcoalkanes), aliphatic compounds, aromatic compounds, etc. of varying length and complexity. In addition, crude petroleum contains other organic compounds (e.g., organic compounds containing nitrogen, oxygen, sulfur, etc.) and impurities (e.g., sulfur, salt, acid, metals, etc.). Due to its high energy density and its easy transportability, most petroleum is refined into fuels, such as transportation fuels (e.g., gasoline, diesel, aviation fuel, etc.), heating oil, liquefied petroleum gas, etc.

Petrochemicals can be used to make specialty chemicals, such as plastics, resins, fibers, elastomers, pharmaceuticals, lubricants, or gels. Specialty chemicals have many commercial uses. Examples of specialty chemicals which can be produced from petrochemical raw materials include fatty acids, hydrocarbons (e.g., long chain hydrocarbons, branched chain hydrocarbons, saturated hydrocarbons, unsaturated hydrocarbons, etc.), fatty alcohols, fatty esters, fatty aldehydes, ketones, lubricants, etc. Fatty acids are used commercially as surfactants. Surfactants can be found, for example, in detergents and soaps. Fatty acids can also be used as additives in fuels, lubricating oils, paints, lacquers, candles, shortenings, cosmetics, and emulsifiers. In addition, fatty acids are used as accelerator activators in rubber products. Fatty acids can also be used as a feedstock to produce methyl esters, amides, amines, acid chlorides, anhydrides, ketene dimers, peroxy acids and esters.

Fatty esters have many commercial uses. For example, biodiesel, an alternative fuel, is comprised of esters (e.g., fatty acid methyl ester (FAME), fatty acid ethyl esters (FAEE), etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plastics, plasticizers, flame retardants, and additives in gasoline and oil. In addition, esters can be used in the manufacture of polymers, films, textiles, dyes, and pharmaceuticals.

Similarly, fatty alcohols have numerous commercial uses. For example, worldwide annual sales of fatty alcohols and their derivatives are in excess of US$1 billion. The shorter chain fatty alcohols are used in the cosmetic and food industries as emulsifiers, emollients, and thickeners. Due to their amphiphilic nature, fatty alcohols behave as nonionic surfactants, which are useful in personal care and household products, for example, detergents. In addition, fatty alcohols are used in waxes, gums, resins, pharmaceutical lotions, lubricating oil additives, textile antistatic and finishing agents, plasticizers, cosmetics, industrial solvents, and solvents for fats.

Acetyl CoA carboxylase (ACC) plays an important role in regulating fatty acid synthesis and degradation. It is a biotin-dependent enzyme complex that catalyzes the first committed step of fatty acid biosynthesis, i.e., the irreversible carboxylation of acetyl-CoA to malonyl-CoA. ACC produces malonyl-CoA via its two catalytic activities, i.e., biotin carboxylase (BC) and carboxyltransferase (CT). In most prokaryotes, ACC is a multi-subunit enzyme that includes four polypeptides (subunits), encoded by distinct genes whose coordinate expression is controlled through multiple levels of regulation (Cronan et al. (2002) *Progress in Lipid Research* 41:407-435; James et al. (2004) *Journal of Biological Chemistry* 279(4):2520-2527). The four polypeptides of ACC assemble into a complex at a fixed ratio (Broussard et al. (2013) *Structure* 21:650-657). More specifically, the ACC reaction requires four proteins, i.e., biotin carboxylase (BC), biotinoyl (or biotin) carboxyl carrier protein (BCCP), and two proteins that form the carboxyltransferase (CT). The overall ACC reaction can be assayed by the ATP-dependent conversion of the acid-labile $NaH^{14}CO_3$ to the acid-stable malonic acid. There are similarities and differences between the ACC subunits of bacteria and plant plastids. But despite the complexity of the plant proteins, the sequences that are essential for ACC activity are not significantly different from the bacterial homologues (Cronan et al., supra).

It has been reported that the *E. coli* ACC is the least stable of the known ACC enzymes. The overall activity can be measured only when all four subunits are present at high concentrations, although two partial reactions can be measured in dilute protein solutions. The stable complexes are believed to be the BC complex and the CT $alpha_2$ $beta_2$ complex. The full length BCCP has been purified as a dimer and there are hints of the presence of an unstable $BC_2$-$BCCP_2$ complex. Other bacterial ACCs seem more stable than that of *E. coli* and ACC activity can be measured in dilute extracts of *Helicobacter pylori* and *Pseudomonas citronellolis*. In addition, the plant plastid ACCs seem more stable than *E. coli* ACCs. However, as in *E. coli* further purification of the intact enzyme results in dissociation and loss of the ACC activity that can be restored by mixing fractions containing the partial reaction activities. The sub-complexes are BC-BCCP and CT with no evidence for free intact BCCP or free CT beta, suggesting that BCCP and CT beta are degraded when free in solution (Cronan et al., supra).

The identification of the *E. coli* acc genes including accA, accB, accC, and accD has facilitated the study of the ACC proteins. Radiation suicide selections have been used to isolate mutants in fatty acid synthesis including in genes accB and accD that encode ACC subunits BCCP and CT beta, respectively. The accB mutant has been studied more extensively and the mutation G133S is responsible for temperature sensitive growth. This mutation results in a steric clash within the biotinoyl domain. This resultant mutant protein is easily denatured at higher temperatures and is thus sensitive to intracellular proteases. The mutant BCCP strain has only about 25 percent of the normal level of BCCP when it is grown at 30° C., yet the rates of growth and fatty acid synthesis are normal (Cronan et al., supra). It is, however, known that increasing the concentration of all four proteins of ACC can improve the flux through fatty acid biosynthesis to a certain degree (Davis et al. (2000) *Journal of Biological Chemistry* 275(37):28593-28598). Conversely, it has been shown that *E. coli* ACC can be inhibited by acylated derivatives of ACP while ACP lacking an acyl moiety cannot inhibit ACC (Davies et al. (2001) *Journal of Bacteriology* 183(4): 1499-1503).

There is a need for alternative routes to create both fuels and products currently derived from petroleum. As such, microbial systems offer the potential for the biological production of numerous types of biofuels and chemicals. Renewable fuels and chemicals can be derived from genetically engineered organisms (such as bacteria, yeast and algae). Naturally occurring biosynthetic pathways can be genetically altered to enable engineered organisms to synthesize renewable fuel and chemical products. In addition, microbes can be tailored, or metabolically engineered, to utilize various carbon sources as feedstock for the production of fuel and chemical products. Thus, it would be desirable to engineer an ACC to produce higher yields of malonyl-derived compounds (e.g., fatty esters, fatty alcohols and other fatty acid derivatives as well as non-fatty acid compounds) when expressed in a recombinant host cell.

Notwithstanding the advances in the field, there remains a need for improvements in genetically modified enzymes, recombinant host cells, methods and systems in order to achieve robust and cost-effective production of fuels and chemicals through fermentation of recombinant host cells. The present disclosure addresses this need by providing ACC variants that increase the yield and titer of malonyl-derived compounds.

SUMMARY

One aspect of the disclosure provides a variant biotin carboxyl carrier protein (BCCP) having at least one mutation in its amino acid sequence. In one particular aspect the disclosure provides a variant biotin carboxyl carrier protein (BCCP) comprising at least one mutation in its amino acid sequence, wherein the variant BCCP has a polypeptide sequence from any one or more of the following sequence identifying numbers including SEQ ID NOS: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88 and 90. In one embodiment, the variant BCCP confers to a cell an increased production of a malonyl-CoA-derived compound when compared to a corresponding wild type cell. In another embodiment, the variant BCCP may confer improved acetyl-CoA carboxylase (ACC) activity when expressed in a cell, resulting in increased production of a malonyl-CoA-derived compound when compared to a corresponding wild type cell. The malonyl-CoA-derived compound includes, but is not limited to, a fatty acid derivative such as a free fatty acid, a fatty acid methyl ester (FAME), a fatty acid ethyl ester (FAEE), a fatty alcohol, a fatty amine, a beta hydroxy fatty acid derivative, a bifunctional fatty acid derivative (e.g., ω-hydroxy fatty acid, ω-hydroxy diol, ω-hydroxy FAME, ω-hydroxy FAEE), an unsaturated fatty acid derivative, as well as a non-fatty acid based compound such as a flavanone and/or a flavonoid, a polyketide, and 3-hydroxypropionic acid.

Another aspect of the disclosure provides a variant biotin carboxyl carrier protein (BCCP) having at least one mutation in its amino acid sequence, wherein the mutation is in the N-terminal amino acid region. In one embodiment, the mutation is in amino acid position 2 of SEQ ID NO: 2. In another embodiment, the variant BCCP confers to a cell an increased production of a malonyl-CoA-derived compound when compared to a corresponding wild type cell. In another embodiment, the variant BCCP may confer improved acetyl-CoA carboxylase (ACC) activity when expressed in a cell, resulting in increased production of a malonyl-CoA-derived compound when compared to a corresponding wild type cell.

Another aspect of the disclosure provides a variant biotin carboxyl carrier protein (BCCP) having at least one mutation in its amino acid sequence, wherein the variant BCCP is selected from SEQ ID NOS: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88 and/or 90. In one embodiment, the variant BCCP confers to a cell an increased production of a malonyl-CoA-derived compound when compared to a corresponding wild type cell. In another embodiment, the variant BCCP may confer improved acetyl-CoA carboxylase (ACC) activity when expressed in a cell, resulting in increased production of a malonyl-CoA-derived compound when compared to a corresponding wild type cell.

Still another aspect of the disclosure provides a variant BCCP that is encoded by a variant accB gene or accB nucleic acid sequence, wherein the nucleic acid sequence is selected from SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87 and/or 89.

Another aspect of the disclosure provides a recombinant cell or recombinant microorganism that expresses a variant BCCP, wherein the variant BCCP has at least one mutation in its amino acid sequence. In one embodiment, the cell is a host cell. In another embodiment, the cell is a microbial cell or microbial host cell. In another embodiment, the microorganism is a microbial cell or microbial host cell or a microbe. In one embodiment, the mutation is in the N-terminal amino acid region. In another embodiment, the mutation is in amino acid position 2 of SEQ ID NO: 2. In another embodiment, the mutation is a substitution. In various embodiments, the substitution is aspartate (D) to asparagine (N); or aspartate (D) to histidine (H); or aspartate (D) to isoleucine (I); or aspartate (D) to threonine (T); or aspartate (D) to serine (S); or aspartate (D) to tyrosine (Y); or aspartate (D) to arginine (R); or aspartate (D) to leucine (L); or aspartate (D) to glutamine (Q); or aspartate (D) to glutamate (G). In another embodiment, the variant BCCP has SEQ ID NO: 6 encompassing a polypeptide with a mutation that includes a substitution of aspartate (D) to asparagine (N). In another embodiment, the variant BCCP has SEQ ID NO: 4 or SEQ ID NO: 8 encompassing a polypeptide with a mutation that includes a substitution of aspartate (D) to histidine (H). In another embodiment, the variant BCCP has SEQ ID NO: 10 or SEQ ID NO: 12 encompassing a polypeptide with a mutation that includes a substitution of aspartate (D) to isoleucine (I). In one embodiment, the variant BCCP has at least one mutation in its amino acid sequence and confers to a recombinant cell an increased production of a malonyl-CoA-derived compound when compared to a corresponding wild type cell. In another embodiment, the variant BCCP has at least one mutation in its amino acid sequence and may confer improved acetyl-CoA carboxylase (ACC) activity to a recombinant cell, resulting in increased production of a malonyl-CoA-derived compound when compared to a corresponding wild type cell. In another embodiment, the cell is a recombinant microorganism or recombinant host cell that can be contrasted with or compared to a wild type microorganism or wild type host cell. In another embodiment, the cell is microbial in nature.

Yet another aspect of the disclosure provides a method of producing a malonyl-CoA-derived compound, including culturing a cell that expresses a variant BCCP in a fermentation broth containing a carbon source. The malonyl-CoA-derived compound includes a fatty acid derivative, such as, for example, a fatty acid, a fatty acid methyl ester (FAME), a fatty acid ethyl ester (FAEE), a fatty alcohol, a fatty amine, a beta hydroxy fatty acid derivative, a bifunctional fatty acid derivative (e.g., ω-hydroxy fatty acids, ω-hydroxy diols, ω-hydroxy FAME, ω-hydroxy FAEE), an unsaturated fatty acid derivative, as well as a non-fatty acid based compound such as a flavanone and/or a flavonoid, a polyketide, and 3-hydroxypropionic acid. In one embodiment, the cell is a recombinant microorganism or recombinant host cell that can be contrasted with or compared to a wild type microorganism or wild type host cell, respectively. In another embodiment, the cell is microbial in nature.

The disclosure further contemplates a variant operon controlling the expression of a BCCP. In one embodiment, the operon results in a change in the BCCP expression in a recombinant cell as compared to a wild type cell. In one embodiment, the cell is a recombinant microbial host cell or recombinant microorganism as compared to a wild type microbial host cell or wild type microorganism, respectively. In another embodiment, the operon results in an increase in the BCCP expression in a recombinant cell and thereby improves acetyl-CoA carboxylase (ACC) activity in the recombinant cell, resulting in increased production of a malonyl-CoA-derived compound when compared to a corresponding wild type cell. In one aspect, the variant operon further includes a promoter. The promoter includes, but is not limited to, a heterologous promoter, a heterologous promoter variant, and a synthetic promoter. In one embodiment, the promoter includes a genetically modified accBC promoter, a naturally occurring E. coli promoter, or an E. coli promoter variant. In another embodiment, the promoter is an accBC promoter variant. In another embodiment, the promoter is a T5 promoter or T5 promoter variant. In one embodiment, the promoter is an accBC T5 promoter. In another embodiment, the accBC T5 promoter is selected from SEQ ID NOS: 93, 94, 95, or 96 or variations thereof.

The disclosure further provides a recombinant microorganism or host cell encompassing a variant operon that controls the expression of a BCCP. In one embodiment, the operon results in a change in the BCCP expression. In one embodiment, the operon results in an increase in the BCCP expression in a recombinant cell, and thereby improves acetyl-CoA carboxylase (ACC) activity in the recombinant cell, resulting in increased production of a malonyl-CoA-derived compound when compared to a corresponding wild type cell. In another embodiment, the variant operon further includes a promoter.

Another aspect of the disclosure provides a method of producing a malonyl-CoA-derived compound, including culturing a microorganism or host cell that expresses a variant operon in a fermentation broth containing a carbon source. In one embodiment, the cell is a recombinant microorganism or recombinant host cell that can be contrasted with or compared to a wild type microorganism or wild type host cell, respectively. In another embodiment, the cell is microbial in nature. The malonyl-CoA-derived compound includes a fatty acid, a fatty acid methyl ester (FAME), a fatty acid ethyl ester (FAEE), a fatty alcohol, a fatty amine, a beta hydroxy fatty acid derivative, a bifunctional fatty acid derivative (e.g., ω-hydroxy fatty acids, ω-hydroxy diols, ω-hydroxy FAME, ω-hydroxy FAEE), an unsaturated fatty acid derivative, as well as a non-fatty acid based compound such as a flavanone and/or a flavonoid, a polyketide, and 3-hydroxypropionic acid.

Still another aspect of the disclosure provides a method of producing a malonyl-CoA-derived compound, including culturing a host cell expressing a variant BCCP and a variant operon in a fermentation broth, containing a carbon source. In one embodiment, the cell is a recombinant microorganism or recombinant host cell that can be contrasted with or compared to a wild type microorganism or wild type host cell, respectively. In another embodiment, the cell is microbial in nature. The malonyl-CoA-derived compound includes a fatty acid, a fatty acid methyl ester (FAME), a fatty acid ethyl ester (FAEE), a fatty alcohol, a fatty amine, a beta hydroxy fatty acid derivative, a bifunctional fatty acid derivative (including ω-hydroxy fatty acids, ω-hydroxy diols, ω-hydroxy FAME, ω-hydroxy FAEE), an unsaturated fatty acid derivative, as well as a non-fatty acid based compound such as a flavanone and/or a flavonoid, a polyketide, and 3-hydroxypropionic acid.

The disclosure further contemplates a microorganism that encompasses a variant biotin carboxyl carrier protein (BCCP) having at least one mutation in its amino acid sequence. In one embodiment, the variant BCCP has a mutation in an N-terminal amino acid region. In another embodiment, the mutation is a substitution. In various embodiments, the substitution is aspartate (D) to asparagine (N); or aspartate (D) to histidine (H); or aspartate (D) to isoleucine (I); or aspartate (D) to threonine (T); or aspartate (D) to serine (S); or aspartate (D) to tyrosine (Y); or aspartate (D) to arginine (R); or aspartate (D) to leucine (L); or aspartate (D) to glutamine (Q); or aspartate (D) to glutamate (G). In another embodiment, the variant BCCP has one or more mutation(s), including substitutions of aspartate (D) to asparagine (N); aspartate (D) to histidine (H); aspartate (D) to isoleucine (I); aspartate (D) to threonine (T); aspartate (D) to serine (S); aspartate (D) to tyrosine (Y); aspartate (D) to arginine (R); aspartate (D) to leucine (L); aspartate (D) to glutamine (Q); and/or aspartate (D) to glutamate (G). In another embodiment, the variant BCCP has SEQ ID NO: 6 encompassing a polypeptide with a mutation that includes a substitution of aspartate (D) to asparagine (N). In another embodiment, the variant BCCP has SEQ ID NO: 4 or SEQ ID NO: 8 encompassing a polypeptide with a mutation that includes a substitution of aspartate (D) to histidine (H). In another embodiment, the variant BCCP has SEQ ID NO: 10 or SEQ ID NO: 12 encompassing a polypeptide with a mutation that includes a substitution of aspartate (D) to isoleucine (I). In another embodiment, the expression of the variant BCCP confers an increased production of a malonyl-CoA-derived compound to the microorganism. In another embodiment, the expression of the variant BCCP may confer improved acetyl-CoA carboxylase (ACC) activity in the microorganism, resulting in increased production of a malonyl-CoA-derived compound by the microorganism. The malonyl-CoA-derived compound includes, but is not limited to, a fatty acid, a fatty acid methyl ester (FAME), a fatty acid ethyl ester (FAEE), a fatty alcohol, a fatty amine, a beta hydroxy fatty acid derivative, a bifunctional fatty acid derivative, an unsaturated fatty acid derivative, a flavanone, a flavonoid, a polyketide, and 3-hydroxypropionic acid. In one embodiment, the malonyl-CoA-derived compound is a FAME or a FAEE. In another embodiment, the malonyl-CoA-derived compound is a fatty alcohol. In another embodiment, the microorganism is a microbial cell. In yet another embodiment, the microbial cell is a recombinant cell. Examples of microbial cells include, but are not limited to, cells from the genus *Escherichia, Bacillus, Cyanophyta, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, and *Streptomyces*. In one embodiment, the microbial cell is from the genus *Escherichia*. In one embodiment, the microbial cell is from *Escherichia coli*. In another embodiment, the microbial cell is from a cyanobacteria or the genus *Cyanophyta*. In another embodiment, the microbial cell is from a cyanobacteria or *Cyanophyta* including, but not limited to, *Prochlorococcus, Synechococcus, Synechocystis, Cyanothece*, and *Nostoc punctiforme*. In another embodiment, the microbial cell is from a specific cyanobacterial species including, but not limited to, *Synechococcus elongatus* PCC7942, *Synechocystis* sp. PCC6803, and *Synechococcus* sp. PCC7001.

Another aspect of the disclosure provides a recombinant microorganism having an altered expression of a nucleic acid sequence including accB or accC or a combination thereof, resulting in altered production of a malonyl-CoA-derived compound by the microorganism. In one embodiment, the altered expression is increased expression. In another embodiment, the altered expression is decreased expression. In yet another embodiment, the altered expression is due to a change in one or more promoters that drive expression of the nucleic acid sequence. The nucleic acid sequence of accB codes for BCCP. In one embodiment, the variant nucleic acid sequence of accB codes for the variant BCCP. In one embodiment, the malonyl-CoA-derived compound includes, but is not limited to, a fatty acid, a fatty acid methyl ester (FAME), a fatty acid ethyl ester (FAEE), a fatty alcohol, a fatty amine, a beta hydroxy fatty acid derivative, a bifunctional fatty acid derivative, an unsaturated fatty acid derivative, a flavanone, a flavonoid, a polyketide, and 3-hydroxypropionic acid. In one embodiment, the microorganism includes, but is not limited to, microorganisms from the genus *Escherichia, Bacillus, Cyanophyta, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia*, or *Streptomyces*. In one embodiment, the microbial cell is from the genus *Escherichia*. In one embodiment, the microbial cell is from *Escherichia coli*. In another embodiment, the microbial cell is from a cyanobacteria or the genus *Cyanophyta*. In still another embodiment, the microorganism is a cyanobacteria or *Cyanophyta* from *Prochlorococcus, Synechococcus, Synechocystis, Cyanothece*, or *Nostoc punctiforme*. In one embodiment, the microorganism is a cyanobacterial species from *Synechococcus elongatus* PCC7942, *Synechocystis* sp. PCC6803, or *Synechococcus* sp. PCC7001.

Another aspect of the disclosure provides a microorganism or host cell that has an altered expression of an ACC variant and further expresses a fatty acid biosynthesis protein. In one embodiment, the host cell is a microbial cell. In another embodiment, the host cell is a recombinant cell. In yet another embodiment, the host cell is a recombinant bacterial cell. In another embodiment, the ACC variant is a biotin carboxyl carrier protein (BCCP) or a biotin carboxylase (BC) or a combination thereof. In one embodiment, the altered expression is increased or decreased expression. In one embodiment, the altered expression is increased expression, wherein the increased expression results in an increased production of a malonyl-CoA-derived compound when the microbial cell is cultured with a carbon source.

In certain embodiments of the present disclosure the host cell may further express a biosynthetic protein that has enzymatic activity that can increase production of fatty acid derivatives. In one embodiment, the protein with enzymatic activity may be natively present in the host cell and its gene may be overexpressed via a promoter or other genetic alteration. In another embodiment, the protein with enzymatic activity may be the result of an exogenous or heterologous gene that is expressed in the host cell. Examples of such enzymatic activities include, but are not limited to, thioesterase activity (E.C. 3.1.2.* or E.C. 3.1.2.14 or E.C. 3.1.1.5), ester synthase activity (E.C. 2.3.1.75), acyl-ACP reductase (AAR) activity (E.C. 1.2.1.80), alcohol dehydrogenase activity (E.C. 1.1.1.1.), fatty alcohol acyl-CoA reductase (FAR) activity (E.C. 1.1.1.*), carboxylic acid reductase (CAR) activity (EC 1.2.99.6), decarbonylase or deformylase activity, acyl-CoA reductase activity (E.C. 1.2.1.50), acyl-CoA synthase (FadD) activity (E.C. 2.3.1.86), OleA activity, and OleBCD activity.

In still another aspect, the disclosure provides a microorganism or host cell that has an altered expression of an ACC variant and further expresses a fatty acid biosynthesis protein, wherein the altered expression is increased expression that results in an increased production of a malonyl-CoA-derived compound when the cell is cultured with a carbon source. In one embodiment, the host cell is a microbial cell. In another embodiment, the host cell is a recombinant cell. In yet another embodiment, the host cell is a recombinant bacterial cell. In still another embodiment, the microorganism or host cell is a recombinant cell that can be compared to or contrasted with a wild type cell under the same conditions. Herein the malonyl-CoA-derived compound includes, but is not limited to, a fatty acid, a fatty acid methyl ester (FAME), a fatty acid ethyl ester (FAEE), a fatty alcohol, a fatty amine, a beta hydroxy fatty acid derivative, a bifunctional fatty acid derivative, an unsaturated fatty acid derivative, a flavanone, a flavonoid, a polyketide, and 3-hydroxypropionic acid. In one embodiment, the microbial cell is selected from cells of the genus *Escherichia, Bacillus, Cyanophyta, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleu-* rotus, Trametes, Chrysosporium, Saccharomyces, Stenotrophamonas, Schizosaccharomyces, Yarrowia, or Streptomyces.

Another aspect of the disclosure provides a variant biotin carboxyl carrier protein (BCCP) having SEQ ID NO: 6. In one embodiment, the mutation is in an N-terminal amino acid region with a substitution of aspartate (D) to asparagine (N), wherein the substitution is in amino acid position 2. In another embodiment, the varian BCCP is encoded by a variant accB gene, wherein the variant accB gene has a nucleic acid sequence of SEQ ID NO: 5. Another aspect of the disclosure provides a variant biotin carboxyl carrier protein (BCCP) having SEQ ID NO: 4 or SEQ ID NO: 8. In one embodiment, the mutation is in an N-terminal amino acid region with a substitution of aspartate (D) to histidine (H), wherein the substitution is in amino acid position 2. In another embodiment, the varian BCCP is encoded by a variant accB gene, wherein the variant accB gene has a nucleic acid sequence of SEQ ID NO: 3 or SEQ ID NO: 7, respectively. Another aspect of the disclosure provides a variant biotin carboxyl carrier protein (BCCP) having SEQ ID NO: 10 or SEQ ID NO: 12. In one embodiment, the mutation is in an N-terminal amino acid region with a substitution of aspartate (D) to isoleucine (I), wherein the substitution is in amino acid position 2. In another embodiment, the variant BCCP is encoded by a variant accB gene, wherein the variant accB gene has a nucleic acid sequence of SEQ ID NO: 9 or SEQ ID NO: 11, respectively.

In various embodiments, the variant BCCPs confer to a recombinant cell an increased production of a malonyl-CoA-derived compound when compared to a corresponding wild type cell, wherein said malonyl-CoA-derived compound includes a fatty acid derivative of a fatty acid, a fatty acid methyl ester (FAME), a fatty acid ethyl ester (FAEE), a fatty alcohol, a fatty amine, a beta hydroxy fatty acid derivative, a bifunctional fatty acid derivative, and an unsaturated fatty acid derivative; or a non-fatty acid compound such as a flavanone, a flavonoid, a polyketide, and 3-hydroxypropionic acid. The present disclosure further encompasses recombinant microorganisms that include or express the variant BCCPs. In one embodiment, the microorganisms are selected from microorganisms of the genus Escherichia, Bacillus, Cyanophyta, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia, or Streptomyces.

Further contemplated is a method of producing a malonyl-CoA-derived compound, including culturing the recombinant microorganism expressing the variant BCCP in a fermentation broth containing a carbon source. The malonyl-derived compound produced by this method includes a fatty acid derivative including a fatty acid, a fatty acid methyl ester (FAME), a fatty acid ethyl ester (FAEE), a fatty alcohol, a fatty amine, a beta hydroxy fatty acid derivative, a bifunctional fatty acid derivative, and an unsaturated fatty acid derivative; or a non-fatty acid compound such as a flavanone, a flavonoid, a polyketide, and 3-hydroxypropionic acid.

BRIEF DESCRIPTION OF THE FIGURES

The present disclosure is best understood when read in conjunction with the accompanying figures, which serve to illustrate the preferred embodiments. It is understood, however, that the disclosure is not limited to the specific embodiments disclosed in the figures.

FIG. 2 depicts an alignment of seven amino acid sequences of BCCP from seven different species. The boxed area shows a motif that is conserved across most BCCP species.

DETAILED DESCRIPTION

General Overview

Figure 1:
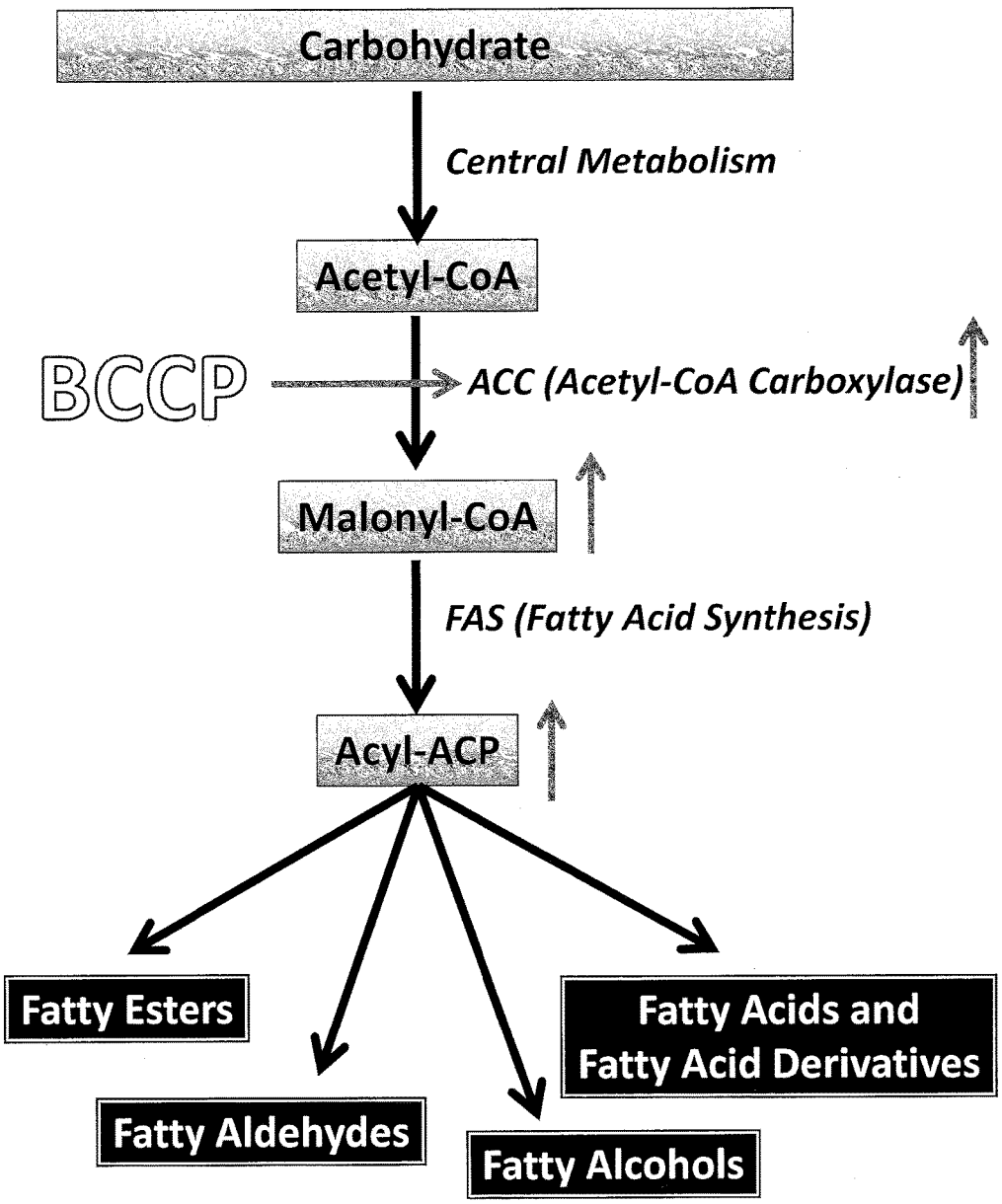
FIG. 1 is a schematic of one embodiment of an engineered biochemical pathway that involves acetyl-CoA carboxylase (ACC) variants such as a variant biotin carboxyl carrier protein (BCCP). As depicted, BCCP may confer improved acetyl-CoA carboxylase (ACC) activity when expressed in a cell. This may lead to increased production of malonyl-CoA and acyl-ACP, which in turn may lead to increased production of malonyl-CoA-derived compounds, including, for example, fatty acid derivatives such as fatty esters, fatty aldehydes, fatty alcohols, fatty acids, and other fatty acid derivatives.

The disclosure relates to variant acetyl-CoA carboxylase (ACC) polypeptide(s) or ACC variant(s) that can be expressed in a microorganism. These ACC variants are genetically altered and are believed to confer improved enzymatic activity for the increased production of malonyl-CoA derived compounds including fatty acid derivatives. Herein, the disclosure relates to polypeptide(s) and protein(s) that may lead to improved acetyl-CoA carboxylase (ACC) activity when expressed in a host cell, when compared to the corresponding ACC activity in a wild type cell. In order to illustrate this, ACC genes were altered by introducing mutations in one ACC gene as well as one ACC operon. Both of these alterations can independently increase fatty acid derivative production in a host cell. These mutations are expected to improve the titer and yield of a product derived from malonyl-CoA, including but not limited to, fatty acid-derived compounds (i.e., fatty acid derivatives) such as, for example, fatty acids, fatty esters, fatty alcohols, fatty aldehydes, fatty amines, bifunctional fatty acid derivatives, and non-fatty acid based compounds such as, for example, flavanones and flavonoids, polyketides, and 3-hydroxypropionic acid. Examples of fatty esters are fatty acid methyl esters (FAME) and fatty acid ethyl esters (FAEE). Examples of bifunctional fatty acid derivatives include, but are not limited to, ω-hydroxy fatty acids, ω-hydroxy diols, ω-hydroxy FAME, and ω-hydroxy FAEE.

It has been stipulated, that in order to produce higher yields of malonyl-CoA derived compounds, the increased expression of all four ACC genes encoding the complete ACC complex is required (Davis et al. (2000) supra). However, the present disclosure reveals the surprising finding that targeted mutations in only one ACC gene can improve the production of compounds that are derived from malonyl-CoA, including fatty acid derivatives. For example, targeted mutations in the accB gene and/or targeted expression changes in the accBC operon significantly improved fatty ester production by up to 630 percent (see FIG. 5 as well as Table 1 and the Examples, infra). Without wishing to be bound by theory, the variant ACC polypeptides or ACC variants are believed to directly or indirectly confer onto ACC complexes improved enzymatic activity that leads to a higher production of malonyl-CoA derived compounds in host cells. The specific activity of the host cell is believed to be increased, thereby resulting in increased production of malonyl-CoA derived compounds. Such malonyl-CoA derived compounds include fatty acid derivatives and non-fatty acid based compounds.

Definitions

As used in this specification and the appended claims, the singular forms "a," "an" and "the" include plural referents unless the context clearly dictates otherwise. Thus, for example, reference to "a host cell" includes two or more such host cells, reference to "a fatty ester" includes one or more fatty esters, or mixtures of esters, reference to "a nucleic acid sequence" includes one or more nucleic acid sequences, reference to "an enzyme" includes one or more enzymes, and the like.

Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers" or alternatively a simply "Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction they catalyze. For example, the acetyl-CoA carboxylase (ACC) enzymatic activity is classified under E.C. 6.4.1.2. ACC is a multi-subunit enzyme complex present in most prokaryotes and in the chloroplasts of most plants and algae. ACC catalyzes the reaction of ATP and acetyl-CoA and $HCO_3^-$ to ADP and phosphate and malonyl-CoA. The functionality of ACC is conserved in most prokaryotes from one species to the next. Thus, different microbial species can carry out the same acetyl-CoA carboxylase (ACC) enzymatic activity that is classified under E.C. 6.4.1.2.

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

The term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms "polypeptide" and "protein" are used interchangeably to refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide. DNA or RNA encoding the expressed protein can also be inserted into the host chromosome via homologous recombination or other means well known in the art, and is so used to transform a host cell to produce the polypeptide. Similarly, the terms "recombinant polynucleotide" or "recombinant nucleic acid" or "recombinant DNA" are produced by recombinant techniques that are known to those of skill in the art.

As used herein, the terms "homolog," and "homologous" refer to a polynucleotide or a polypeptide comprising a sequence that is at least about 50 percent (%) identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and sequence "identity" are used interchangeably.

One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In one preferred embodiment, the length of a first sequence that is aligned for comparison purposes is at least about 30%, preferably at least about 40%, more preferably at least about 50%, even more preferably at least about 60%, and even more preferably at least about 70%, at least about 80%, at least about 85%, at least about 90%, at least about 95%, at least about 98%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences. The comparison of sequences and determination of percent homology between two sequences can be accomplished using a mathematical algorithm, such as BLAST (Altschul et al. (1990) *J. Mol. Biol.* 215(3):403-410). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch (1970) *J. Mol. Biol.* 48:444-453). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) *BMC Bioinformatics* 6:278; Altschul et al. (2005) *FEBS J.* 272(20):5101-5109).

The term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and non-aqueous methods are described in that reference and either method can be used. Specific hybridization conditions referred to herein are as follows: (1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions—6×SSC at about 45° C., followed by one or more washes in 0.2×SSC, 0.1% SDS at 60° C.; (3) high stringency hybridization conditions—6× SSC at about 45° C., followed by one or more washes in 0.2.×SSC, 0.1% SDS at 65° C.; and (4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

An "endogenous" polypeptide refers to a polypeptide encoded by the genome of the parental cell (or host cell). An "exogenous" polypeptide refers to a polypeptide which is not encoded by the genome of the parental cell. A variant or mutant polypeptide is an example of an exogenous polypeptide. Thus, a non-naturally-occurring nucleic acid molecule is considered to be exogenous to a cell once introduced into the cell. A nucleic acid molecule that is naturally-occurring can also be exogenous to a particular cell. For example, an entire coding sequence isolated from cell X is an exogenous nucleic acid with respect to cell Y once that coding sequence is introduced into cell Y, even if X and Y are the same cell type.

The term "overexpressed" means that a gene is caused to be transcribed at an elevated rate compared to the endogenous transcription rate for that gene. In some examples, overexpression additionally includes an elevated rate of translation of the gene compared to the endogenous translation rate for that gene. Methods of testing for overexpression are well known in the art, for example transcribed RNA levels can be assessed using rtPCR and protein levels can be assessed using SDS page gel analysis.

The term "heterologous" means derived from a different organism, different cell type, or different species. As used herein it refers to a nucleotide-, polynucleotide-, polypeptide- or protein sequence, not naturally present in a given organism. For example, a polynucleotide sequence that is native to cyanobacteria can be introduced into a host cell of *E. coli* by recombinant methods, and the polynucleotide from cyanobacteria is then heterologous to the *E. coli* cell (e.g., recombinant cell). The term "heterologous" may also be used with reference to a nucleotide-, polynucleotide-, polypeptide-, or protein sequence which is present in a recombinant host cell in a non-native state. For example, a "heterologous" nucleotide, polynucleotide, polypeptide or protein sequence may be modified relative to the wild type sequence naturally present in the corresponding wild type host cell, e.g., a modification in the level of expression or in the sequence of a nucleotide, polynucleotide, polypeptide or protein.

As used herein, the term "fragment" of a polypeptide refers to a shorter portion of a full-length polypeptide or protein ranging in size from two amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

The term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

A "mutation", as used herein, refers to a permanent change in a nucleic acid position of a gene or in an amino acid position of a polypeptide or protein. Mutations include substitutions, additions, insertions, and deletions. For example, a mutation in an amino acid position can be a substitution of one type of amino acid with another type of amino acid (e.g., an aspartate (D) may be substituted with an tyrosine (Y); a lysine (L) may be substituted with a threonine (T); etc.). As such, a polypeptide or a protein can have one or more mutations wherein one amino acid is substituted with another amino acid. For example, an ACC related polypeptide or protein can have one or more mutations in its amino acid sequence.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., Science, 236: 1237-1245 (1987)). Exemplary expression control sequences are described in, for example, Goeddel, Gene Expression Technology: Methods in Enzymology, Vol. 185, Academic Press, San Diego, Calif. (1990). In the methods of the disclosure, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, in as much as a plasmid is the most commonly used form of vector. However, also included are such other forms of expression vectors that serve equivalent functions and that become known in the art subsequently hereto. In some embodiments, a recombinant vector further includes a promoter operably linked to the polynucleotide sequence. In some embodiments, the promoter is a developmentally-regulated, an organelle-specific, a tissue-specific, an inducible, a constitutive, or a cell-specific promoter. The recombinant vector typically comprises at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

The terms "recombinant cell" and "recombinant host cell" are used interchangeably herein and refer to a cell that may express an ACC variant and/or encompasses a variant operon that may increase the specific activity of the recombinant cell to produce malonyl-CoA derived compounds. A recombinant cell can be derived from a microorganism such as a bacterium, a virus or a fungus. In addition, a recombinant cell can be derived from a plant or an animal cell. The recombinant cell can be used to produce one or more fatty acid derivatives including, but not limited to, fatty acids, fatty esters (e.g., waxes, fatty acid esters, fatty esters, fatty acid methyl esters (FAME), fatty acid ethyl esters (FAEE)), fatty alcohols, short and long chain alcohols, fatty aldehydes, hydrocarbons, fatty amines, terminal olefins, internal olefins, ketones, bifunctional fatty acid derivatives (e.g., ω-hydroxy fatty acids, ω-hydroxy diols, ω-hydroxy FAME, ω-hydroxy FAEE); a well as non-fatty acid compounds such as flavanones, flavonoids, polyketides, and 3-hydroxypropionic acid. In some embodiments, the recombinant cell includes one or more polynucleotides, each polynucleotide encoding a polypeptide having fatty acid biosynthetic enzyme activity, wherein the recombinant cell produces a fatty acid derivative composition when cultured in the presence of a carbon source under conditions effective to express the polynucleotides.

As used herein, the term "microorganism" refers to a microscopic organism. Examples of a microorganism are a bacterium, a virus, or a fungus. In one embodiment, a microorganism is a bacterial cell. In another embodiment, a microorganism is a prokaryote or prokaryotic cell. In yet another embodiment, a microorganism is a fungal cell such as a yeast cell. In another embodiment, a microorganism is a viral cell. In a related embodiment, a "recombinant microorganism" is a microorganism that has been genetically altered and expresses or encompasses an exogenous and/or heterologous nucleic acid sequence.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

Figure 4:
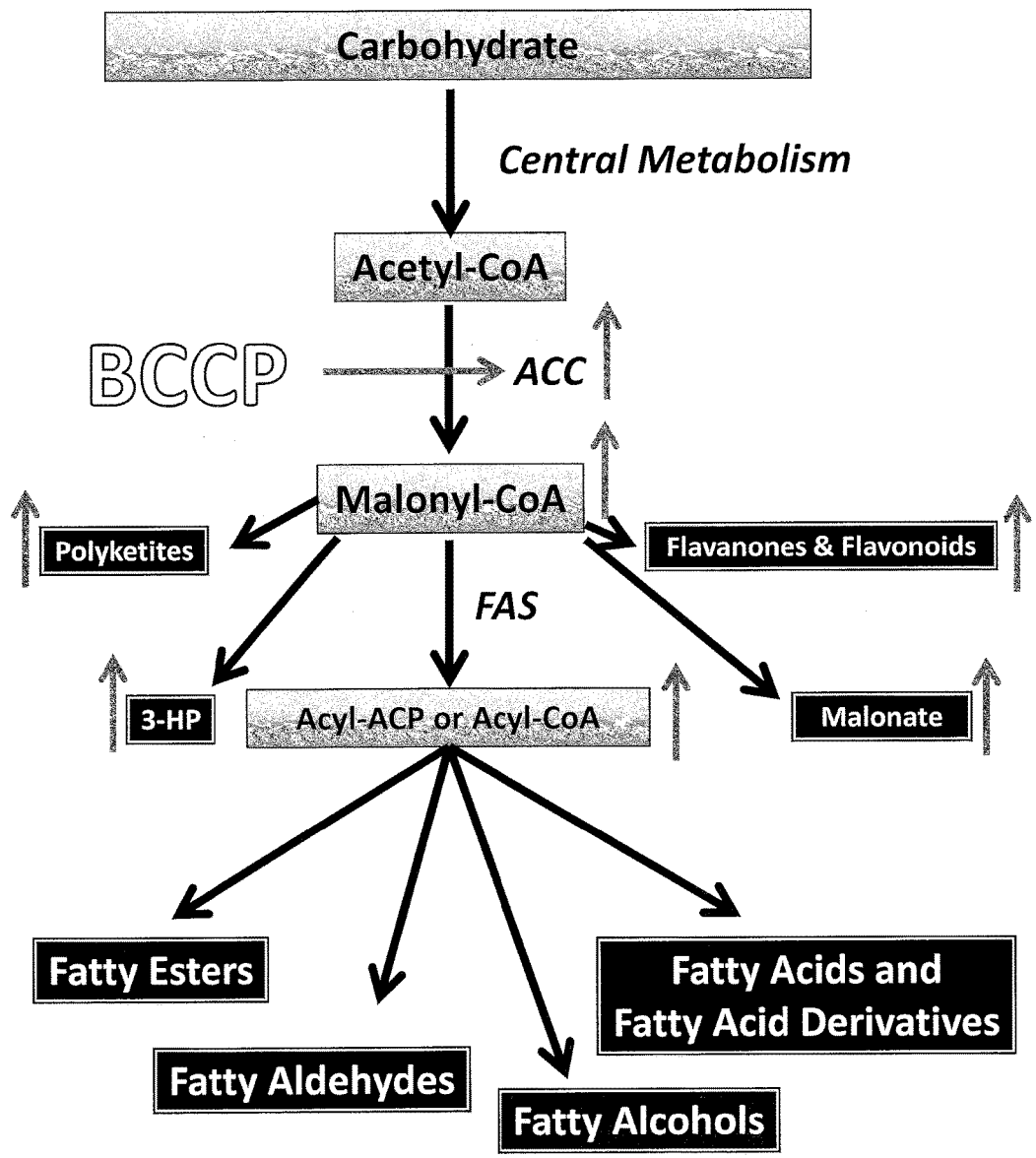
FIG. 4 is a summary of several embodiments of an engineered biochemical pathway that involves acetyl-CoA carboxylase (ACC) variants such as a variant biotin carboxyl carrier protein (BCCP). As shown, BCCP may confer improved acetyl-CoA carboxylase (ACC) activity when expressed in a cell. This may lead to increased production of malonyl-CoA and malonyl-CoA derived compounds, including polyketides, 3-hydroxypropionic acid (3-HP), flavanones and flavonoids as well as increased intermediates such as, for example, increased acyl-CoA (see also FIG. 3); increased acyl-ACP (see also FIG. 1); as well as increased malonate (or malonic acid). Increased intermediates may further lead to increased end-products such as fatty acid derivatives, including fatty acids, fatty esters, fatty aldehydes, fatty alcohols and other fatty acid derivatives.

The term "malonyl-CoA derived compound" includes any compound or chemical entity (i.e., intermediate or end product) that is made via a biochemical pathway, wherein malonyl-CoA functions as intermediate and/or is made upstream of the compound or chemical entity (e.g., see FIG. 4). For example, a malonyl-CoA derived compound includes, but is not limited to, a fatty acid derivative such as, for example, a fatty acid; a fatty ester including, but not limited to a fatty acid methyl ester (FAME) and/or a fatty acid ethyl ester (FAEE); a fatty alcohol; a fatty aldehyde; a fatty amine; an alkane; an olefin or alkene; a hydrocarbon; a beta hydroxy fatty acid derivative, a bifunctional fatty acid derivative, and an unsaturated fatty acid derivative. A malonyl-CoA derived compound further includes, but is not limited to, a non-fatty acid compound such as, for example, a flavanone, a flavonoid, a polyketide, malonate, and 3-hydroxypropionic acid.

The term "fatty acid" means a carboxylic acid having the formula RCOOH. R represents an aliphatic group, preferably an alkyl group. R can comprise between about 4 and about 22 carbon atoms. Fatty acids can have a branched chain or straight chain and may be saturated, monounsaturated, or polyunsaturated.

A "fatty acid derivative" is a product made in part from the fatty acid biosynthetic pathway of the production host organism. "Fatty acid derivatives" include products made from malonyl-CoA derived compounds including acyl-ACP or acyl-ACP derivatives. Exemplary fatty acid derivatives include fatty acids, fatty esters (e.g., waxes, fatty acid esters, fatty esters, fatty acid methyl esters (FAME), fatty acid ethyl esters (FAEE)), fatty amines, fatty aldehydes, fatty alcohols, short and long chain alcohols, hydrocarbons, ketones, terminal olefins, internal olefins, ketones, beta hydroxy fatty acid derivatives, bifunctional fatty acid derivatives (e.g., ω-hydroxy fatty acids, ω-hydroxy diols, ω-hydroxy FAME, ω-OH FAEE), and unsaturated fatty acid derivatives. "Fatty acid derivatives" also include products made from malonyl-CoA derived compounds such as acyl-CoA or acyl-CoA derivatives.

A "fatty acid derivative composition" as referred to herein is produced by a recombinant host cell and typically includes a mixture of fatty acid derivatives. In some cases, the mixture includes more than one type of fatty acid derivative product (e.g., fatty acids, fatty esters, fatty alcohols, fatty aldehydes, fatty amine, bifunctional fatty acid derivatives, etc.). In other cases, a fatty acid derivative composition may include, for example, a mixture of fatty esters (or another fatty acid derivative) with different chain lengths, saturation and/or branching characteristics. In still other cases, the fatty acid derivative composition may comprise both a mixture of more than one type of fatty acid derivative product and fatty acid derivatives with different chain lengths, saturation and/or branching characteristics. In yet other cases, a fatty acid derivative composition may include, for example, a mixture of fatty esters and beta hydroxy esters. In still other cases, a fatty acid derivative composition may include, for example, a mixture of fatty alcohols and fatty aldehydes. In still other cases, a fatty acid derivative composition may include, for example, a mixture of FAME and/or FAEE.

The terms "variant biotin carboxyl carrier protein (BCCP)" and "biotin carboxyl carrier protein (BCCP) variant" are used interchangeably herein and refer to an ACC variant that has one or more mutations in its amino acid sequence. In one example, the amino acid sequence ranges from 1 (i.e., the initial methionine (M) based on the ATG start site) to 156. Such a BCCP variant can have one or more mutation(s) in the amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, and/or 156. In one embodiment, the mutations include mutations in the N-terminal amino acid region that ranges from about position 1 to about position 60. In one embodiment, the mutations include mutations in amino acid position 2 (right after the start codon).

The term "expression confers to (or results in) a recombinant cell with an increased production of a malonyl-CoA-derived compound when compared to a corresponding wild type cell" refers to the function of an ACC related polypeptide or protein that has one or more mutations in its amino acid sequence (i.e., an ACC variant or ACC mutant) and causes in a cell improved production of malonyl-CoA derived compound(s) when expressed in that cell, when compared to a wild type cell that does not express the ACC variant or mutant. It also refers to the function of an ACC variant that, when expressed in a cell, has the effect of causing a higher specific activity of the cell in producing malonyl-CoA derived compound(s). Without wishing to be bound by theory, this may be the result of directly or indirectly causing a higher acetyl-CoA carboxylase (ACC) enzymatic activity (E.C. 6.4.1.2) in the cell. This can be measured by comparing the titer and/or yield of a malonyl-CoA derived compound produced by the cell expressing the ACC variant with the titer and/or yield of a malonyl-CoA derived compound produced by a corresponding wild type cell (i.e., a cell that does not express the ACC variant). Those of skill in the art will appreciate that the methods for measurement are readily available, including, for example, gas chromatography flame ionization detector (GC-FID) and others. An example of an ACC variant protein is a biotin carboxyl carrier protein (BCCP) variant. The ACC variant(s) may encompass mutations in one and/or two of any of the four subunits of the ACC complex. The ACC variant(s) may encompass changes in concentration in any of one and/or two of the four subunits. When a cell has been transformed with an ACC variant it is a cell that expresses the ACC variant (e.g., a recombinant cell). In one embodiment, the titer and/or yield of a malonyl-CoA derived compound produced by a cell that expresses the ACC variant is at least twice that of a corresponding wild type cell (i.e., a corresponding cell that does not express the ACC variant). In another embodiment, the titer and/or yield of a malonyl-CoA derived compound produced by a cell that expresses the ACC variant is at least about 1 times, at least about 2 times, at least about 3 times, at least about 4 times, at least about 5 times, at least about 6 times, at least about 7 times, at least about 8 times, at least about 9 times, or at least about 10 times greater than that of a corresponding wild type cell. In one embodiment, the titer and/or yield of a malonyl-CoA derived compound produced by a cell expressing the ACC variant is at least about 1 percent, at least about 2 percent, at least about 3 percent, at least about 4 percent, at least about 5 percent, at least about 6 percent, at least about 7 percent, at least about 8 percent, at least about 9 percent, or about 10 percent greater than that of a corresponding wild type cell. In another embodiment, the titer and/or yield due to the expression of an ACC variant is at least about 20 percent to at least about 100 percent greater than that of the wild type ACC complex. In one embodiment, the titer and/or yield of a malonyl-CoA derived compound produced by a cell is at least about 20 percent, at least about 25 percent, at least about 30 percent, at least about 35 percent, at least about 40 percent, at least about 45 percent at least about 50 percent, at least about 55 percent, at least about 60 percent, at least about 65 percent, at least about 70 percent, at least about 75 percent, at least about 80 percent, at least about 85 percent, at least about 90 percent, at least about 95 percent, at least about 97 percent, at least about 98 percent, or at least about 100 percent greater than that of the corresponding wild type cell. In another embodiment, the titer and/or yield of a malonyl-CoA derived compound produced by a cell is at least about 200 percent, at least about 250 percent, at least about 300 percent, at least about 350 percent, at least about 400 percent, at least about 450 percent at least about 500 percent, at least about 550 percent, at least about 600 percent, at least about 610, 620, 630, 640 or 650 percent, at least about 700 percent, at least about 750 percent, at least about 800 percent, or at least about 850 percent greater than that of the corresponding wild type cell.

As used herein, the term "fatty acid biosynthetic pathway" means a biosynthetic pathway that produces fatty acid derivatives. The fatty acid biosynthetic pathway may include additional enzymes to produce fatty acid derivatives having desired characteristics.

As used herein, "fatty ester" means an ester having the formula RCOOR'. A fatty ester as referred to herein can be any ester made from a fatty acid, for example a fatty acid ester. In some embodiments, the R group is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty ester composition comprises one or more of a C6, C7, C8, C9, C10, C11, C12, C13, C14, C15, C16, C17, C18, C19, C20, C21, C22, C23, C24, C25, and a C26 fatty ester. In other embodiments, the fatty ester composition includes one or more of a C6, C7, C8, C9, C10, C11, C12, C13, C14, C15, C16, C17, and a C18 fatty ester. In still other embodiments, the fatty ester composition includes C12, C14, C16 and C18 fatty esters; C12, C14 and C16 fatty esters; C14, C16 and C18 fatty esters; or C12 and C14 fatty esters.

The R group of a fatty acid derivative, for example a fatty ester, can be a straight chain or a branched chain. Branched chains may have more than one point of branching and may include cyclic branches. In some embodiments, the branched fatty acid, branched fatty aldehyde, or branched fatty ester is a C6, C7, C8, C9, C10, C11, C12, C13, C14, C15, C16, C17, C18, C19, C20, C21, C22, C23, C24, C25, or a C26 branched fatty acid, branched fatty aldehyde, or branched fatty ester. In certain embodiments, the branched fatty acid, branched fatty aldehyde, or branched fatty ester is a C6, C7, C8, C9, C10, C11, C12, C13, C14, C15, C16, C17, or C18 branched fatty acid, or branched fatty ester. A fatty ester of the present disclosure may be referred to as containing an A side and a B side. As used herein, an "A side" of an ester refers to the carbon chain attached to the carboxylate oxygen of the ester. As used herein, a "B side" of an ester refers to the carbon chain comprising the parent carboxylate of the ester. When the fatty ester is derived from the fatty acid biosynthetic pathway, the A side is typically contributed by an alcohol, and the B side is contributed by a fatty acid.

Any alcohol can be used to form the A side of the fatty esters. For example, the alcohol can be derived from the fatty acid biosynthetic pathway, such as those describe herein. Alternatively, the alcohol can be produced through non-fatty acid biosynthetic pathways. Moreover, the alcohol can be provided exogenously. For example, the alcohol can be supplied in the fermentation broth in cases where the fatty ester is produced by an organism. Alternatively, a carboxylic acid, such as a fatty acid or acetic acid, can be supplied exogenously in instances where the fatty ester is produced by an organism that can also produce alcohol.

The carbon chains comprising the A side or B side of the ester can be of any length. In one embodiment, the A side of the ester is at least about 1, 2, 3, 4, 5, 6, 7, 8, 10, 12, 14, 16, or 18 carbons in length. When the fatty ester is a fatty acid methyl ester, the A side of the ester is 1 carbon in length. When the fatty ester is a fatty acid ethyl ester, the A side of the ester is 2 carbons in length. The B side of the ester can be at least about 4, 6, 8, 10, 12, 14, 16, 18, 20, 22, 24, or 26 carbons in length. The A side and/or the B side can be straight or branched chain. The branched chains can have one or more points of branching. In addition, the branched chains can include cyclic branches. Furthermore, the A side and/or B side can be saturated or unsaturated. If unsaturated, the A side and/or B side can have one or more points of unsaturation. In addition, the alcohol group of a fatty ester produced in accordance with the present disclosure need not be in the primary (C1) position. In one embodiment, the fatty ester is produced biosynthetically. In this embodiment, first the fatty acid is "activated." Non-limiting examples of "activated" fatty acids are acyl-CoA, acyl ACP, and acyl phosphate. Acyl-CoA can be a direct product of fatty acid biosynthesis or degradation. In addition, acyl-CoA can be synthesized from a free fatty acid, a CoA, and an adenosine nucleotide triphosphate (ATP). An example of an enzyme which produces acyl-CoA is acyl-CoA synthase.

In certain embodiments, the branched fatty acid derivative is an iso-fatty acid derivative, for example an iso-fatty ester, or an anteiso-fatty acid derivative, e.g., an anteiso-fatty ester. In exemplary embodiments, the branched fatty acid derivative is selected from iso-C7:0, iso-C8:0, iso-C9:0, iso-C10:0, iso-C11:0, iso-C12:0, iso-C13:0, iso-C14:0, iso-C15:0, iso-C16:0, iso-C17:0, iso-C18:0, iso-C19:0, anteiso-C7:0, anteiso-C8:0, anteiso-C9:0, anteiso-C10:0, anteiso-C11:0, anteiso-C12:0, anteiso-C13:0, anteiso-C14:0, anteiso-C15:0, anteiso-C16:0, anteiso-C17:0, anteiso-C18:0, and an anteiso-C19:0 branched fatty ester.

The R group of a branched or unbranched fatty acid derivative can be saturated or unsaturated. If unsaturated, the R group can have one or more than one point of unsaturation. In some embodiments, the unsaturated fatty acid derivative is a monounsaturated fatty acid derivative. In certain embodiments, the unsaturated fatty acid derivative is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or a C26:1 unsaturated fatty acid derivative. In certain embodiments, the unsaturated fatty acid derivative, is a C10:1, C12:1, C14:1, C16:1, or C18:1 unsaturated fatty acid derivative. In other embodiments, the unsaturated fatty acid derivative is unsaturated at the omega-7 position. In certain embodiments, the unsaturated fatty acid derivative comprises a cis double bond.

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen. "Culturing" or "cultivation" refers to growing a population of host cells (e.g., recombinant host cells) under suitable conditions in a liquid or solid medium. In certain embodiments, culturing refers to the fermentative bioconversion of a substrate to an endproduct. Culturing media are well known and individual components of such culture media are available from commercial sources, e.g., Difco™ media and BBL™ media. In one non-limiting example, the aqueous nutrient medium is a "rich medium" including complex sources of nitrogen, salts, and carbon, such as YP medium, comprising 10 g/L of peptone and 10 g/L yeast extract of such a medium.

As used herein, "modified" or an "altered level of" activity of a protein, for example an enzyme, in a recombinant host cell refers to a difference in one or more characteristics in the activity determined relative to the parent or native host cell. Typically, differences in activity are determined between a recombinant host cell, having modified activity, and the corresponding wild-type host cell (e.g., comparison of a culture of a recombinant host cell relative to the corresponding wild-type host cell). Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein, e.g., a variant ACC including a variant BCCP. In certain instances, the coding sequences for the polypeptides described herein are codon optimized for expression in a particular host cell. For example, for expression in E. coli, one or more codons can be optimized (Grosjean et al. (1982) Gene 18:199-209).

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons). As used herein, the phrase "the expression of said nucleotide sequence is modified relative to the wild type nucleotide sequence," means an increase or decrease in the level of expression and/or activity of an endogenous nucleotide sequence or the expression and/or activity of a heterologous or non-native polypeptide-encoding nucleotide sequence. The terms "altered level of expression" and "modified level of expression" are used interchangeably and mean that a polynucleotide, polypeptide, or hydrocarbon is present in a different concentration in an engineered host cell as compared to its concentration in a corresponding wild-type cell under the same conditions. As used herein, the term "express" with respect to a polynucleotide is to cause it to function. A polynucleotide which encodes a polypeptide (or protein) will, when expressed, be transcribed and translated to produce that polypeptide (or protein). As used herein, the term "overexpress" means to express or cause to be expressed a polynucleotide or polypeptide in a cell at a greater concentration than is normally expressed in a corresponding wildtype cell under the same conditions.

As used herein, the term "titer" refers to the quantity of a malonyl-CoA derived compound including a fatty acid derivative produced per unit volume of host cell culture. In any aspect of the compositions and methods described herein, a fatty acid derivative or other compound is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty acid derivative or other compound is produced at a titer of more than 100 g/L, more than 200 g/L, or more than 300 g/L. One preferred titer of fatty acid derivative or other compound produced by a recombinant host cell according to the methods of the disclosure is from 5 g/L to 200 g/L, 10 g/L to 150 g/L, 20 g/L to 120 g/L and 30 g/L to 100 g/L. The titer may refer to a particular fatty acid derivative or a combination of fatty acid derivatives or another compound or a combination of other compounds produced by a given recombinant host cell culture. For example, the expression of an ACC variant in a recombinant host cell such as E. coli results in the production of a higher titer as compared to a recombinant host cell expressing the corresponding wild type polypeptide. In one embodiment, the higher titer ranges from at least about 5 g/L to about 200 g/L.

As used herein, the "yield of a malonyl-CoA derived compound including fatty acid derivatives or other compounds produced by a host cell" refers to the efficiency by which an input carbon source is converted to product (i.e., a malonyl-CoA derived compound including a fatty acid derivative and/or other compounds) in a host cell. Host cells engineered to produce a malonyl-CoA derived compound including a fatty acid derivative according to the methods of the disclosure have a yield of at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% or a range bounded by any two of the foregoing values. In other embodiments, a fatty acid derivative or derivatives or other compound(s) are produced at a yield of more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%, more than 100%, more than 200%, more than 250%, more than 300%, more than 350%, more than 400%, more than 450%, more than 500%, more than 550%, more than 600%, more than 650%, more than 700%, more than 750%, or more. Alternatively, or in addition, the yield is about 30% or less, about 27% or less, about 25% or less, or about 22% or less. In another embodiment, the yield is about 50% or less, about 45% or less, or about 35% or less. In another embodiment, the yield is about 95% or less, or 90% or less, or 85% or less, or 80% or less, or 75% or less, or 70% or less, or 65% or less, or 60% or less, or 55% or less, or 50% or less. Thus, the yield can be bounded by any two of the above endpoints. For example, the yield of a malonyl-CoA derived compound including a fatty acid derivative or derivatives produced by the recombinant host cell according to the methods of the disclosure can be about 5% to about 15%, about 10% to about 25%, about 10% to about 22%, about 15% to about 27%, about 18% to about 22%, about 20% to about 28%, about 20% to about 30%, about 30% to about 40%, about 40% to about 50%, about 50% to about 60%, about 60% to about 70%, about 70% to about 80%, about 80% to about 90%, about 90% to about 100%, about 100% to about 200%, about 200% to about 300%, about 300% to about 400%, about 400% to about 500%, about 500% to about 600%, about 600% to about 700%, or about 700% to about 800%. The yield may refer to a particular malonyl-CoA derived compound including a fatty acid derivative or a combination of fatty acid derivatives or another compound or another combination of compounds produced by a given recombinant host cell culture. In one embodiment, the expression of a an ACC variant in a recombinant host cell such as E. coli results in the production of a higher yield of malonyl-CoA derived compounds including fatty acid derivatives such as, for example, fatty esters as compared to a host cell expressing the corresponding wild type polypeptide. In one embodiment, the higher yield ranges from about 10% to about 800% of theoretical yield.

As used herein, the term "productivity" refers to the quantity of a malonyl-CoA derived compound including a fatty acid derivative or derivatives or another compound or compounds produced per unit volume of host cell culture per unit time. In any aspect of the compositions and methods described herein, the productivity of a malonyl-CoA derived compound including a fatty acid derivative or derivatives or other compound or compounds produced by a recombinant host cell is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, 2500 mg/L/hour, or as high as 10 g/L/hour (dependent upon cell mass). For example, the productivity of a malonyl-CoA derived compound including a fatty acid derivative or derivatives or other compound(s) produced by a recombinant host cell according to the methods of the disclosure may be from 500 mg/L/hour to 2500 mg/L/hour, or from 700 mg/L/hour to 2000 mg/L/hour. The productivity may refer to a particular a malonyl-CoA derived compound including a fatty acid derivative or a combination of fatty acid derivatives or other compound(s) produced by a given host cell culture. For example, the expression of an ACC variant in a recombinant host cell such as E. coli results in the production of an increased productivity of malonyl-CoA derived compounds including fatty acid derivatives or other compounds as compared to a recombinant host cell expressing the corresponding wild type polypeptide. In one embodiment, the higher productivity ranges from about 0.3 g/L/h to about 3 g/L/h to about 10 g/L/h to about 100 g/L/h to about a 1000 g/L/h.

As used herein, the term "total fatty species" and "total fatty acid product" and "fatty acid derivative" may be used interchangeably herein with reference to the amount of fatty acid derivatives that can be produced by the host cell that expresses the ACC variant, as evaluated by GC-FID. The same terms may be used to mean, for example, fatty esters, fatty alcohols, fatty aldehydes, fatty amines, and free fatty acids when referring to a fatty acid derivative analysis.

As used herein, the term "glucose utilization rate" means the amount of glucose used by the culture per unit time, reported as grams/liter/hour (g/L/hr).

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain embodiments, the carbon source is biomass. In other embodiments, the carbon source is glucose. In other embodiments the carbon source is sucrose. In other embodiments the carbon source is glycerol. In other embodiments, the carbon source is a simple carbon source. In other embodiments, the carbon source is a renewable carbon source.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a composition comprising fatty esters. Fatty esters find utility in a number of products including, but not limited to, surfactants, polymers, films, textiles, dyes, pharmaceuticals, fragrances and flavoring agents, lacquers, paints, varnishes, softening agents in resins and plastics, plasticizers, flame retardants, and additives in gasoline and oil.

An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, glycerol, fermentation waste, ensilage, straw, lumber, sewage, garbage, cellulosic urban waste, and food leftovers (e.g., soaps, oils and fatty acids). The term "biomass" also can refer to sources of carbon, such as carbohydrates (e.g., monosaccharides, disaccharides, or polysaccharides).

As used herein, the term "isolated," with respect to products (such as fatty acid derivatives) refers to products that are separated from cellular components, cell culture media, or chemical or synthetic precursors. The fatty acid derivatives produced by the methods described herein can be relatively immiscible in the fermentation broth, as well as in the cytoplasm. Therefore, the fatty acid derivatives can collect in an organic phase either intracellularly or extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of malonyl-CoA derived compounds including fatty acid derivatives or other compounds in a sample. For example, when a malonyl-CoA derived compound including a fatty acid derivative or other compound is produced in a recombinant host cell, the malonyl-CoA derived compound including the fatty acid derivative or other compound can be purified by the removal of host cell proteins. After purification, the percentage of malonyl-CoA derived compounds including fatty acid derivatives or other compounds in the sample is increased. The terms "purify," "purified," and "purification" are relative terms which do not require absolute purity. Thus, for example, when a malonyl-CoA derived compound (including a fatty acid derivative or other compound) is produced in recombinant host cells, a malonyl-CoA derived compound (including a purified fatty acid derivative or other compound) is a malonyl-CoA derived compound (including a fatty acid derivative or other compound) that is substantially separated from other cellular components (e.g., nucleic acids, polypeptides, lipids, carbohydrates, or other hydrocarbons).

As used herein, the term "attenuate" means to weaken, reduce, or diminish. For example, a polypeptide can be attenuated by modifying the polypeptide to reduce its activity (e.g., by modifying a nucleotide sequence that encodes the polypeptide).

Acetyl-CoA Carboxylase (ACC) Variants

Fatty acid synthase (FAS) denotes a group of polypeptides that catalyze the initiation and elongation of acyl chains (Marrakchi et al. (2002) *Biochemical Society* 30:1050-1055). The acyl carrier protein (ACP) along with the enzymes in the FAS pathway control the length, degree of saturation and branching of the fatty acids produced. Enzymes that are included in the FAS pathway include, but are not limited to, ACC, FabD, FabH, FabG, FabA, FabZ, FabI, FabK, FabL, FabM, FabB, and FabF. Depending upon the desired product one or more of these genes can be optionally attenuated or over-expressed in a recombinant host cell (see, e.g., U.S. Pat. Nos. 8,658,404; 8,597,922; 8,535,916; 8,530,221; 8,372,610; 8,323,924; 8,313,934; 8,283,143; 8,268,599; 8,183,028; 8,110,670; 8,110,093; and 8,097,439).

The ACC enzyme (E.C. 6.4.1.2.) catalyzes the first committed step of fatty acid biosynthesis, the carboxylation of acetyl-CoA to malonyl-CoA. As such, it provides the malonyl-CoA substrate for the biosynthesis of fatty acids, fatty acid derivatives and other non-fatty acid compounds (see, e.g., FIG. 4). The ACC enzyme is found in most living organisms and presents as a multi-subunit enzyme in the majority of all prokaryotes and in the chloroplasts of most plants and algae. The prokaryotic ACC enzyme or ACC enzyme complex includes four different proteins encoded by four different genes (i.e., accA, accB, accC, and accD) that assemble into a complex at a fixed ratio (Broussard et al. (2013) supra). The genes accB and accC encode ACC subunits biotin carboxyl carrier protein (BCCP) and biotin carboxylase (BC), respectively. The present disclosure surprisingly shows that mutation(s) in only one or two of the ACC genes (e.g., accB, accC) is sufficient to increase the fatty acid flux and result in a higher titer and/or yield of malonyl-CoA derived compounds including fatty acid derivatives such as fatty acid methyl esters (FAME). The present disclosure shows that mutations in the coding region of the accB gene are beneficial, and that simultaneous expression changes of both accB and accC genes are also beneficial. In *E. coli*, the accB and accC genes are found adjacent in an operon in the chromosome. The ACC variants disclosed herein contain mutations or expression changes in one or two of the four ACC genes, which is sufficient to confer increased ACC enzymatic activity onto cells that already contain the other ACC subunit genes and polypeptides.

Thus, the present disclosure relates to, inter alia, ACC variants that result in a higher titer and/or higher yield of malonyl-CoA derived compounds when expressed in a cell; polypeptide sequences of such ACC variants and functional fragments thereof; polynucleotides encoding ACC variant polypeptide sequences; recombinant microorganisms including nucleic acids encoding ACC variant polypeptides; microorganisms capable of expressing ACC variant polypeptides; cultures of such microorganisms; processes for producing malonyl-CoA-derived compounds including fatty acid derivatives and non-fatty acid compounds; and the resultant compositions. Particularly, ACC variant polypeptides and microorganisms expressing these polypeptides as well as related methods are provided herein. Examples of ACC variants are BCCP variants as shown in Tables 1 and 3 (infra).

The *E. coli* wild-type nucleic acid sequence of accB is shown in SEQ ID NO: 1. The corresponding *E. coli* wild-type amino acid sequence for BCCP (encoded by accB of SEQ ID NO: 1) is shown in SEQ ID NO: 2. SEQ ID NO: 2 was used as a template to generate the improved ACC variant polypeptides in order to illustrate the disclosure (see Example 1, infra). A preferred ACC variant has at least about 50%, about 60%, about 70%, about 80%, about 90%, or about 99% sequence identity to the amino acid sequence of the wild type *E. coli* of SEQ ID NO: 2. The first amino acid after the ATG is designated amino acid "2".

In one aspect, the disclosure provides ACC variant polypeptides or ACC variants and nucleotide sequences that encode them. Various mutations in different amino acid positions (or residues) will increase production of various fatty acid derivatives such as, for example, fatty acid methyl ester (FAME) production. For example, techniques such as targeted site-saturation mutagenesis can be used to determine which positions and mutations provide the greatest improvement.

appreciate that increasing ester production is one way to test the variant ACC polypeptides for their ability to increase malonyl-CoA derived compounds such as, for example, fatty acid derivative production. Fatty ester production (rather than any other fatty acid derivative production such as, for example, fatty alcohol production or fatty aldehyde production or fatty acid production, etc.) was used for illustrative purposes only and is not meant to limit the present disclosure. One of skill will recognize that other compounds derived from malonyl-CoA can also be increased by following the teaching of the present disclosure and by employing the methods and protocols as disclosed herein and generally available to those of skill in the art.

TABLE 1 accB Variants with Increased FAME Production

| Well | Titer | Codon | Mutation | AminoAcid Change | Mutant Number | Nucleic Acid SEQ ID NO: | Amino Acid SEQ ID NO: |
|---|---|---|---|---|---|---|---|
| C12 | 630% | CAC | D2H | Histidine (H) | 1 | SEQ ID NO: 3 | SEQ ID NO: 4 |
| C01 | 578% | AAC | D2N | Asparagine (N) | 2 | SEQ ID NO: 5 | SEQ ID NO: 6 |
| F07 | 527% | CAT | D2H | Histidine (H) | 3 | SEQ ID NO: 7 | SEQ ID NO: 8 |
| E05 | 475% | ATT | D2I | Isoleucine (I) | 4 | SEQ ID NO: 9 | SEQ ID NO: 10 |
| F08 | 420% | ATT | D2I | Isoleucine (I) | 5 | SEQ ID NO: 11 | SEQ ID NO: 12 |
| F06 | 331% | ACT | D2T | Threonine (T) | 6 | SEQ ID NO: 13 | SEQ ID NO: 14 |
| B01 | 305% | TCT | D2S | Serine (S) | 7 | SEQ ID NO: 15 | SEQ ID NO: 16 |
| E12 | 282% | AGC | D2S | Serine (S) | 8 | SEQ ID NO: 17 | SEQ ID NO: 18 |
| C06 | 276% | CGA | D2R | Arginine (R) | 9 | SEQ ID NO: 19 | SEQ ID NO: 20 |
| F10 | 276% | TCT | D2S | Serine (S) | 10 | SEQ ID NO: 21 | SEQ ID NO: 22 |
| B05 | 265% | TAT | D2Y | Tyrosine (Y) | 11 | SEQ ID NO: 23 | SEQ ID NO: 24 |
| B08 | 260% | TCA | D2S | Serine (S) | 12 | SEQ ID NO: 25 | SEQ ID NO: 26 |
| C04 | 255% | TAC | D2Y | Tyrosine (Y) | 13 | SEQ ID NO: 27 | SEQ ID NO: 28 |
| G05 | 254% | TAC | D2Y | Tyrosine (Y) | 14 | SEQ ID NO: 29 | SEQ ID NO: 30 |
| E08 | 239% | CTT | D2L | Leucine (L) | 15 | SEQ ID NO: 31 | SEQ ID NO: 32 |
| E02 | 234% | CGA | D2R | Arginine (R) | 16 | SEQ ID NO: 33 | SEQ ID NO: 34 |
| H12 | 225% | TTG | D2L | Leucine (L) | 17 | SEQ ID NO: 35 | SEQ ID NO: 36 |
| B03 | 223% | CGA | D2R | Arginine (R) | 18 | SEQ ID NO: 37 | SEQ ID NO: 38 |
| A10 | 219% | ACG | D2T | Threonine (T) | 19 | SEQ ID NO: 39 | SEQ ID NO: 40 |
| B02 | 217% | TAT | D2Y | Tyrosine (Y) | 20 | SEQ ID NO: 41 | SEQ ID NO: 42 |
| F03 | 214% | CTT | D2L | Leucine (L) | 21 | SEQ ID NO: 43 | SEQ ID NO: 44 |
| G04 | 214% | TTA | D2L | Leucine (L) | 22 | SEQ ID NO: 45 | SEQ ID NO: 46 |
| H10 | 214% | CAG | D2Q | Glutamine (Q) | 23 | SEQ ID NO: 47 | SEQ ID NO: 48 |
| F12 | 212% | TAT | D2Y | Tyrosine (Y) | 24 | SEQ ID NO: 49 | SEQ ID NO: 50 |
| G03 | 206% | TTA | D2L | Leucine (L) | 25 | SEQ ID NO: 51 | SEQ ID NO: 52 |
| B07 | 204% | TTA | D2L | Leucine (L) | 26 | SEQ ID NO: 53 | SEQ ID NO: 54 |
| B10 | 202% | TTA | D2L | Leucine (L) | 27 | SEQ ID NO: 55 | SEQ ID NO: 56 |
| C07 | 193% | TTA | D2L | Leucine (L) | 28 | SEQ ID NO: 57 | SEQ ID NO: 58 |
| H05 | 177% | TTG | D2L | Leucine (L) | 29 | SEQ ID NO: 59 | SEQ ID NO: 60 |
| F11 | 172% | TTG | D2L | Leucine (L) | 30 | SEQ ID NO: 61 | SEQ ID NO: 62 |
| F04 | 168% | CTT | D2L | Leucine (L) | 31 | SEQ ID NO: 63 | SEQ ID NO: 64 |
| E06 | 146% | ATC | D2I | Isoleucine (I) | 32 | SEQ ID NO: 65 | SEQ ID NO: 66 |
| E03 | 145% | TAT | D2Y | Tyrosine (Y) | 33 | SEQ ID NO: 67 | SEQ ID NO: 68 |
| G07 | 144% | GAA | D2E | Glutamate (E) | 34 | SEQ ID NO: 69 | SEQ ID NO: 70 |
| A08 | 142% | CTC | D2L | Leucine (L) | 35 | SEQ ID NO: 71 | SEQ ID NO: 72 |
| H07 | 130% | CTC | D2L | Leucine (L) | 36 | SEQ ID NO: 73 | SEQ ID NO: 74 |
| A12 | 129% | CTC | D2L | Leucine (L) | 37 | SEQ ID NO: 75 | SEQ ID NO: 76 |
| A01 | 126% | ATC | D2I | Isoleucine (I) | 38 | SEQ ID NO: 77 | SEQ ID NO: 78 |
| G06 | 126% | GAA | D2E | Glutamate (E) | 39 | SEQ ID NO: 79 | SEQ ID NO: 80 |
| H02 | 116% | TCG | D2S | Serine (S) | 40 | SEQ ID NO: 81 | SEQ ID NO: 82 |
| H06 | 114% | TCG | D2S | Serine (S) | 41 | SEQ ID NO: 83 | SEQ ID NO: 84 |
| H08 | 114% | TCG | D2S | Serine (S) | 42 | SEQ ID NO: 85 | SEQ ID NO: 86 |
| A11 | 107% | TCG | D2S | Serine (S) | 43 | SEQ ID NO: 87 | SEQ ID NO: 88 |
| E01 | 106% | TCG | D2S | Serine (S) | 44 | SEQ ID NO: 89 | SEQ ID NO: 90 |

The wild type accB gene contains a GAT codon at position 2 encoding aspartic acid or aspartate (Asp, D). In one embodiment, it can be seen that mutations in the amino acid position 2 within the wild-type accB gene of SEQ ID NO: 2 improved FAME production. These variant ACC polypeptides (i.e., encoded by the mutant accB gene) are capable of increasing the production of fatty esters relative to wild-type ACC. Table 1 below depicts a summary of the best variants for accB position 2. The skilled artisan will Depending upon the position mutated, single or multiple amino acid changes at specified positions give rise to increases in fatty acid derivative production as well as increases in the production of non-fatty acid compounds. In one embodiment, a single or multiple amino acid change results in an increase in fatty acid production. In another embodiment, a single or multiple amino acid change results in an increase in fatty ester production, including but not limited to, fatty acid methyl ester (FAME) and/or fatty acid ethyl ester (FAEE). In another embodiment, a single or multiple amino acid change results in an increase in fatty aldehye production. In another embodiment, a single or multiple amino acid change results in an increase in fatty alcohol production. In another embodiment, a single or multiple amino acid change results in an increase in fatty amine production. In another embodiment, a single or multiple amino acid change results in an increase in hydrocarbon production. In another embodiment, a single or multiple amino acid change results in an increase in alkane production. In another embodiment, a single or multiple amino acid change results in an increase in alkene or olefin production. In still another embodiment, a single or multiple amino acid change results in an increase in bifunctional fatty acid production, including but not limited to, hydroxy fatty acids and/or diacids. In yet another embodiment, a single or multiple amino acid change results in an increase in bifunctional fatty alcohol production. In still another embodiment, a single or multiple amino acid change results in an increase in bifunctional fatty ester and/or fatty amine production. In another embodiment, a single or multiple amino acid change results in an increase in the production of beta-hydroxy fatty acid derived compounds. In another embodiment, a single or multiple amino acid change results in an increase in the production of unsaturated fatty acid derived compounds. In still another embodiment, a single or multiple amino acid change results in an increase in the production of flavanones and/or flavonoids. In another embodiment, a single or multiple amino acid change results in an increase in the production of polyketides. In another embodiment, a single or multiple amino acid change results in an increase in the production of 3-hydroxypropionic acid (3-HP). In another embodiment, a single or multiple amino acid change results in an increase in the production of malonic acid or malonate.

Thus, combinations of one or more amino acid changes at specified positions may give rise to increases in fatty acid derivative and/or free fatty acid production and/or non-fatty acid based compounds such as flavanones and/or flavonoids, polyketides, malonate, 3-hydroxypropionic acid (3-HP), and others. The effect of each individual amino acid change on fatty acid derivative production may or may not be additive to the effect of other individual amino acid changes on fatty acid derivative production or the production of non-fatty acid compounds. In some embodiments, a combination of one or more amino acid changes at specified positions results in an increase in fatty acid derivative production. Accordingly, one or multiple amino acid changes at specified positions can give rise to increases in fatty acid derivative production. Similarly, one or multiple amino acid changes at specified positions can give rise to increases in non-fatty acid compounds.

In addition to the ACC variants show in Table 1 above, an error prone library of the accB gene was built and screened using SEQ ID NO: 1 as a template. Additional accB variants were identified by introducing single or multiple mutations (see Example 1, Table 3, infra). Thus, 63 beneficial mutations (see Tables 1 and 3) were identified in the coding region of accB that resulted in an increased titer of FAME. Notably, a high number of mutations were found in the N-terminal amino acid region that ranges from about amino acid position 1 to about position 60.

In one aspect, the disclosure relates to ACC variant polypeptides with at least about 50% sequence identity to SEQ ID NO: 2. In some embodiments, a variant ACC polypeptide shows at least about 50%, (e.g., about 48% to about 52%), at least about 60%, at least about 70%, at least about 75%, at least 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least 99% sequence identity to the wild-type ACC sequence of SEQ ID NO: 2 and also includes one or more substitutions which result in useful characteristics and/or properties as described herein. In one aspect of the disclosure, the ACC variant polypeptide with improved characteristics has about 100% sequence identity to SEQ ID NO: 6. In another aspect of the disclosure, the ACC variant polypeptide has about 100% sequence identity to any one of the following SEQ ID NOS, including, but not limited to, SEQ ID NO: 4, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90.

In a related aspect, an ACC variant polypeptide is encoded by a nucleotide sequence having 100% sequence identity to SEQ ID NO: 5. In another related aspect, an ACC variant polypeptide is encoded by a nucleotide sequence having about 100% sequence identity to any one of the following SEQ ID NOS including, but not limited to, SEQ ID NO: 3, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, and SEQ ID NO: 89.

In another aspect, the disclosure relates to ACC variant polypeptides with improved ACC activity with at least about 50% sequence identity to SEQ ID NO: 6. In some embodiments, an ACC variant polypeptide has at least about 50%, (e.g., about 48% to about 52%), at least about 60%, at least about 70%, at least about 75%, at least 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least 99% sequence identity to the ACC variant sequence of SEQ ID NO: 6 and also includes one or more substitutions which results in improved characteristics and/or properties as described herein. In another aspect, the disclosure relates to ACC variant polypeptides with at least about 50% sequence identity to any one of the following SEQ ID NOS including, but not limited to, SEQ ID NO: 4, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90. In some embodiments, an ACC variant polypeptide has at least about 50%, (e.g., about 48% to about 52%), at least about 60%, at least about 70%, at least about 75%, at least 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least 99% sequence identity to the ACC sequence of any one of the following SEQ ID NOS including, but not limited to, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90, which encompass one or more substitutions that result in improved characteristics and/or properties as described herein.

In another aspect, the disclosure relates to ACC variant polypeptides that include an amino acid sequence encoded by a nucleic acid sequence that has at least about 70%, at least about 75%, at least 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least 99% sequence identity to the ACC variant sequence of SEQ ID NO: 5. In some embodiments the nucleic acid sequence encodes an ACC variant with one or more substitutions which results in improved characteristics and/or properties as described herein. In other embodiments, the variant ACC nucleic acid sequence is derived from an organism such as *E. coli*. In another aspect, the disclosure relates to ACC variant polypeptides that include an amino acid sequence encoded by a nucleic acid sequence that has at least about 70%, at least about 75%, at least 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least 99% sequence identity to the ACC variant sequence of any one of the following SEQ ID NOS including, but not limited to, SEQ ID NO: 3, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, and SEQ ID NO: 89. In some embodiments the nucleic acid sequence encodes an ACC variant with one or more substitutions which results in improved characteristics and/or properties as described herein. In other embodiments, the ACC variant nucleic acid sequence is derived from an organism such as *E. coli*.

In another aspect, the disclosure relates to ACC variant polypeptides that include an amino acid sequence encoded by a nucleic acid that hybridizes under stringent conditions over substantially the entire length of a nucleic acid corresponding to any one of the following SEQ ID NOS including, but not limited to, SEQ ID NO:3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, and SEQ ID NO: 89. In some embodiments the nucleic acid sequence encodes an ACC variant nucleic acid sequence derived from an organism such as *E. coli*. In a related aspect, the disclosure provides ACC variants encoded by a nucleotide sequence having at least about 70%, at least about 75%, at least 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least 99% sequence identity to SEQ ID NO: 1 and comprises one or more of the substitutions disclosed herein.

The present disclosure shows that mutations in the coding region of the accB gene alone are beneficial (supra) while simultaneous expression changes of both accB and accC genes are also beneficial. In *E. coli*, the accB and accC genes are found adjacent in an operon in the chromosome. Thus, an expression library of the accBC operon was built and screened for variants that showed improvement in the ACC activity (i.e., measured by the increased production of malonyl-CoA derived compounds in a cell) over the wild type accBC promoter. Table 2 (supra) depicts a summary of the best variants based on an accBC T5 promoter sequence as shown below (underlined regions indicate −35 and −10 positions of the promoters):

E. coli wild-type accBC promoter (PaccBC) region nucleotide sequence (SEQ ID NO: 91):

TTGTTGCAAATTACACGGTGTTGAAGGTTATTTACATGTTAGCTG<u>TTGA</u>
<u>TTAT</u>CTTCCCTGATAAGAC<u>CAGTAT</u>TTAGCT

Bacteriophage T5 promoter (PT5) nucleotide sequence (SEQ ID NO: 92):

AATCATAAAAAATTTAT<u>TTGCTTT</u>CAGGAAAATTTTTCTG<u>TATAATAG</u>
ATTC

TABLE 2 accBC T5 Promoter Variants with Increased FAME Production

| Well | Titer | accBC T5 Promoter Sequence | SEQ ID NO: |
|---|---|---|---|
| G06 | 315% | AATCATAAAAAATTTATTTGCTCTCAG GAAAATTTTTCTGGATAATAGATTC | 93 |
| E09 | 292% | AATCATAAAAAATTTATCTTCTCTCAG GAAAATTTTTCTGTATTATAGATTC | 94 |
| F06 | 226% | AATCATAAAAAATTTATCTGCCTTCAG GAAAATTTTTCTGTATAATAGATTC | 95 |
| B11 | 219% | AATCATAAAAAATTTATTTGCCTTCAG GAAAATTTTTCTGTATAGTAGATTC | 96 |

The library can be built using primers that replace the native accBC promoter region with any suitable promoter library (e.g., hybrid promoter, artificial or synthetic promoter, promoter from different organism, promoter from different gene in same organism, commercial promoter, etc.), which usually contains degenerate nucleotides to introduce random mutations. In certain embodiments, the promoter is a developmentally-regulated, an organelle-specific, a tissue-specific, an inducible, a constitutive, or a cell-specific promoter. All suitable promoters are contemplated herein. In other embodiments, expression changes to the accBC operon can be made using numerous techniques known to those of skill in the art, including, but not limited to, replacement of the promoter with a different E. coli promoter or heterologous promoter, mutation of the native promoter, mutations in the ribosome binding sites (RBS) of accB and accC separately or together, alteration of the untranslated region (UTR) between the accBC promoter and the accB gene, duplication of the accBC operon in the chromosome or on a plasmid, replacement of the chromosomal accBC operon with a plasmid-encoded operon, engineering of the transcription factors which bind the accBC promoter region. In one exemplary embodiment, a bacteriophage T5 promoter is used. In one embodiment, the promoter library can be joined to appropriate homology regions using a PCR technique, and the library can then be integrated into the bacterial chromosome (see Example 2), replacing the native accBC promoter. The expression library can be screened as shown in Example 2 (infra).

Improved Properties of ACC Variants

The wild type BCCP (SEQ ID NOS: 1 and 2) was genetically altered via mutagenesis to produce a high percentage of malonyl-CoA derived compounds such as FAME without the need to overexpress any other gene using expression in E. coli as an illustrative model (see Example 1, infra). The same was accomplished by genetically altering the accBC operon (see Example 2, infra). Thus, when expressed in a recombinant host cell such as E. coli, variants of the wild type BCCP result in a higher titer and yield of the desired product, i.e., they produce greater amounts of malonyl-CoA derived compounds such as fatty acid derivatives when expressed in a host cell (i.e., a recombinant cell) compared to the wild type host cell (that does not express the ACC variant). The wild type ACC is a native protein complex and it normally requires all four proteins for its activity, including, biotin carboxylase (BC), biotin carboxyl carrier protein (BCCP), and two proteins that form the carboxyltransferase (CT). However, the variant BCCPs of the present disclosure appear to confer onto the cell the ability to increase the production of malonyl-CoA derived compounds. Without wishing to be bound by theory, it is contemplated that this may be a direct consequence of the variant BCCPs directly or indirectly conferring increased ACC activity in cells that express native ACC. For example, the BCCP variant polypeptides produced from about 100% to about 650% FAME when expressed in host cells (see Table 1, supra, and Table 3, infra) compared to the wild type cells. This means that the observed titer of FAME ranged from up to 650% of the FAME titer normally produced by the wild type cell. In another example, changes in the accBC operon lead to variant BCCP polypeptides that produced from about 200% to about 350% FAME titer when expressed in host cells (see Table 2, supra) compared to wild type cells.

In one embodiment, the ACC variant polypeptides are expected to produce increased amounts of fatty acid derivatives including, but not limited to, fatty esters such as fatty acid methyl esters (FAME) and fatty acid ethyl esters (FAEE), fatty amines, fatty aldehydes, fatty alcohols, short and long chain alcohols, hydrocarbons, ketones, alkanes, terminal olefins, internal olefins, beta hydroxy fatty acid derivatives, bifunctional fatty acid derivatives, and unsaturated fatty acid derivatives compared to the wild type ACC enzyme. In another embodiment, the ACC variant polypeptides are expected to produce increased amounts of non-fatty acid based compounds (e.g., flavanones and flavonoids, polyketides, 3-hydroxypropionic acid, malonate, etc.) compared to the wild type ACC enzyme. One of skill will recognize that the end products that can be produced through the ACC variants encompass several classes of compounds including fatty acid derivatives and non-fatty acid compounds, depending on the various biochemical pathways that are influenced by the upregulation of malonyl-CoA. FIG. 4 provides non-exhaustive examples of possible compounds.

Methods of Making ACC Variants

In practicing the methods of the present disclosure, mutagenesis is used to prepare groups of recombinant host cells for screening. Typically, the recombinant host cells comprise one or more polynucleotide sequences that include an open reading frame for an ACC variant polypeptide, such as a variant accB gene together with operably-linked regulatory sequences and/or an accB gene with operably-linked variant accBC promoter(s). Numerous examples of variant ACC polypeptides including variant BCCP polypeptides useful in the practice of the methods of the present disclosure are described herein. Examples of regulatory sequences useful in the practice of the methods of the present disclosure are also described herein. Mutagenesis of such polynucleotide sequences can be performed using genetic engineering techniques, such as site directed mutagenesis, random chemical mutagenesis, exonuclease III deletion procedures, or standard cloning techniques. Alternatively, mutations in polynucleotide sequences can be created using chemical synthesis or modification procedures. Those of ordinary skill in the art will recognize that the protocols and procedures employed herein can be modified and that such modifications are in accordance with the variations of the disclosure. For example, when method steps are described in a certain order, the ordering of steps can be modified and/or performed in parallel or sequentially.

Mutagenesis methods are well known in the art and include, for example, the following. In error prone PCR (Leung et al. (1989) *Technique* 1:11-15; and Caldwell et al. (1992) *PCR Methods Applic.* 2:28-33), PCR is performed under conditions where the copying fidelity of the DNA polymerase is low, such that a high rate of point mutations is obtained along the entire length of the PCR product. Briefly, in such procedures, polynucleotides to be mutagenized are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min., 45° C. for 1 min., and 72° C. for 1 min. It will be appreciated that these parameters can be varied as appropriate. The mutagenized polynucleotides are then cloned into an appropriate vector and the activities of the affected polypeptides encoded by the mutagenized polynucleotides are evaluated. Mutagenesis can also be performed using oligonucleotide directed mutagenesis (Reidhaar-Olson et al. (1988) *Science* 241:53-57) to generate site-specific mutations in any cloned DNA of interest. Briefly, in such procedures a plurality of double stranded oligonucleotides bearing one or more mutations to be introduced into the cloned DNA are synthesized and assembled into the cloned DNA to be mutagenized. Clones containing the mutagenized DNA are recovered, and the activities of affected polypeptides are assessed. Another mutagenesis method for generating polynucleotide sequence variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408. Still another mutagenesis method of generating polynucleotide sequence variants is sexual PCR mutagenesis (Stemmer (1994) *PNAS, USA* 91:10747-10751). In sexual PCR mutagenesis, forced homologous recombination occurs between DNA molecules of different, but highly related, DNA sequence in vitro as a result of random fragmentation of the DNA molecule based on sequence homology. This is followed by fixation of the crossover by primer extension in a PCR reaction.

ACC variants can also be created by in vivo mutagenesis. In some embodiments, random mutations in a nucleic acid sequence are generated by propagating the polynucleotide sequence in a bacterial strain, such as an *E. coli* strain, which carries mutations in one or more of the DNA repair pathways. Such "mutator" strains have a higher random mutation rate than that of a wild-type strain. Propagating a DNA sequence in one of these strains will eventually generate random mutations within the DNA. Mutator strains suitable for use for in vivo mutagenesis are described in, for example, PCT International Publication No. WO 91/16427.

ACC variants can also be generated using cassette mutagenesis. In cassette mutagenesis, a small region of a double stranded DNA molecule is replaced with a synthetic oligonucleotide "cassette" that differs from the starting polynucleotide sequence. The oligonucleotide often contains completely and/or partially randomized versions of the starting polynucleotide sequence. There are many applications of cassette mutagenesis; for example, preparing mutant proteins by cassette mutagenesis (Richards, J. H. (1986) *Nature* 323:187; Ecker et al. (1987) *J. Biol. Chem.* 262: 3524-3527); codon cassette mutagenesis to insert or replace individual codons (Kegler-Ebo et al. (1994) *Nucleic Acids Res.* 22(9):1593-1599); preparing variant polynucleotide sequences by randomization of non-coding polynucleotide sequences comprising regulatory sequences (e.g., ribosome binding sites, see, e.g., Barrick et al. (1994) *Nucleic Acids Res.* 22(7):1287-1295); Wilson et al. (1994) *Biotechniques* 17:944-953).

Recursive ensemble mutagenesis (Arkin et al. (1992) *PNAS, USA* 89:7811-7815) can also be used to generate polynucleotide sequence variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Exponential ensemble mutagenesis (Delegrave et al. (1993) *Biotech. Res.* 11:1548-1552) can also be used to generate polynucleotide sequence variants of ACC. Exponential ensemble mutagenesis is a process for generating combinatorial libraries with a high percentage of unique and functional mutants, wherein small groups of residues are randomized in parallel to identify, at each altered position, amino acids which lead to functional proteins. Random and site-directed mutagenesis can also be used (Arnold (1993) *Curr. Opin. Biotech.* 4:450-455).

Further, standard methods of in vivo mutagenesis can be used. For example, host cells, comprising one or more polynucleotide sequences that include an open reading frame for an ACC polypeptide, as well as operably-linked regulatory sequences, can be subject to mutagenesis via exposure to radiation (e.g., UV light or X-rays) or exposure to chemicals (e.g., ethylating agents, alkylating agents, or nucleic acid analogs). In some host cell types, for example, bacteria, yeast, and plants, transposable elements can also be used for in vivo mutagenesis.

The mutagenesis of one or more polynucleotide sequences that encode an ACC related polypeptide generally results in expression of an ACC polypeptide product that demonstrates a modified and improved biological function. For example, the mutagenesis of one or more polynucleotide sequences that include an accB generally results in expression of a BCCP polypeptide product that demonstrates a modified and improved biological function such as enhanced ACC activity. When preparing a group of recombinant microorganisms by mutagenesis of one or more polynucleotide sequences including the open reading frame encoding a BCCP and operably-linked regulatory sequences, the protein expressed from the resulting mutagenized polynucleotide sequences will show increased ACC biological function, Thus, an improved yield of malonyl-CoA derived compounds such as fatty acid derivatives or other compounds, and/or improved compositions thereof including a modified mixture of fatty acid derivatives or other compounds (in terms of chain length, saturation, and the like) is observed upon culture of the recombinant microorganism under conditions effective to express the mutant accB polynucleotide.

Hot Spots

The disclosure is also based, at least in part, on the identification of certain structurally conserved "hot spots" among variant ACC polypeptides including variant BCCP polypeptides. Hot spots are regions where a high number of mutations are observed that lead to a higher titer of fatty acid derivatives such as FAME or a higher titer of non-fatty acid compounds. Notably, such regions are seen in variant BCCP polypeptides, i.e., hot spots are observed in the N-terminal amino acid region ranging from amino acid position 1 to about amino acid position 60 (e.g., showing the highest number of mutations).

Motifs

The disclosure is also based, at least in part, on the identification of certain structurally conserved motifs among variant ACC polypeptides including variant BCCP polypeptides. Biotin protein ligase (EC 6.3.4.15), also known as holocarboxylase synthetase, catalyzes the covalent attachment of the biotin prosthetic group to a specific lysine of the BCCP subunit of ACC. BCCP-type proteins have a conserved motif at the site of biotin attachment. The motif includes K (lysine), which is the biotinylated lysine residue. BCCP polypeptides of various bacterial species have this conserved motif, suggesting that any mutations in that region could result in a decreased function. The consensus sequence for the motif is shown below, where K is the biotinylated lysine:

(L/I/V)E(A/V)MK(M/L)

FIG. 2 shows an alignment of a section of BCCP amino acid sequences from seven different bacterial species, including *Escherichia coli* (SEQ ID NO: 97 (partial); SEQ ID NO: 2 (full); Accession Number NP_417721), *Lactobacillus brevis* (SEQ ID NO: 98 (partial); SEQ ID NO: 104 (full); Accession Number WP_011667655), *Stenotrophomonas maltophilia* (SEQ ID NO: 99 (partial); SEQ ID NO: 105 (full); Accession Number AIL09846), *Pseudomonas putida* (SEQ ID NO: 100 (partial); SEQ ID NO: 106 (full); Accession Number AE016246_3), *Bacillius subtilis* (SEQ ID NO: 101 (partial); SEQ ID NO: 107 (full); Accession Number NP_390315), *Corynebacterium glutamicum* (SEQ ID NO: 102 (partial); SEQ ID NO: 108 (full); Accession Number WP_011013826), and *Saccharomyces cerevisiae* (SEQ ID NO: 103 (partial); SEQ ID NO: 109 (full); Accession Number AAA20073). The motif is conserved across all seven species (see boxed region on FIG. 2) regardless of an overall amino acid sequence identity that ranges from about 10% percent to about 66% percent. For example, BCCP from *Lactobacillus brevis* showed a 28% identity when compared to *Escherichia coli*. BCCP from *Stenotrophomonas maltophilia* showed a 55% identity when compared to *Escherichia coli*. BCCP from *Pseudomonas putida* showed a 66% identity when compared to *Escherichia coli*. BCCP from *Bacillius subtilis* showed a 40% identity when compared to *Escherichia coli*. BCCP from *Corynebacterium glutamicum* and *Saccharomyces cerevisiae* showed a 10% identity when compared to *Escherichia coli*. This confirms that even in divergent species the motif is conserved. However, in some instances, BCCP polypeptides have a high amino acid sequence identity across various species, ranging from about 85% identity to about 100% identity. For example, BCCP from *Escherichia alberti* is about 98% identical to *Escherichia coli*; BCCP from *Shigella flexneri* is about 93% identical to *Escherichia coli*; and *Klebsiella pneumonia* is about 85% identical to *Escherichia coli*.

Host Cells and Host Cell Cultures

Figure 3:
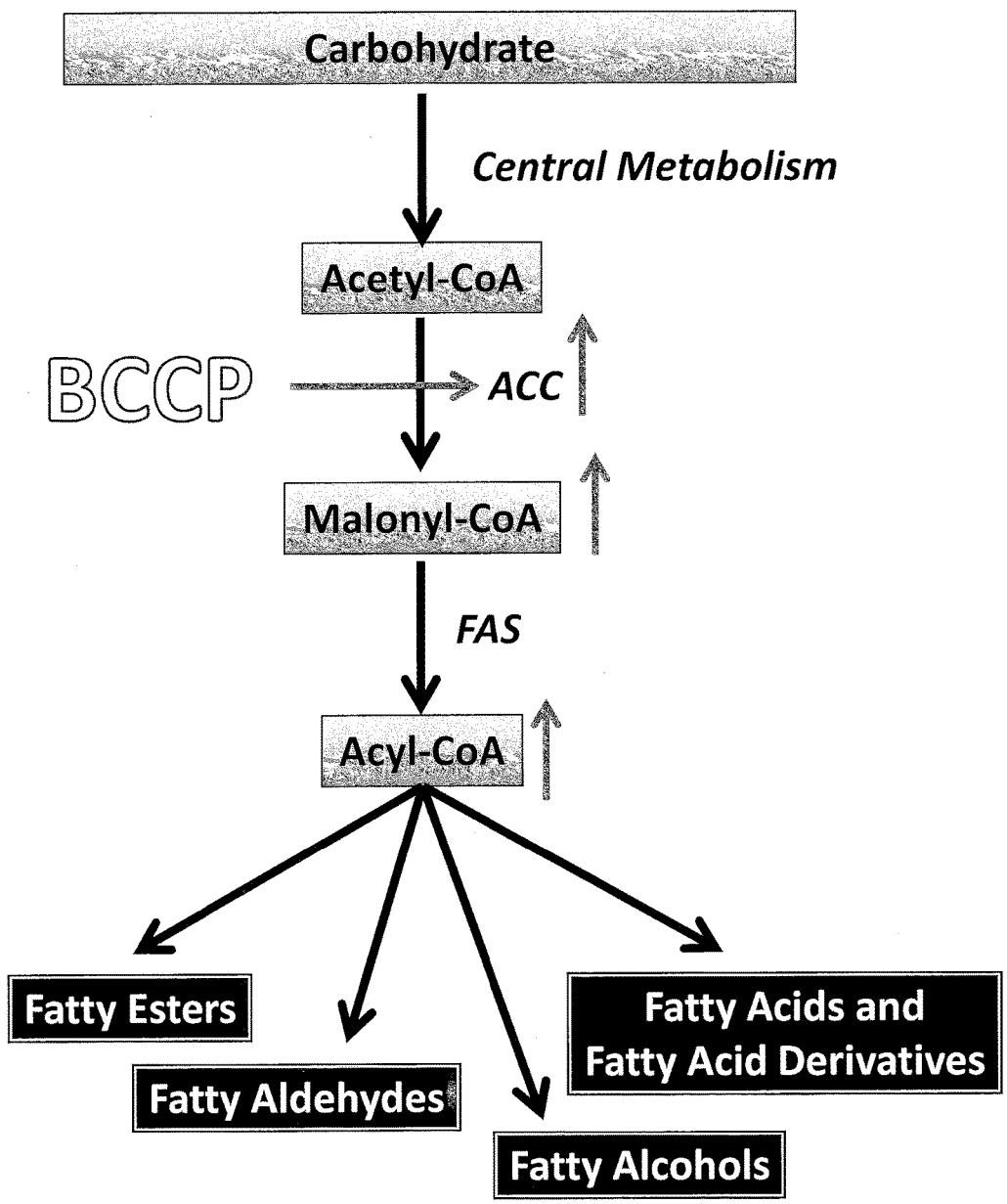
FIG. 3 is a schematic of another embodiment of an engineered biochemical pathway that involves acetyl-CoA carboxylase (ACC) variants such as a variant biotin carboxyl carrier protein (BCCP). As depicted, BCCP may confer improved acetyl-CoA carboxylase (ACC) activity when expressed in a cell. This may lead to increased production of malonyl-CoA and acyl-CoA, which in turn may lead to increased production of malonyl-CoA-derived compounds, including, for example, fatty acid derivatives such as fatty esters, fatty aldehydes, fatty alcohols, fatty acids, and other fatty acid derivatives.

It should be appreciated, in view of the present disclosure, that any of the embodiments contemplated herein may be practiced with any host cell or microorganism that can be genetically modified via the introduction of one or more nucleic acid sequences that code for one or more ACC variants. As such, the recombinant microorganisms of the disclosure function as host cells and encompass one or more polynucleotide sequences that include an open reading frame encoding a variant ACC polypeptide conferring improved/increased ACC activity and/or improved/increased production of a malonyl-CoA derived compound, together with operably-linked regulatory sequences that facilitate expression of the ACC polypeptide in the host cell. In one embodiment, the polypeptide conferring improved/increased ACC activity and/or improved/increased production of a malonyl-CoA derived compound is a variant or mutant of BCCP. In another embodiment, the polypeptide conferring improved/increased ACC activity and/or improved/increased production of a malonyl-CoA derived compound is an improved BCCP or other improved ACC polypeptide or combination thereof resulting from expression changes in the accBC operon. In a recombinant host cell of the disclosure, the open reading frame coding sequences and/or the regulatory sequences may be modified relative to the corresponding wild-type coding sequence of the BCCP polypeptide. A fatty acid derivative composition is produced by culturing a host cell that expresses an ACC variant (i.e., a recombinant host cell) in the presence of a carbon source under conditions effective to express the variant ACC polypeptide including the variant BCCP (see FIGS. 1 and 3). Expression of mutant or variant ACC polypeptides results in production of fatty acid derivative compositions with increased yields of fatty acids, fatty esters, fatty alcohols, fatty amines, fatty aldehydes, bifunctional fatty acid derivatives, diacids, hydrocarbons, ketones, alkanes, alkenes or olefins, and/or the like. In one embodiment, expression of mutant or variant ACC polypeptides such as variant BCCP polypeptides results in the increased yield of fatty ester compositions including FAME and/or FAEE. A non-fatty acid compound is produced by culturing a host cell that expresses an ACC variant (i.e., a recombinant host cell) in the presence of a carbon source under conditions effective to express the variant ACC polypeptide including the variant BCCP (see FIG. 4). Expression of mutant or variant ACC polypeptides results in production of non-fatty acid compounds with increased yields including polyketides, flavanones, flavonoids, 3-hydroxypropionic acid (3-HP), malonate, and others (see FIG. 4).

The host cells or microorganisms of the disclosure include host strains or host cells that are genetically engineered to contain genetic alterations in order to test the efficiency of specific mutations on enzymatic activities (i.e., recombinant cells or microorganisms). Various optional genetic manipulations and alterations can be used interchangeably from one host cell to another, depending on what native enzymatic pathways are present in the original host cell. In one embodiment, a host strain can be used for testing the ACC variants. A host strain may encompasses a number of genetic alterations in order to test specific variables and culture environments, including but not limited to, culture conditions including fermentation components, carbon source (e.g., feedstock), temperature, pressure, reduced culture contamination conditions, and oxygen levels.

In one embodiment, a host strain called BD64 is used. BD64 is based on *E. coli* strain MG1655 that encompasses an optional fadE and fhuA deletion. Acyl-CoA dehydrogenase (FadE) is an enzyme that is important for metabolizing fatty acids. It catalyzes the second step in fatty acid utilization (beta-oxidation), which is the process of breaking long chains of fatty acids (acyl-CoAs) into acetyl-CoA molecules. More specifically, the second step of the β-oxidation cycle of fatty acid degradation in bacteria is the oxidation of acyl-CoA to 2-enoyl-CoA, which is catalyzed by FadE. When *E. coli* lacks FadE, it cannot grow on fatty acids as a carbon source but it can grow on acetate. The inability to utilize fatty acids of any chain length is consistent with the reported phenotype of fadE strains, i.e., fadE mutant strains where FadE function is disrupted. The fadE gene can be optionally knocked out or attenuated to assure that acyl-CoAs, which are intermediates in this pathway, can accumulate in the cell such that all acyl-CoAs can be efficiently converted to fatty esters by ester synthase. However, fadE attenuation is optional when sugar is used as a carbon source since under such condition expression of FadE is likely repressed and FadE therefore may only be present in small amounts and not able to efficiently compete with ester synthase for acyl-CoA substrates. FadE is repressed due to catabolite repression. *E. coli* and many other microbes prefer to consume sugar over fatty acids, so when both sources are available sugar is consumed first by repressing the fad regulon (see D. Clark, *J Bacteriol*. (1981) 148(2):521-6)). Moreover, the absence of sugars induces FadE expression. Acyl-CoA intermediates could be lost to the beta oxidation pathway since the proteins expressed by the fad regulon (including FadE) are up-regulated and will efficiently compete for acyl-CoAs. Thus, it can be beneficial to have the fadE gene knocked out or attenuated. Since many carbon sources are sugar based, it is optional to attenuate FadE. The gene fhuA codes for the TonA protein, which is an energy-coupled transporter and receptor in the outer membrane of *E. coli* (V. Braun (2009) *J Bacteriol*. 191(11): 3431-3436). Its deletion is optional. The fhuA deletion allows the cell to become more resistant to phage attack which can be beneficial in certain fermentation conditions. Thus, it may be desirable to delete fhuA in a host cell that is likely subject to potential contamination during fermentation runs.

The host strain BD64 (supra) also encompasses optional overexpression of one or more of the following genes: fadR from *Escherichia coli*, fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). The overexpression of one or more of these genes, which code for enzymes and regulators in fatty acid biosynthesis, can serve to further increase the titer of fatty-acid derivative compounds under various culture conditions.

In another embodiment, the wild-type *E. coli* strains MG1655 or W3110 are used as exemplary host cells for the production of fatty acid derivatives. Similarly, these host cells provide optional overexpression of one or more biosynthesis genes (i.e., genes coding for enzymes and regulators of fatty acid biosynthesis) that can increase the titer of fatty-acid derivative compounds under various culture conditions. Genetic alterations include fadR from *Escherichia coli*, fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156).

In some embodiments, the host cells or microorganisms that are used to express the variant ACC polypeptides will further express genes that encompass certain enzymatic activities that can increase the production to one or more particular fatty acid derivative(s) such as fatty esters, fatty alcohols, fatty amines, fatty aldehydes, bifunctional fatty acid derivatives, diacids, and the like (see FIGS. 1 and 3) as well as alkanes, alkenes or olefins, and ketones. In one embodiment, the host cell has thioesterase activity (E.C. 3.1.2.* or E.C. 3.1. 2.14 or E.C. 3.1.1.5) for the production of fatty acids which can be increased by overexpressing the gene. In another embodiment, the host cell has ester synthase activity (E.C. 2.3.1.75) for the production of fatty esters. In another embodiment, the host cell has acyl-ACP reductase (AAR) (E.C. 1.2.1.80) activity and/or alcohol dehydrogenase activity (E.C. 1.1.1.1.) and/or fatty alcohol acyl-CoA reductase (FAR) (E.C. 1.1.1.*) activity and/or carboxylic acid reductase (CAR) (EC 1.2.99.6) activity for the production of fatty alcohols. In another embodiment, the host cell has acyl-ACP reductase (AAR) (E.C. 1.2.1.80) activity for the production of fatty aldehydes. In another embodiment, the host cell has acyl-ACP reductase (AAR) (E.C. 1.2.1.80) activity and decarbonylase activity for the production of alkanes and alkenes. In another embodiment, the host cell has acyl-CoA reductase (E.C. 1.2.1.50) activity, acyl-CoA synthase (FadD) (E.C. 2.3.1.86) activity, and thioesterase (E.C. 3.1.2.* or E.C. 3.1. 2.14 or E.C. 3.1.1.5) activity for the production of fatty alcohols. In another embodiment, the host cell has ester synthase activity (E.C. 2.3.1.75), acyl-CoA synthase (FadD) (E.C. 2.3.1.86) activity, and thioesterase (E.C. 3.1.2.* or E.C. 3.1. 2.14 or E.C. 3.1.1.5) activity for the production of fatty esters. In another embodiment, the host cell has OleA activity for the production of ketones. In another embodiment, the host cell has OleBCD activity for the production of internal olefins. In another embodiment, the host cell has has acyl-ACP reductase (AAR) (E.C. 1.2.1.80) activity and alcohol dehydrogenase activity (E.C. 1.1.1.1.) for the production of fatty alcohols. In another embodiment, the host cell has thioesterase (E.C. 3.1.2.* or E.C. 3.1. 2.14 or E.C. 3.1.1.5) activity and decarboxylase activity for making terminal olefins. The expression of enzymatic activities in microorganisms and microbial cells is taught by U.S. Pat. Nos. 8,097,439; 8,110,093; 8,110,670; 8,183,028; 8,268,599; 8,283,143; 8,232,924; 8,372,610; and 8,530,221, which are incorporated herein by reference.

In other embodiments, the host cells or microorganisms that are used to express the variant ACC polypeptides will include certain native enzyme activities that are upregulated or overexpressed in order to produce one or more particular fatty acid derivative(s) such as fatty esters, fatty alcohols, fatty amines, fatty aldehydes, bifunctional fatty acid derivatives, diacids and the like (see FIG. 1). In one embodiment, the host cell has a native thioesterase (E.C. 3.1.2.* or E.C. 3.1. 2.14 or E.C. 3.1.1.5) activity for the production of fatty acids which can be increased by overexpressing the thioesterase gene.

The present disclosure includes host strains or microorganisms that express variant ACC polypeptide sequences including variant BCCP polypeptide sequences. Examples of variant BCCP polypeptide sequences that when expressed in a host cell result in a higher titer of fatty acid derivatives including fatty esters include but are not limited to, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO:

32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90.

The recombinant host cell may produce a fatty ester, such as a fatty acid methyl ester (FAME) or a fatty acid ethyl ester (FAEE), a fatty alcohol, a fatty amine, a fatty aldehyde, a bifunctional fatty acid derivative, a diacids, an alkane, an olefin, a hydrocarbon, or the like; or a non-fatty acid compound such as a flavanone, a flavonoid, a polyketide, malonate, or 3-hydroxypropioic acid. The fatty acid derivatives or other compounds are typically recovered from the culture medium and/or are isolated from the host cells. In one embodiment, the fatty acid derivatives or other compounds are recovered from the culture medium (extracellular). In another embodiment, the fatty acid derivatives or other compounds are isolated from the host cells (intracellular). In another embodiment, the fatty acid derivatives or other compounds are recovered from the culture medium and isolated from the host cells. The fatty acid derivative composition produced by a host cell can be analyzed using methods known in the art, for example, GC-FID, in order to determine the distribution of particular fatty acid derivatives as well as chain lengths and degree of saturation of the components of the fatty acid derivative composition. Similarly, other compounds can be analyzed through methods well known in the art.

Examples of host cells that function as microorganisms, include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* or *Streptomyces*. In some embodiments, the host cell is a Gram-positive bacterial cell. In other embodiments, the host cell is a Gram-negative bacterial cell. In some embodiments, the host cell is an *E. coli* cell. In other embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In still other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In yet other embodiments, the host cell is a *Streptomyces lividans* cell or a *Streptomyces murinus* cell. In yet other embodiments, the host cell is an *Actinomycetes* cell. In some embodiments, the host cell is a *Saccharomyces cerevisiae* cell.

In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell has autotrophic activity.

In some embodiments, the host cell has photoautotrophic activity, such as in the presence of light. In some embodiments, the host cell is heterotrophic or mixotrophic in the absence of light. In certain embodiments, the host cell is a cell from *Arabidopsis thaliana, Panicum virgatum, Miscanthus giganteus, Zea mays, Botryococcuse braunii, Chlamydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridium thermocellum, Penicillium chrysogenum, Pichia pastoris, Saccharomyces cerevisiae, Schizosaccharomyces pombe, Pseudomonas fluorescens,* or *Zymomonas mobilis*.

In one embodiment, the microbial cell is from a cyanobacteria including, but not limited to, *Prochlorococcus, Synechococcus, Synechocystis, Cyanothece,* and *Nostoc punctiforme*. In another embodiment, the microbial cell is from a specific cyanobacterial species including, but not limited to, *Synechococcus elongatus* PCC7942, *Synechocystis* sp. PCC6803, and *Synechococcus* sp. PCC7001.

Methods of Making Recombinant Host Cells and Cultures

Various methods well known in the art can be used to engineer host cells to produce fatty acid derivatives and/or fatty acid derivative compositions or other compounds. The methods can include the use of vectors, preferably expression vectors, comprising a nucleic acid encoding a mutant or variant ACC including a mutant or variant BCCP, as described herein. Those skilled in the art will appreciate a variety of viral and non-viral vectors can be used in the methods described herein.

In some embodiments of the present disclosure, a higher titer of a compound such as a fatty acid ester in a particular composition is a higher titer of a particular type of fatty acid ester or a combination of fatty acid esters produced by a recombinant host cell culture relative to the titer of the same fatty acid ester or combination of fatty acid esters produced by a control culture of a corresponding wild-type host cell. In other embodiments, other fatty acid derivatives or non-fatty acid compounds are produced by the recombinant host cell culture in a similar fashion. In some embodiments, a mutant or variant ACC polynucleotide (or gene) sequence including a mutant or variant accB polynucleotide (or gene) sequence is provided to the host cell by way of a recombinant vector, which comprises a promoter operably linked to the polynucleotide sequence. In certain embodiments, the promoter is a developmentally-regulated, an organelle-specific, a tissue-specific, an inducible, a constitutive, or a cell-specific promoter. The recombinant vector typically comprises at least one sequence selected from an expression control sequence operatively coupled to the polynucleotide sequence; a selection marker operatively coupled to the polynucleotide sequence; a marker sequence operatively coupled to the polynucleotide sequence; a purification moiety operatively coupled to the polynucleotide sequence; a secretion sequence operatively coupled to the polynucleotide sequence; and a targeting sequence operatively coupled to the polynucleotide sequence. The polynucleotide sequences, comprising open reading frames encoding proteins and operably-linked regulatory sequences can be integrated into a chromosome of the recombinant host cells, incorporated in one or more plasmid expression system resident in the recombinant host cells, or both.

The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, E. coli, is most often carried out with vectors containing constitutive or inducible promoters directing the expression of either fusion or non-fusion polypeptides. Suitable expression systems for both prokaryotic and eukaryotic cells are well known in the art; see, e.g., Sambrook et al., "Molecular Cloning: A Laboratory Manual," second edition, Cold Spring Harbor Laboratory, (1989). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra).

For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug.

Culture and Fermentation of Recombinant Host Cells

As used herein, the term "fermentation" broadly refers to the conversion of organic materials into target substances by host cells, for example, the conversion of a carbon source by recombinant host cells into fatty acids or derivatives thereof by propagating a culture of the recombinant host cells in a media comprising the carbon source. As used herein, the term "conditions permissive for the production" means any conditions that allow a host cell to produce a desired product, such as a malonyl-CoA derived compound including fatty acid derivatives and other non-fatty acid compounds. Similarly, the term "conditions in which the polynucleotide sequence of a vector is expressed" means any conditions that allow a host cell to synthesize a polypeptide. Suitable conditions include, for example, fermentation conditions. Fermentation conditions can include many parameters, including but not limited to temperature ranges, levels of aeration, feed rates and media composition. Each of these conditions, individually and in combination, allows the host cell to grow. Fermentation can be aerobic, anaerobic, or variations thereof (such as micro-aerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source.

For small scale production, the engineered host cells can be grown in batches of, for example, about 100 µL, 200 µL, 300 µL, 400 µL, 500 µL, 1 mL, 5 mL, 10 mL, 15 mL, 25 mL, 50 mL, 75 mL, 100 mL, 500 mL, 1 L, 2 L, 5 L, or 10 L; fermented; and induced to express a desired polynucleotide sequence, such as a polynucleotide sequence encoding an ACC variant polypeptide. For large scale production, the engineered host cells can be grown in cultures having a volume batches of about 10 L, 100 L, 1000 L, 10,000 L, 100,000 L, 1,000,000 L or larger; fermented; and induced to express a desired polynucleotide sequence. The fatty acid derivative compositions or other compounds described herein may be found in the extracellular environment of the recombinant host cell culture and can be readily isolated from the culture medium. A fatty acid derivative may be secreted by the recombinant host cell, transported into the extracellular environment or passively transferred into the extracellular environment of the recombinant host cell culture. In one embodiment, a fatty ester composition may be isolated from a recombinant host cell culture using routine methods known in the art. Any non-fatty acid compounds may be produced extracellularly or intracellularly.

Screening Recombinant Host Cells

In one embodiment of the present disclosure, the activity of a mutant or variant ACC polypeptide is determined by culturing recombinant host cells (comprising one or more mutagenized or variant ACC polynucleotide sequences), followed by screening to identify characteristics of, for example, fatty acid derivative compositions or other compounds produced by the recombinant host cells; for example, titer, yield and productivity of fatty acid derivatives or other compounds. In another embodiment, the activity of a mutant or variant ACC polypeptide is determined by culturing recombinant host cells (comprising one or more mutagenized or variant ACC polynucleotide sequences), followed by screening to identify characteristics of, for example, fatty acid derivate compositions (e.g., fatty esters, fatty alcohols, fatty aldehydes, etc.) or other compounds produced by the recombinant host cells; for example: titer, yield and productivity of fatty acid derivatives or other compounds. Mutant or variant ACC polypeptides or mutant or variant BCCP polypeptides and fragments thereof can be assayed for improved ACC activity and/or improved/increased production of a malonyl-CoA derived compound using routine methods. For example, a mutant or variant ACC polypeptide or BCCP polypeptide or fragment thereof is contacted with a substrate (e.g., an acyl-CoA, an acyl-ACP, a free fatty acid, an alcohol) under conditions that allow the polypeptide to function. In one embodiment, a decrease in the level of the substrate or an increase in the level of a fatty ester or a fatty ester composition can be measured to determine the ACC activity. The same applies to the production of fatty alcohols, fatty aldehydes, fatty amines and other fatty acid derivatives as well as other compounds.

Products Derived from Recombinant Host Cells

As used herein, "fraction of modem carbon" or fM has the same meaning as defined by National Institute of Standards and Technology (NIST) Standard Reference Materials (SRMs 4990B and 4990C, known as oxalic acids standards HOxI and HOxII, respectively. The fundamental definition relates to 0.95 times the 14C/12C isotope ratio HOxI (referenced to AD 1950). This is roughly equivalent to decay-corrected pre-Industrial Revolution wood. For the current living biosphere (plant material), fM is approximately 1.1.

Bioproducts (e.g., the fatty acid derivative compositions or non-fatty acid compositions produced in accordance with the present disclosure) including biologically produced organic compounds, and in particular, the fatty ester compositions produced using the fatty acid biosynthetic pathways described herein, have been produced from renewable carbon sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588). The ability to distinguish bioproducts from petroleum based organic compounds is beneficial in tracking these materials in commerce. For example, organic compounds or chemicals comprising both biologically based and petroleum based carbon isotope profiles may be distinguished from organic compounds and chemicals made only of petroleum based materials. Hence, the bioproducts herein can be followed or tracked in commerce on the basis of their unique carbon isotope profile. Bioproducts can be distinguished from petroleum based organic compounds by comparing the stable carbon isotope ratio ($^{13}C/^{12}C$) in each sample. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in $^{13}C/^{12}C$ and the corresponding $\delta^{13}C$ values. Both C4 and C3 plants exhibit a range of $^{13}C/^{12}C$ isotopic ratios, but typical values are about −7 to about −13 per mil for C4 plants and about −19 to about −27 per mil for C3 plants (see, e.g., Stuiver et al., Radiocarbon 19:355 (1977)). Coal and petroleum fall generally in this latter range.

$$\delta^{13}C(‰)=[(^{13}C/^{12}C)sample-(^{13}C/^{12}C)standard]/(^{13}C/^{12}C)standard\times 1000$$

A series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46. The compositions described herein include fatty ester compositions and products produced by any of the methods described herein. Specifically, fatty ester composition or product can have a $\delta^{13}C$ of about −28 or greater, about −27 or greater, −20 or greater, −18 or greater, −15 or greater, −13 or greater, −10 or greater, or −8 or greater. For example, the fatty ester composition or product can have a $\delta^{13}C$ of about −30 to about −15, about −27 to about −19, about −25 to about −21, about −15 to about −5, about −13 to about −7, or about −13 to about −10. In other instances, the fatty ester composition or product t can have a $\delta^{13}C$ of about −10, −11, −12, or −12.3. Fatty ester compositions and products produced in accordance with the disclosure herein can also be distinguished from petroleum based organic compounds by comparing the amount of $^{14}C$ in each compound. Because $^{14}C$ has a nuclear half-life of 5730 years, petroleum based fuels containing "older" carbon can be distinguished from fatty ester compositions and bioproducts which contain "newer" carbon (see, e.g., Currie, "Source Apportionment of Atmospheric Particles", Characterization of Environmental Particles, J. Buffle and H. P. van Leeuwen, Eds., 1 of Vol. I of the IUPAC Environmental Analytical Chemistry Series (Lewis Publishers, Inc.) 3-74, (1992)).

The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about 1.2×10-12, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" (fM). The fatty ester compositions and products described herein include bioproducts that can have an fM $^{14}C$ of at least about 1. For example, the bioproduct of the disclosure can have an fM $^{14}C$ of at least about 1.01, an fM $^{14}C$ of about 1 to about 1.5, an fM $^{14}C$ of about 1.04 to about 1.18, or an fM $^{14}C$ of about 1.111 to about 1.124.

Another measurement of $^{14}C$ is known as the percent of modern carbon (pMC). For an archaeologist or geologist using $^{14}C$ dates, AD 1950 equals "zero years old". This also represents 100 pMC. "Bomb carbon" in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning "100%" equal to 107.5 pMC and "0%" equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty esters as described herein can have a pMC of at least about 50, 60, 70, 75, 80, 85, 90, 95, 96, 97, 98, 99, or 100. In other instances, a fatty ester composition described herein can have a pMC of between about 50 and about 100; about 60 and about 100; about 70 and about 100; about 80 and about 100; about 85 and about 100; about 87 and about 98; or about 90 and about 95. In yet other instances, a fatty ester composition described herein can have a pMC of about 90, 91, 92, 93, 94, or 94.2.

Fatty Ester Compositions

Examples of fatty esters include fatty acid esters, such as those derived from short-chain alcohols, including FAEE and FAME, and those derived from longer chain fatty alcohols. The fatty esters and/or fatty ester compositions that are produced can be used, individually or in suitable combinations, as a biofuel (e.g., a biodiesel), an industrial chemical, or a component of, or feedstock for, a biofuel or an industrial chemical. In some aspects, the disclosure pertains to a method of producing a fatty ester composition comprising one or more fatty acid esters, including, for example, FAEE, FAME and/or other fatty acid ester derivatives of longer chain alcohols. In related aspects, the method comprises a genetically engineered production host suitable for making fatty esters and fatty ester compositions including, but not limited to, FAME, FAEE, fatty acid propyl esters, fatty acid isopropyl esters, fatty acid butyl esters, monoglycerides, fatty acid isobutyl esters, fatty acid 2-butyl esters, and fatty acid tert-butyl esters, and the like.

Esters have many commercial uses. For example, biodiesel, an alternative fuel, is comprised of esters (e.g., fatty acid methyl ester, fatty acid ethyl esters, etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plastics, plasticizers, flame retardants, and additives in gasoline and oil. In addition, esters can be used in the manufacture of polymers, films, textiles, dyes, and pharmaceuticals.

In general, the fatty ester or fatty ester composition is isolated from the extracellular environment of the host cell. In some embodiments, the fatty ester or fatty ester composition is spontaneously secreted, partially or completely, from the host cell. In alternative embodiments, the fatty ester or fatty ester composition is transported into the extracellular environment, optionally with the aid of one or more transport proteins. In still other embodiments, the fatty ester or fatty ester composition is passively transported into the extracellular environment.

Fatty Alcohol Compositions

Examples of fatty alcohols include saturated-, unsaturated-, straight-chain- and branched-chain fatty alcohols. The fatty alcohols and/or fatty alcohol compositions that are produced can be used, individually or in suitable combinations, as a detergent, an industrial chemical, or a component of, or feedstock for, an industrial chemical. In some aspects, the disclosure pertains to a method of producing a fatty alcohol composition comprising one or more fatty alcohols, including, for example, shorter and longer chain fatty alcohols. In related aspects, the method comprises a production host suitable for making fatty alcohols and fatty alcohol compositions.

The methods can produce fatty alcohols comprising a C6-C26 fatty alcohol. In some embodiments, the fatty alcohol includes a C6, C7, C8, C9, C10, C11, C12, C13, C14, C15, C16, C17, C18, C19, C20, C21, C22, C23, C24, C25, and/or a C26 fatty alcohol. In certain embodiments, the fatty alcohol is 1-decanol, 1-dodecanol, 1-myristyl alcohol, 1-hexadecanol, octadecenol, tetradecenol, or hexadecenol. In other embodiments, the fatty alcohol includes a straight-chain fatty alcohol. In other embodiments, the fatty alcohol includes a branched-chain fatty alcohol. In yet other embodiments, the fatty alcohol comprises a cyclic moiety. In some embodiments, the fatty alcohol is an unsaturated fatty alcohol. In other embodiments, the fatty alcohol is a monounsaturated fatty alcohol. In yet other embodiments, the fatty alcohol is a saturated fatty alcohol. In another aspect, the invention features a fatty alcohol produced by any of the methods or any of the microorganisms described herein, or a surfactant encompassing a fatty alcohol produced by any of the methods or any of the microorganisms described herein. In some embodiments, the fatty alcohol has a $\delta^{13}C$ of about −15.4 or greater. In certain embodiments, the fatty alcohol has a $\delta^{13}C$ of about −15.4 to about −10.9, or of about −13.92 to about −13.84. In some embodiments, the fatty alcohol has an $f_M{}^{14}C$ of at least about 1.003. In certain embodiments, the fatty alcohol has an $f_M{}^{14}C$ of at least about 1.01 or at least about 1.5. In some embodiments, the fatty alcohol has an $f_M{}^{14}C$ of about 1.111 to about 1.124.

Fatty alcohols have many commercial uses. The shorter chain fatty alcohols are used in the cosmetic and food industries as emulsifiers, emollients, and thickeners. Due to their amphiphilic nature, fatty alcohols behave as nonionic surfactants, which are useful as detergents. In addition, fatty alcohols are used in waxes, gums, resins, pharmaceutical lotions, lubricating oil additives, textile antistatic and finishing agents, plasticizers, cosmetics, industrial solvents, and solvents for fats.

In general, the fatty alcohol or fatty alcohol composition is isolated from the extracellular environment of the host cell. In some embodiments, the fatty alcohol or fatty alcohol composition is spontaneously secreted, partially or completely, from the host cell. In alternative embodiments, the fatty alcohol or fatty alchol composition is transported into the extracellular environment, optionally with the aid of one or more transport proteins. In still other embodiments, the fatty alcohol or fatty alcohol composition is passively transported into the extracellular environment.

EXAMPLES

The following specific examples are intended to illustrate the disclosure and should not be construed as limiting the scope of the claims.

In order to illustrate the present findings, two different methods were developed to improve the native *E. coli* ACC enzyme for improved FAME production, i.e., achieve a higher titer and yield. Although it has been known in the literature that increased expression of all four *E. coli* ACC genes can improve fatty acid production, it was surprising to find that targeted mutations in the accB gene and targeted expression changes in the accBC operon can improve FAME production.

Protocols:

1. Strain Construction for accBC

A production host strain called BD64 (supra) was used to express accBC. The production host strain contained several genetic manipulations in order to test for expression of accBC. The chromosome region containing the accBC operon was modified. The genetic manipulation was performed in the presence of an ACC complementation system. Malonate was supplemented at 10 mM and simultaneously two malonate utilization genes matB and matC from *Rhizobium trifolii* were expressed from a low copy plasmid. These genes were cloned behind a constitutive promoter in the pKD46 integration plasmid using standard manipulation techniques. The accBC operon was knocked out (see Datsenko et al. (2000) *Proceedings of the National Academy of*

Sciences 97(12):6640-6645) except that selective plates contained 10 mM malonate. The modified accBC operon was integrated using the same procedure except selective plates lacked malonate.

2. Strain Construction for accB

A production host strain called BD64 (supra) was used to express accB. The chromosome region containing the accB gene was modified using the same strategy used for the construction of accBC (supra).

3. ACC FAME Production Assay

Changes to the *E. coli* ACC enzymatic activity were assayed using a FAME production system. Strain BD64 (supra) containing the desired ACC mutation(s) was transformed with an ester synthase (ES) plasmid called pKEV13. Plasmid pKEV13 was constructed by cloning the commercial pTrc promoter (Life Technologies) and an ester synthase gene from *Marinobacter hydrocarbonoclasticus* ATCC 49840 into the plasmid pCL1920 (Lerner et al. (1990) *Nucleic acids research* 18(15):4631.) Strains were fermented, extracted, and FAME production measured according to standard procedures, which are detailed below.

The fermentation was performed as follows; from an LB culture growing in 96 well plates 30 μL LB culture was used to inoculate 270 μL FA2P media, which was then incubated for approximately 16 hours at 32° C. in a shaking incubator. 30 μL of the overnight seed was used to inoculate 300 μL FA4P media containing 2% methanol and 1 mM IPTG. Both FA2P and FA4P media are modified M9 minimal media containing 0.2 g/L or 0.4 g/L (respectively) of phosphate. The carbon source in both FA2P and FA4P media is 50 g/L glucose. The cultures were incubated at 32° C. in a shaking incubator for 24 hours, when they were extracted following the standard extraction protocol detailed below.

The extraction was performed as follows; to each well to be extracted 40 μL 1M HCl, then 300 μL butyl acetate with 500 mg/L C11-FAME as internal standard was added. The 96 well plate was heat-sealed using a plate sealer (ALPS-300; Abgene, ThermoScientific, Rockford, Ill.), and shaken for 15 minutes at 2000 rpm using MixMate (Eppendorf, Hamburg, Germany). After shaking, the plate was centrifuged for 10 minutes at 4500 rpm at room temperature (Allegra X-15R, rotor SX4750A, Beckman Coulter, Brea, Calif.) to separate the aqueous and organic layers. 50 μL of the organic layer was transferred to a 96 well plate (96-well plate, polypropylene, Corning, Amsterdam, The Netherlands). The plate was heat sealed and then stored at −20° C. until it was evaluated by gas chromatography flame ionization detector (GC-FID).

Extraction and FAME quantification were performed as follows; 1 uL of sample was injected onto a UFM column (cat #: UFMC00001010401, Thermo Fisher Scientific, Waltham, Mass.) in a Trace GC Ultra (Thermo Fisher Scientific, Waltham, Mass.) with a flame ionization detector (FID). The instrument was set up to detect C8 to C18 FAME and quantify C12 to C18 β-OH FAME.

Example 1

Mutations in accB Increase FAME Production

An error prone library of the accB gene was built and screened for variants that showed improvement over the wild type gene. Table 3 below depicts a summary of the best variants. The error-prone library of the accB gene was build using a commercially available kit (Genemorph II, Agilent Technologies). The accB gene was joined to appropriate homology regions using the SOE PCR technique, and the library was integrated into the *E. coli* chromosome as described in Protocol 1, replacing the native *E. coli* accB gene. The error-prone library was screened according to Protocol 2.

TABLE 3

Variants of accB for FAME Production

| Well | Titer | Mutations |
| --- | --- | --- |
| 5A02 | 435% | D2Y(TAT) K108I(ATA) |
| 6A08 | 171% | I10T(ACC) |
| 2H09 | 155% | I10T(ACC) |
| 1G11 | 151% | I117T(ACC) P151P(CCA) |
| 4B03 | 142% | M44T(ACG) R84S(AGT) |
| 2G03 | 135% | I82N(AAC) K100N(AAC) |
| 6E05 | 129% | G26D(GAC) A76P(CCG) |
| 4H09 | 129% | R31C(GAC) I3I(ATA) |
| 3A03 | 128% | R31C(GAC) I3I(ATA) |
| 5E06 | 127% | A76V(GTG) |
| 5G03 | 126% | E14G(GGA) P56S(TCA) P51P(CCT) |
| 1A09 | 126% | I10T(ACC) |
| 6E01 | 121% | I78F(TTC) |
| 6F03 | 118% | V140L(CTC) A61A(GCT) |
| 4G09 | 113% | E14G(GGA) P56S(TCA) P51P(CCT) |
| 5A12 | 111% | K136I(ATA) E11E(GAA) |
| 5F05 | 111% | F41L (CTC) |
| 5C07 | 110% | A76V(GTG) |
| 5G08 | 109% | M52V(GTG) E128D(GAC) E71E(GAG) |
| 6H11 | 108% | S142C(TGT) |
| 5C10 | 107% | A49S(TCT) T94A(GCC) M124L(TTG) T134I(ATC) A63A(GCC) A75A(GCG) P86P(CCA) |

The columns of Table 3 indicate the original well location of the variant, the FAME titer improvement over the control, and the amino acid and DNA codon changes in each variant. The results in Table 3 suggested that a mutation in amino acid position 2 may achieve the greatest increase in titer. Well 5A02 showed an increase in titer of 435% of normal ACC activity.

Figure 5:
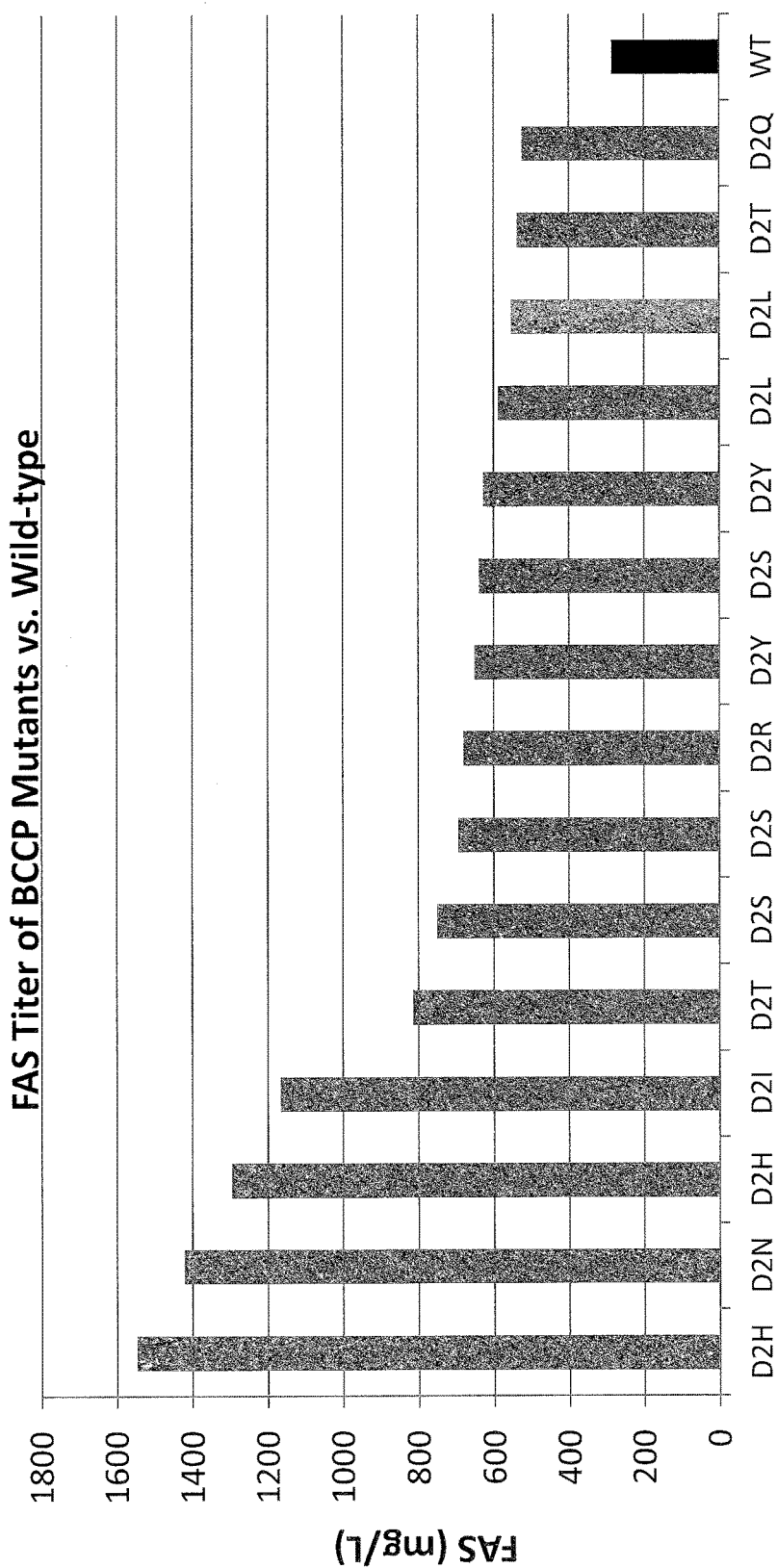
FIG. 5 shows a graph that depicts the FAS titer (FAME) as a result of expressing various BCCP variants (at position 2 of the accB gene) in E. coli host cells. WT is the control for the wild-type ACC complex. Some of these BCCP variants improved FAS titer over 5-fold. (see also Table 1).

Next, targeted site-saturation mutagenesis was carried out in order to determine which individual positions and mutations provide the greatest improvement. It was determined that indeed mutations in position 2 (directly following the start codon) of accB provide the greatest increases in FAME titer. The wild type accB contains a GAT codon at position 2 encoding aspartic acid (Asp, D). Table 1 (supra) depicts a summary of the best variants for accB position 2. The site-saturation library was build using oligonucleotide primers containing degenerate bases NNN at the second accB position. The accB gene was joined to appropriate homology regions, using the SOE PCR technique, and the library was integrated into the *E. coli* chromosome as described in Protocol 1, replacing the native *E. coli* accB gene. The error-prone library was screened according to Protocol 2. As can be seen in Table 1 (supra), an increase in titer of up to 630% of normal ACC activity was observed in the mutant D2H. FIG. 5 further reflects these findings and presents a graph that shows the FAS titer in mg/L. More specifically, the figure depicts the FAS titer (FAME) as a result of expressing various BCCP variants (at position 2 of the accB gene) in *E. coli* host cells. WT is the control for the wild-type ACC complex. Some of these BCCP variants improved FAS titer over 5-fold (see also Table 1). This finding was surprising since BCCP variants outperformed the entire ACC complex in producing fatty acid derivatives. Different codons encoding the same amino acid substitution were tested and showed that the effect was the same, confirming that the effect of increasing malonyl-derived compounds, in this case fatty acid derivatives, was correlated to the amino acid change in BCCP.

Example 2

Modifying Expression of the accBC Operon Increases FAME Production

An expression library of the accBC operon was built and screened for variants that showed improvement over the wild type accBC promoter. Table 2 (supra) depicts a summary of the best variants. The library was built using primers that replaced the native accBC promoter region with a bacteriophage T5 promoter library, which contained degenerate nucleotides to introduce random mutations. The T5 promoter library was joined to appropriate homology regions, using the SOE PCR technique, and the library was integrated into the *E. coli* chromosome as described in Protocol 1, replacing the native *E. coli* accBC promoter. The expression library was screened according to Protocol 2. As can be seen in Table 2 (supra), an increase in titer of up to 315% of normal ACC activity was observed with a variant promoter.

Example 3 accB and accBC Engineering Can Improve the Production of Any Malonyl-CoA Derived Compound The accB mutations (Example 1) and accBC expression changes (Example 2) can be used to increase the titer and yield of any product which is derived from malonyl-CoA. The specific mutations from Example 1 can be introduced into any microbial strain using standard genetic manipulation techniques. The expression of accBC can be modified in any bacterium or yeast according to Example 2 or via other methods known to those in the art, using standard genetic manipulation techniques. The operon structure of accBC is highly conserved and found in many bacteria and other microorganisms. This will allow the same techniques to be used in several different organisms. Compounds derived from malonyl-CoA are numerous and include fatty acids, fatty acid esters (FAME, FAEE, etc.), fatty alcohols, fatty amines, bifunctional fatty acids (hydroxy, diacids), bifunctional fatty alcohols, bifunctional fatty esters, bifunctional fatty amines, beta-hydroxy fatty acid derived compounds, unsaturated fatty acid-derived compounds as well as non-fatty acid based flavanones and flavonoids, polyketides, and 3-hydroxypropionic acid.

As is apparent to one with skill in the art, various modifications and variations of the above aspects and embodiments can be made without departing from the spirit and scope of this disclosure. Such modifications and variations are within the scope of this disclosure.

---

We claim:

1. A variant biotin carboxyl carrier protein (BCCP) comprising a polypeptide sequence selected from the group consisting of SEQ ID NOS: 4, 6, 10, 14, 16, 20, 24, 32, 42, 48, 68 and 70, wherein expression of said variant BCCP confers to a recombinant cell an increased production of a malonyl-CoA-derived compound when compared to a corresponding wild type cell.

2. The variant BCCP of claim 1, wherein said variant BCCP comprises SEQ ID NO: 4 or SEQ ID NO: 6.

3. The variant BCCP of claim 2, wherein said malonyl-CoA-derived compound is FAME.

4. The variant BCCP of claim 1, wherein said malonyl-CoA-derived compound comprises a fatty acid derivative of any one of a fatty acid, a fatty acid methyl ester (FAME), a fatty acid ethyl ester (FAEE), a fatty alcohol, a fatty amine, a beta hydroxy fatty acid derivative, a bifunctional fatty acid derivative, and an unsaturated fatty acid derivative.

5. The variant BCCP of claim 1, wherein said BCCP is encoded by a variant acetyl CoA carboxylase B (accB) gene.

6. The variant BCCP of claim 5, wherein said variant accB gene comprises a nucleic acid sequence selected from the group consisting of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, and 89.

7. A recombinant cell comprising the variant BCCP of claim 1.

8. A method of producing a malonyl-CoA-derived compound, comprising culturing the recombinant cell of claim 7 in a fermentation broth containing a carbon source.

9. The method of claim 8, wherein said malonyl-CoA-derived compound comprises a fatty acid derivative of any one of a fatty acid, a fatty acid methyl ester (FAME), a fatty acid ethyl ester (FAEE), a fatty alcohol, a fatty amine, a beta hydroxy fatty acid derivative, a bifunctional fatty acid derivative, and an unsaturated fatty acid derivative.

10. The method of claim 9, wherein said malonyl-CoA-derived compound is FAME.

11. A method of producing a malonyl-CoA-derived compound, comprising culturing a recombinant cell comprising a variant operon that controls the expression of a variant biotin carboxyl carrier protein (BCCP) wherein the variant BCCP comprises a polypeptide sequence selected from the group consisting of SEQ ID NOS: 4, 6, 10, 14, 16, 20, 24, 32, 42, 48, 68 and 70, and wherein expression of said variant BCCP confers to the recombinant cell an increased production of a malonyl-CoA-derived compound when compared to a corresponding wild type cell.

12. The method of claim 11, wherein said malonyl-CoA-derived compound comprises a fatty acid derivative of any one of a fatty acid, a fatty acid methyl ester (FAME), a fatty acid ethyl ester (FAEE), a fatty alcohol, a fatty amine, a beta hydroxy fatty acid derivative, a bifunctional fatty acid derivative, and an unsaturated fatty acid derivative.

13. The method of claim 12, wherein said malonyl-CoA-derived compound is FAME.

* * * * *

SEQUENCE LISTING

```
<160> NUMBER OF SEQ ID NOS: 109

<210> SEQ ID NO 1
<211> LENGTH: 471
<212> TYPE: DNA
<213> ORGANISM: Escherichia coli

<400> SEQUENCE: 1
atggatattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga aatcagtggt     240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471

<210> SEQ ID NO 2
<211> LENGTH: 156
<212> TYPE: PRT
<213> ORGANISM: Escherichia coli

<400> SEQUENCE: 2

Met Asp Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
                20                  25                  30

Ser Arg Ala Ala Pro Ala Ala Ser Phe Pro Val Met Gln Gln Ala Tyr
            35                  40                  45

Ala Ala Pro Met Met Gln Gln Pro Ala Gln Ser Asn Ala Ala Ala Pro
```

```
            50                  55                  60
Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
             100                 105                 110

Asp Thr Leu Cys Ile Val Glu Ala Met Lys Met Met Asn Gln Ile Glu
         115                 120                 125

Ala Asp Lys Ser Gly Thr Val Lys Ala Ile Leu Val Glu Ser Gly Gln
     130                 135                 140

Pro Val Glu Phe Asp Glu Pro Leu Val Val Ile Glu
145                 150                 155
```

<210> SEQ ID NO 3
<211> LENGTH: 471
<212> TYPE: DNA
<213> ORGANISM: Escherichia coli

<400> SEQUENCE: 3

```
atgcacattc gtaagattaa aaactgatc gagctggttg aagaatcagg catctccgaa      60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga atcagtggt     240
cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 4
<211> LENGTH: 156
<212> TYPE: PRT
<213> ORGANISM: Escherichia coli

<400> SEQUENCE: 4

```
Met His Ile Arg Lys Ile Lys Lys Leu Ile Glu Leu Val Glu Glu Ser
 1                   5                  10                  15

Gly Ile Ser Glu Leu Glu Ile Ser Glu Gly Glu Glu Ser Val Arg Ile
                 20                  25                  30

Ser Arg Ala Ala Pro Ala Ala Ser Phe Pro Val Met Gln Gln Ala Tyr
             35                  40                  45

Ala Ala Pro Met Met Gln Gln Pro Ala Gln Ser Asn Ala Ala Ala Pro
 50                  55                  60

Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
             100                 105                 110

Asp Thr Leu Cys Ile Val Glu Ala Met Lys Met Met Asn Gln Ile Glu
         115                 120                 125

Ala Asp Lys Ser Gly Thr Val Lys Ala Ile Leu Val Glu Ser Gly Gln
     130                 135                 140
```

```
Pro Val Glu Phe Asp Glu Pro Leu Val Val Ile Glu
145                 150                 155
```

```
<210> SEQ ID NO 5
<211> LENGTH: 471
<212> TYPE: DNA
<213> ORGANISM: Escherichia coli

<400> SEQUENCE: 5
```

| | | | | |
|---|---|---|---|---|
| atgaacattc gtaagattaa aaaactgatc gagctggttg aagaatcagg catctccgaa | | | | 60 |
| ctggaaattt ctgaaggcga agagtcagta cgcattagcc gtgcagctcc tgccgcaagt | | | | 120 |
| ttccctgtga tgcaacaagc ttacgctgca ccaatgatgc agcagccagc tcaatctaac | | | | 180 |
| gcagccgctc cggcgaccgt tccttccatg gaagcgccag cagcagcgga atcagtggt | | | | 240 |
| cacatcgtac gttccccgat ggttggtact ttctaccgca ccccaagccc ggacgcaaaa | | | | 300 |
| gcgttcatcg aagtgggtca aaagtcaac gtgggcgata ccctgtgcat cgttgaagcc | | | | 360 |
| atgaaaatga tgaaccagat cgaagcggac aaatccggta ccgtgaaagc aattctggtc | | | | 420 |
| gaaagtggac aaccggtaga atttgacgag ccgctggtcg tcatcgagta a | | | | 471 |

```
<210> SEQ ID NO 6
<211> LENGTH: 156
<212> TYPE: PRT
<213> ORGANISM: Escherichia coli

<400> SEQUENCE: 6
```

```
Met Asn Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
                20                  25                  30

Ser Arg Ala Ala Pro Ala Ala Ser Phe Pro Val Met Gln Gln Ala Tyr
            35                  40                  45

Ala Ala Pro Met Met Gln Gln Pro Ala Gln Ser Asn Ala Ala Ala Pro
        50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155
```

```
<210> SEQ ID NO 7
<211> LENGTH: 471
<212> TYPE: DNA
<213> ORGANISM: Escherichia coli

<400> SEQUENCE: 7
```

| | | | | |
|---|---|---|---|---|
| atgcatattc gtaagattaa aaaactgatc gagctggttg aagaatcagg catctccgaa | | | | 60 |
| ctggaaattt ctgaaggcga agagtcagta cgcattagcc gtgcagctcc tgccgcaagt | | | | 120 |
| ttccctgtga tgcaacaagc ttacgctgca ccaatgatgc agcagccagc tcaatctaac | | | | 180 |

```
gcagccgctc cggcgaccgt tccttccatg aagcgccag cagcagcgga atcagtggt    240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a            471
```

<210> SEQ ID NO 8
<211> LENGTH: 156
<212> TYPE: PRT
<213> ORGANISM: Escherichia coli

<400> SEQUENCE: 8

```
Met His Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
                20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155
```

<210> SEQ ID NO 9
<211> LENGTH: 471
<212> TYPE: DNA
<213> ORGANISM: Escherichia coli

<400> SEQUENCE: 9

```
atgattattc gtaagattaa aaaactgatc gagctggttg aagaatcagg catctccgaa    60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg aagcgccag cagcagcgga atcagtggt    240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a            471
```

<210> SEQ ID NO 10
<211> LENGTH: 156
<212> TYPE: PRT
<213> ORGANISM: Escherichia coli

<400> SEQUENCE: 10

Met Ile Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Pro
    50                  55                  60

Ala Thr Val Pro Ser Met Glu Ala Pro Ala Ala Glu Ile Ser Gly
65              70                  75                  80

His Ile Val Arg Ser Pro Met Val Gly Thr Phe Tyr Arg Thr Pro Ser
            85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Asn Gln Ile Glu
    115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 11
<211> LENGTH: 471
<212> TYPE: DNA
<213> ORGANISM: Escherichia coli

<400> SEQUENCE: 11
atgattattc gtaagattaa aaaactgatc gagctggttg aagaatcagg catctccgaa     60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga atcagtggt     240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471

<210> SEQ ID NO 12
<211> LENGTH: 156
<212> TYPE: PRT
<213> ORGANISM: Escherichia coli

<400> SEQUENCE: 12

Met Ile Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Pro
    50                  55                  60

Ala Thr Val Pro Ser Met Glu Ala Pro Ala Ala Glu Ile Ser Gly
65              70                  75                  80

His Ile Val Arg Ser Pro Met Val Gly Thr Phe Tyr Arg Thr Pro Ser

```
                         85                  90                  95
Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155

<210> SEQ ID NO 13
<211> LENGTH: 471
<212> TYPE: DNA
<213> ORGANISM: Escherichia coli

<400> SEQUENCE: 13
atgactattc gtaagattaa aaaactgatc gagctggttg aagaatcagg catctccgaa       60
ctggaaattt ctgaaggcga agagtcagta cgcattagcc gtgcagctcc tgccgcaagt      120
ttccctgtga tgcaacaagc ttacgctgca ccaatgatgc agcagccagc tcaatctaac      180
gcagccgctc cggcgaccgt tccttccatg aagcgccag cagcagcgga atcagtggt       240 cacatcgtac gttccccgat ggttggtact ttctaccgca ccccaagccc ggacgcaaaa      300
gcgttcatcg aagtgggtca gaaagtcaac gtgggcgata ccctgtgcat cgttgaagcc      360
atgaaaatga tgaaccagat cgaagcggac aaatccggta ccgtgaaagc aattctggtc      420
gaaagtggac aaccggtaga atttgacgag ccgctggtcg tcatcgagta a              471

<210> SEQ ID NO 14
<211> LENGTH: 156
<212> TYPE: PRT
<213> ORGANISM: Escherichia coli

<400> SEQUENCE: 14

Met Thr Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155

<210> SEQ ID NO 15
<211> LENGTH: 471
```

<212> TYPE: DNA
<213> ORGANISM: Escherichia coli

<400> SEQUENCE: 15

```
atgtctattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt      240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471
```

<210> SEQ ID NO 16
<211> LENGTH: 156
<212> TYPE: PRT
<213> ORGANISM: Escherichia coli

<400> SEQUENCE: 16

Met Ser Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 17
<211> LENGTH: 471
<212> TYPE: DNA
<213> ORGANISM: Escherichia coli

<400> SEQUENCE: 17

```
atgagcattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt      240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
```

```
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 18
<211> LENGTH: 156
<212> TYPE: PRT
<213> ORGANISM: Escherichia coli

<400> SEQUENCE: 18

```
Met Ser Ile Arg Lys Ile Lys Lys Leu Ile Glu Leu Val Glu Glu Ser
 1               5                  10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155
```

<210> SEQ ID NO 19
<211> LENGTH: 471
<212> TYPE: DNA
<213> ORGANISM: Escherichia coli

<400> SEQUENCE: 19

```
atgcgaattc gtaagattaa aaaactgatc gagctggttg aagaatcagg catctccgaa    60
ctggaaattt ctgaaggcga agagtcagta cgcattagcc gtgcagctcc tgccgcaagt   120
ttccctgtga tgcaacaagc ttacgctgca ccaatgatgc agcagccagc tcaatctaac   180
gcagccgctc cggcgaccgt tccttccatg gaagcgccag cagcagcgga atcagtggt    240 cacatcgtac gttccccgat ggttggtact ttctaccgca ccccaagccc ggacgcaaaa   300
gcgttcatcg aagtgggtca gaaagtcaac gtgggcgata ccctgtgcat cgttgaagcc   360
atgaaaatga tgaaccagat cgaagcggac aaatccggta ccgtgaaagc aattctggtc   420
gaaagtggac aaccggtaga atttgacgag ccgctggtcg tcatcgagta a             471
```

<210> SEQ ID NO 20
<211> LENGTH: 156
<212> TYPE: PRT
<213> ORGANISM: Escherichia coli

<400> SEQUENCE: 20

```
Met Arg Ile Arg Lys Ile Lys Lys Leu Ile Glu Leu Val Glu Glu Ser
 1               5                  10                  15

Gly Ile Ser Glu Leu Glu Ile Ser Glu Gly Glu Glu Ser Val Arg Ile
            20                  25                  30
```

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
 50                  55                  60

Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
                115                 120                 125

Ala Asp Lys Ser Gly Thr Val Lys Ala Ile Leu Val Glu Ser Gly Gln
130                 135                 140

Pro Val Glu Phe Asp Glu Pro Leu Val Val Ile Glu
145                 150                 155

<210> SEQ ID NO 21
<211> LENGTH: 471
<212> TYPE: DNA
<213> ORGANISM: Escherichia coli

<400> SEQUENCE: 21
atgtctattc gtaagattaa aaactgatc gagctggttg aagaatcagg catctccgaa      60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga atcagtggt     240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471

<210> SEQ ID NO 22
<211> LENGTH: 156
<212> TYPE: PRT
<213> ORGANISM: Escherichia coli

<400> SEQUENCE: 22

Met Ser Ile Arg Lys Ile Lys Lys Leu Ile Glu Leu Val Glu Glu Ser
  1               5                  10                  15

Gly Ile Ser Glu Leu Glu Ile Ser Glu Gly Glu Glu Ser Val Arg Ile
                 20                  25                  30

Ser Arg Ala Ala Pro Ala Ala Ser Phe Pro Val Met Gln Gln Ala Tyr
             35                  40                  45

Ala Ala Pro Met Met Gln Gln Pro Ala Gln Ser Asn Ala Ala Ala Pro
 50                  55                  60

Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu

```
        115                 120                 125
Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155
```

<210> SEQ ID NO 23
<211> LENGTH: 471
<212> TYPE: DNA
<213> ORGANISM: Escherichia coli

<400> SEQUENCE: 23

```
atgtatattc gtaagattaa aaaactgatc gagctggttg aagaatcagg catctccgaa    60
ctggaaattt ctgaaggcga agagtcagta cgcattagcc gtgcagctcc tgccgcaagt   120
ttccctgtga tgcaacaagc ttacgctgca ccaatgatgc agcagccagc tcaatctaac   180
gcagccgctc cggcgaccgt tccttccatg gaagcgccag cagcagcgga aatcagtggt   240
cacatcgtac gttccccgat ggttggtact ttctaccgca ccccaagccc ggacgcaaaa   300
gcgttcatcg aagtgggtca gaaagtcaac gtgggcgata ccctgtgcat cgttgaagcc   360
atgaaaatga tgaaccagat cgaagcggac aaatccggta ccgtgaaagc aattctggtc   420
gaaagtggac aaccggtaga atttgacgag ccgctggtcg tcatcgagta a            471
```

<210> SEQ ID NO 24
<211> LENGTH: 156
<212> TYPE: PRT
<213> ORGANISM: Escherichia coli

<400> SEQUENCE: 24

```
Met Tyr Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 25
<211> LENGTH: 471
<212> TYPE: DNA
<213> ORGANISM: Escherichia coli

<400> SEQUENCE: 25

```
atgtcaattc gtaagattaa aaaactgatc gagctggttg aagaatcagg catctccgaa    60
```

```
ctggaaattt ctgaaggcga agagtcagta cgcattagcc gtgcagctcc tgccgcaagt      120
ttccctgtga tgcaacaagc ttacgctgca ccaatgatgc agcagccagc tcaatctaac      180
gcagccgctc cggcgaccgt tccttccatg gaagcgccag cagcagcgga atcagtggt       240 cacatcgtac gttccccgat ggttggtact ttctaccgca ccccaagccc ggacgcaaaa      300
gcgttcatcg aagtgggtca gaaagtcaac gtgggcgata ccctgtgcat cgttgaagcc      360
atgaaaatga tgaaccagat cgaagcggac aaatccggta ccgtgaaagc aattctggtc      420
gaaagtggac aaccggtaga atttgacgag ccgctggtcg tcatcgagta a               471
```

```
<210> SEQ ID NO 26
<211> LENGTH: 156
<212> TYPE: PRT
<213> ORGANISM: Escherichia coli

<400> SEQUENCE: 26

Met Ser Ile Arg Lys Ile Lys Lys Leu Ile Glu Leu Val Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

```
<210> SEQ ID NO 27
<211> LENGTH: 471
<212> TYPE: DNA
<213> ORGANISM: Escherichia coli

<400> SEQUENCE: 27
atgtacattc gtaagattaa aaaactgatc gagctggttg aagaatcagg catctccgaa      60
ctggaaattt ctgaaggcga agagtcagta cgcattagcc gtgcagctcc tgccgcaagt      120
ttccctgtga tgcaacaagc ttacgctgca ccaatgatgc agcagccagc tcaatctaac      180
gcagccgctc cggcgaccgt tccttccatg gaagcgccag cagcagcgga atcagtggt       240 cacatcgtac gttccccgat ggttggtact ttctaccgca ccccaagccc ggacgcaaaa      300
gcgttcatcg aagtgggtca gaaagtcaac gtgggcgata ccctgtgcat cgttgaagcc      360
atgaaaatga tgaaccagat cgaagcggac aaatccggta ccgtgaaagc aattctggtc      420
gaaagtggac aaccggtaga atttgacgag ccgctggtcg tcatcgagta a               471
```

```
<210> SEQ ID NO 28
```

<211> LENGTH: 156
<212> TYPE: PRT
<213> ORGANISM: Escherichia coli

<400> SEQUENCE: 28

Met Tyr Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
            35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 29
<211> LENGTH: 471
<212> TYPE: DNA
<213> ORGANISM: Escherichia coli

<400> SEQUENCE: 29
atgtacattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga aatcagtggt     240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471

<210> SEQ ID NO 30
<211> LENGTH: 156
<212> TYPE: PRT
<213> ORGANISM: Escherichia coli

<400> SEQUENCE: 30

Met Tyr Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
            35                  40                  45

Ala Ala Pro Met Met Gln Gln Pro Ala Gln Ser Asn Ala Ala Ala Pro
    50                  55                  60

```
Ala Thr Val Pro Ser Met Glu Ala Pro Ala Ala Glu Ile Ser Gly
 65                 70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 31
<211> LENGTH: 471
<212> TYPE: DNA
<213> ORGANISM: Escherichia coli

<400> SEQUENCE: 31

```
atgcttattc gtaagattaa aaaactgatc gagctggttg aagaatcagg catctccgaa      60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga atcagtggt     240
cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 32
<211> LENGTH: 156
<212> TYPE: PRT
<213> ORGANISM: Escherichia coli

<400> SEQUENCE: 32

```
Met Leu Ile Arg Lys Ile Lys Lys Leu Ile Glu Leu Val Glu Glu Ser
  1               5                  10                  15

Gly Ile Ser Glu Leu Glu Ile Ser Glu Gly Glu Ser Val Arg Ile
                 20                  25                  30

Ser Arg Ala Ala Pro Ala Ala Ser Phe Pro Val Met Gln Gln Ala Tyr
             35                  40                  45

Ala Ala Pro Met Met Gln Gln Pro Ala Gln Ser Asn Ala Ala Pro
     50                  55                  60

Ala Thr Val Pro Ser Met Glu Ala Pro Ala Ala Glu Ile Ser Gly
 65                 70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 33
<211> LENGTH: 471
<212> TYPE: DNA
<213> ORGANISM: Escherichia coli

<400> SEQUENCE: 33

```
atgcgaattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt      240
cacatcgtac gttccccgat ggttggtact ttctaccgca ccccaagccc ggacgcaaaa     300
gcgttcatcg aagtgggtca aaagtcaac gtgggcgata ccctgtgcat cgttgaagcc      360
atgaaaatga tgaaccagat cgaagcggac aaatccggta ccgtgaaagc aattctggtc     420
gaaagtggac aaccggtaga atttgacgag ccgctggtcg tcatcgagta a               471
```

<210> SEQ ID NO 34
<211> LENGTH: 156
<212> TYPE: PRT
<213> ORGANISM: Escherichia coli

<400> SEQUENCE: 34

```
Met Arg Ile Arg Lys Ile Lys Lys Leu Ile Glu Leu Val Glu Glu Ser
1               5                   10                  15
Gly Ile Ser Glu Leu Glu Ile Ser Glu Gly Glu Ser Val Arg Ile
        20                  25                  30
Ser Arg Ala Ala Pro Ala Ala Ser Phe Pro Val Met Gln Gln Ala Tyr
    35                  40                  45
Ala Ala Pro Met Met Gln Gln Pro Ala Gln Ser Asn Ala Ala Pro
    50                  55                  60
Ala Thr Val Pro Ser Met Glu Ala Pro Ala Ala Glu Ile Ser Gly
65              70                  75                  80
His Ile Val Arg Ser Pro Met Val Gly Thr Phe Tyr Arg Thr Pro Ser
                85                  90                  95
Pro Asp Ala Lys Ala Phe Ile Glu Val Gly Gln Lys Val Asn Val Gly
            100                 105                 110
Asp Thr Leu Cys Ile Val Glu Ala Met Lys Met Met Asn Gln Ile Glu
        115                 120                 125
Ala Asp Lys Ser Gly Thr Val Lys Ala Ile Leu Val Glu Ser Gly Gln
    130                 135                 140
Pro Val Glu Phe Asp Glu Pro Leu Val Val Ile Glu
145                 150                 155
```

<210> SEQ ID NO 35
<211> LENGTH: 471
<212> TYPE: DNA
<213> ORGANISM: Escherichia coli

<400> SEQUENCE: 35

```
atgttgattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt      240
```

```
cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 36
<211> LENGTH: 156
<212> TYPE: PRT
<213> ORGANISM: Escherichia coli

<400> SEQUENCE: 36

```
Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 37
<211> LENGTH: 471
<212> TYPE: DNA
<213> ORGANISM: Escherichia coli

<400> SEQUENCE: 37

```
atgcgaattc gtaagattaa aaaactgatc gagctggttg aagaatcagg catctccgaa     60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga atcagtggt     240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 38
<211> LENGTH: 156
<212> TYPE: PRT
<213> ORGANISM: Escherichia coli

<400> SEQUENCE: 38

```
Met Arg Ile Arg Lys Ile Lys Lys Leu Ile Glu Leu Val Glu Glu Ser
1               5                   10                  15
Gly Ile Ser Glu Leu Glu Ile Ser Glu Gly Glu Glu Ser Val Arg Ile
            20                  25                  30
Ser Arg Ala Ala Pro Ala Ala Ser Phe Pro Val Met Gln Gln Ala Tyr
        35                  40                  45
Ala Ala Pro Met Met Gln Gln Pro Ala Gln Ser Asn Ala Ala Ala Pro
    50                  55                  60
Ala Thr Val Pro Ser Met Glu Ala Pro Ala Ala Glu Ile Ser Gly
65                  70                  75                  80
His Ile Val Arg Ser Pro Met Val Gly Thr Phe Tyr Arg Thr Pro Ser
                85                  90                  95
Pro Asp Ala Lys Ala Phe Ile Glu Val Gly Gln Lys Val Asn Val Gly
                100                 105                 110
Asp Thr Leu Cys Ile Val Glu Ala Met Lys Met Met Asn Gln Ile Glu
                115                 120                 125
Ala Asp Lys Ser Gly Thr Val Lys Ala Ile Leu Val Glu Ser Gly Gln
                130                 135                 140
Pro Val Glu Phe Asp Glu Pro Leu Val Val Ile Glu
145                 150                 155
```

<210> SEQ ID NO 39
<211> LENGTH: 471
<212> TYPE: DNA
<213> ORGANISM: Escherichia coli

<400> SEQUENCE: 39

```
atgacgattc gtaagattaa aaaactgatc gagctggttg aagaatcagg catctccgaa    60
ctggaaattt ctgaaggcga agagtcagta cgcattagcc gtgcagctcc tgccgcaagt   120
ttccctgtga tgcaacaagc ttacgctgca ccaatgatgc agcagccagc tcaatctaac   180
gcagccgctc cggcgaccgt tccttccatg gaagcgccag cagcagcgga atcagtggt   240
cacatcgtac gttccccgat ggttggtact ttctaccgca ccccaagccc ggacgcaaaa   300
gcgttcatcg aagtgggtca gaaagtcaac gtgggcgata ccctgtgcat cgttgaagcc   360
atgaaaatga tgaaccagat cgaagcggac aaatccggta ccgtgaaagc aattctggtc   420
gaaagtggac aaccggtaga atttgacgag ccgctggtcg tcatcgagta a           471
```

<210> SEQ ID NO 40
<211> LENGTH: 156
<212> TYPE: PRT
<213> ORGANISM: Escherichia coli

<400> SEQUENCE: 40

```
Met Thr Ile Arg Lys Ile Lys Lys Leu Ile Glu Leu Val Glu Glu Ser
1               5                   10                  15
Gly Ile Ser Glu Leu Glu Ile Ser Glu Gly Glu Glu Ser Val Arg Ile
            20                  25                  30
Ser Arg Ala Ala Pro Ala Ala Ser Phe Pro Val Met Gln Gln Ala Tyr
        35                  40                  45
Ala Ala Pro Met Met Gln Gln Pro Ala Gln Ser Asn Ala Ala Ala Pro
    50                  55                  60
Ala Thr Val Pro Ser Met Glu Ala Pro Ala Ala Glu Ile Ser Gly
65                  70                  75                  80
His Ile Val Arg Ser Pro Met Val Gly Thr Phe Tyr Arg Thr Pro Ser
                85                  90                  95
```

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155

<210> SEQ ID NO 41
<211> LENGTH: 471
<212> TYPE: DNA
<213> ORGANISM: Escherichia coli

<400> SEQUENCE: 41
atgtatattc gtaagattaa aaaactgatc gagctggttg aagaatcagg catctccgaa      60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga aatcagtggt    240
cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471

<210> SEQ ID NO 42
<211> LENGTH: 156
<212> TYPE: PRT
<213> ORGANISM: Escherichia coli

<400> SEQUENCE: 42

Met Tyr Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155

<210> SEQ ID NO 43
<211> LENGTH: 471
<212> TYPE: DNA

<213> ORGANISM: Escherichia coli

<400> SEQUENCE: 43

```
atgcttattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt     240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471
```

<210> SEQ ID NO 44
<211> LENGTH: 156
<212> TYPE: PRT
<213> ORGANISM: Escherichia coli

<400> SEQUENCE: 44

```
Met Leu Ile Arg Lys Ile Lys Lys Leu Ile Glu Leu Val Glu Glu Ser
1               5                   10                  15
Gly Ile Ser Glu Leu Glu Ile Ser Glu Gly Glu Glu Ser Val Arg Ile
            20                  25                  30
Ser Arg Ala Ala Pro Ala Ala Ser Phe Pro Val Met Gln Gln Ala Tyr
        35                  40                  45
Ala Ala Pro Met Met Gln Gln Pro Ala Gln Ser Asn Ala Ala Ala Pro
    50                  55                  60
Ala Thr Val Pro Ser Met Glu Ala Pro Ala Ala Ala Glu Ile Ser Gly
65                  70                  75                  80
His Ile Val Arg Ser Pro Met Val Gly Thr Phe Tyr Arg Thr Pro Ser
                85                  90                  95
Pro Asp Ala Lys Ala Phe Ile Glu Val Gly Gln Lys Val Asn Val Gly
                100                 105                 110
Asp Thr Leu Cys Ile Val Glu Ala Met Lys Met Met Asn Gln Ile Glu
            115                 120                 125
Ala Asp Lys Ser Gly Thr Val Lys Ala Ile Leu Val Glu Ser Gly Gln
        130                 135                 140
Pro Val Glu Phe Asp Glu Pro Leu Val Val Ile Glu
145                 150                 155
```

<210> SEQ ID NO 45
<211> LENGTH: 471
<212> TYPE: DNA
<213> ORGANISM: Escherichia coli

<400> SEQUENCE: 45

```
atgttaattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt     240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
```
gaaagtggac aaccggtaga atttgacgag ccgctggtcg tcatcgagta a      471

<210> SEQ ID NO 46
<211> LENGTH: 156
<212> TYPE: PRT
<213> ORGANISM: Escherichia coli

<400> SEQUENCE: 46

Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 47
<211> LENGTH: 471
<212> TYPE: DNA
<213> ORGANISM: Escherichia coli

<400> SEQUENCE: 47
atgcagattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga aatcagtggt     240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471

<210> SEQ ID NO 48
<211> LENGTH: 156
<212> TYPE: PRT
<213> ORGANISM: Escherichia coli

<400> SEQUENCE: 48

Met Gln Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
         35                  40                  45

Ala Ala Pro Met Met Gln Gln Pro Ala Gln Ser Asn Ala Ala Ala Pro
 50                  55                  60

Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155

<210> SEQ ID NO 49
<211> LENGTH: 471
<212> TYPE: DNA
<213> ORGANISM: Escherichia coli

<400> SEQUENCE: 49
atgtatattc gtaagattaa aaaactgatc gagctggttg aagaatcagg catctccgaa        60
ctggaaattt ctgaaggcga agagtcagta cgcattagcc gtgcagctcc tgccgcaagt       120
ttccctgtga tgcaacaagc ttacgctgca ccaatgatgc agcagccagc tcaatctaac       180
gcagccgctc cggcgaccgt tccttccatg gaagcgccag cagcagcgga atcagtggt       240 cacatcgtac gttccccgat ggttggtact ttctaccgca ccccaagccc ggacgcaaaa       300
gcgttcatcg aagtgggtca gaaagtcaac gtgggcgata ccctgtgcat cgttgaagcc       360
atgaaaatga tgaaccagat cgaagcggac aaatccggta ccgtgaaagc aattctggtc       420
gaaagtggac aaccggtaga atttgacgag ccgctggtcg tcatcgagta a                471

<210> SEQ ID NO 50
<211> LENGTH: 156
<212> TYPE: PRT
<213> ORGANISM: Escherichia coli

<400> SEQUENCE: 50

Met Tyr Ile Arg Lys Ile Lys Lys Leu Ile Glu Leu Val Glu Glu Ser
 1               5                  10                  15

Gly Ile Ser Glu Leu Glu Ile Ser Glu Gly Glu Glu Ser Val Arg Ile
             20                  25                  30

Ser Arg Ala Ala Pro Ala Ala Ser Phe Pro Val Met Gln Gln Ala Tyr
         35                  40                  45

Ala Ala Pro Met Met Gln Gln Pro Ala Gln Ser Asn Ala Ala Ala Pro
 50                  55                  60

Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155

<210> SEQ ID NO 51
<211> LENGTH: 471
<212> TYPE: DNA
<213> ORGANISM: Escherichia coli

<400> SEQUENCE: 51
atgttaattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt      240 cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471

<210> SEQ ID NO 52
<211> LENGTH: 156
<212> TYPE: PRT
<213> ORGANISM: Escherichia coli

<400> SEQUENCE: 52

Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 53
<211> LENGTH: 471
<212> TYPE: DNA
<213> ORGANISM: Escherichia coli

<400> SEQUENCE: 53
atgttaattc gtaagattaa aaaactgatc gagctggttg aagaatcagg catctccgaa      60

```
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg aagcgccag cagcagcgga atcagtggt     240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 54
<211> LENGTH: 156
<212> TYPE: PRT
<213> ORGANISM: Escherichia coli

<400> SEQUENCE: 54

```
Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Asn Gln Ile Glu
        115                 120                 125

Ala Asp Lys Ser Gly Thr Val Lys Ala Ile Leu Val Glu Ser Gly Gln
130                 135                 140

Pro Val Glu Phe Asp Glu Pro Leu Val Val Ile Glu
145                 150                 155
```

<210> SEQ ID NO 55
<211> LENGTH: 471
<212> TYPE: DNA
<213> ORGANISM: Escherichia coli

<400> SEQUENCE: 55

```
atgttaattc gtaagattaa aaaactgatc gagctggttg aagaatcagg catctccgaa     60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg aagcgccag cagcagcgga atcagtggt     240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 56
<211> LENGTH: 156

<212> TYPE: PRT
<213> ORGANISM: Escherichia coli

<400> SEQUENCE: 56

```
Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Asn Gln Ile Glu
            115                 120                 125

Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155
```

<210> SEQ ID NO 57
<211> LENGTH: 471
<212> TYPE: DNA
<213> ORGANISM: Escherichia coli

<400> SEQUENCE: 57

```
atgttaattc gtaagattaa aaaactgatc gagctggttg aagaatcagg catctccgaa      60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga aatcagtggt    240
cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a              471
```

<210> SEQ ID NO 58
<211> LENGTH: 156
<212> TYPE: PRT
<213> ORGANISM: Escherichia coli

<400> SEQUENCE: 58

```
Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Pro
    50                  55                  60
```

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 59
<211> LENGTH: 471
<212> TYPE: DNA
<213> ORGANISM: Escherichia coli

<400> SEQUENCE: 59
atgttgattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt      240 cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471

<210> SEQ ID NO 60
<211> LENGTH: 156
<212> TYPE: PRT
<213> ORGANISM: Escherichia coli

<400> SEQUENCE: 60

Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 61
<211> LENGTH: 471
<212> TYPE: DNA
<213> ORGANISM: Escherichia coli

<400> SEQUENCE: 61

```
atgttgattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt     240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471
```

<210> SEQ ID NO 62
<211> LENGTH: 156
<212> TYPE: PRT
<213> ORGANISM: Escherichia coli

<400> SEQUENCE: 62

```
Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 63
<211> LENGTH: 471
<212> TYPE: DNA
<213> ORGANISM: Escherichia coli

<400> SEQUENCE: 63

```
atgcttattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt     240
```

-continued

```
cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 64
<211> LENGTH: 156
<212> TYPE: PRT
<213> ORGANISM: Escherichia coli

<400> SEQUENCE: 64

```
Met Leu Ile Arg Lys Ile Lys Lys Leu Ile Glu Leu Val Glu Glu Ser
1               5                  10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 65
<211> LENGTH: 471
<212> TYPE: DNA
<213> ORGANISM: Escherichia coli

<400> SEQUENCE: 65

```
atgatcattc gtaagattaa aaaactgatc gagctggttg aagaatcagg catctccgaa     60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga atcagtggt     240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

<210> SEQ ID NO 66
<211> LENGTH: 156
<212> TYPE: PRT
<213> ORGANISM: Escherichia coli

<400> SEQUENCE: 66

Met Ile Ile Arg Lys Ile Lys Lys Leu Ile Glu Leu Val Glu Glu Ser

```
             1               5                  10                 15
          Gly Ile Ser Glu Leu Glu Ile Ser Glu Gly Glu Glu Ser Val Arg Ile
                         20                 25                 30

Ser Arg Ala Ala Pro Ala Ala Ser Phe Pro Val Met Gln Gln Ala Tyr
                     35                 40                 45

Ala Ala Pro Met Met Gln Gln Pro Ala Gln Ser Asn Ala Ala Ala Pro
                 50                 55                 60

Ala Thr Val Pro Ser Met Glu Ala Pro Ala Ala Glu Ile Ser Gly
          65                 70                 75                 80

His Ile Val Arg Ser Pro Met Val Gly Thr Phe Tyr Arg Thr Pro Ser
                             85                 90                 95

Pro Asp Ala Lys Ala Phe Ile Glu Val Gly Gln Lys Val Asn Val Gly
                         100                105                110

Asp Thr Leu Cys Ile Val Glu Ala Met Lys Met Met Asn Gln Ile Glu
                         115                120                125

Ala Asp Lys Ser Gly Thr Val Lys Ala Ile Leu Val Glu Ser Gly Gln
                     130                135                140

Pro Val Glu Phe Asp Glu Pro Leu Val Val Ile Glu
          145                150                155
```

```
<210> SEQ ID NO 67
<211> LENGTH: 471
<212> TYPE: DNA
<213> ORGANISM: Escherichia coli

<400> SEQUENCE: 67
atgtatattc gtaagattaa aaactgatc gagctggttg aagaatcagg catctccgaa       60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga aatcagtggt    240
cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471
```

```
<210> SEQ ID NO 68
<211> LENGTH: 156
<212> TYPE: PRT
<213> ORGANISM: Escherichia coli

<400> SEQUENCE: 68

Met Tyr Ile Arg Lys Ile Lys Lys Leu Ile Glu Leu Val Glu Glu Ser
          1               5                  10                 15

Gly Ile Ser Glu Leu Glu Ile Ser Glu Gly Glu Glu Ser Val Arg Ile
                         20                 25                 30

Ser Arg Ala Ala Pro Ala Ala Ser Phe Pro Val Met Gln Gln Ala Tyr
                     35                 40                 45

Ala Ala Pro Met Met Gln Gln Pro Ala Gln Ser Asn Ala Ala Ala Pro
                 50                 55                 60

Ala Thr Val Pro Ser Met Glu Ala Pro Ala Ala Ala Glu Ile Ser Gly
          65                 70                 75                 80

His Ile Val Arg Ser Pro Met Val Gly Thr Phe Tyr Arg Thr Pro Ser
                             85                 90                 95
```

```
Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 69
<211> LENGTH: 471
<212> TYPE: DNA
<213> ORGANISM: Escherichia coli

<400> SEQUENCE: 69

```
atggaaattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg aagcgccag cagcagcgga atcagtggt      240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471
```

<210> SEQ ID NO 70
<211> LENGTH: 156
<212> TYPE: PRT
<213> ORGANISM: Escherichia coli

<400> SEQUENCE: 70

```
Met Glu Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 71
<211> LENGTH: 471
<212> TYPE: DNA
<213> ORGANISM: Escherichia coli

<400> SEQUENCE: 71

```
atgctcattc gtaagattaa aaaactgatc gagctggttg aagaatcagg catctccgaa    60
ctggaaattt ctgaaggcga agagtcagta cgcattagcc gtgcagctcc tgccgcaagt   120
ttccctgtga tgcaacaagc ttacgctgca ccaatgatgc agcagccagc tcaatctaac   180
gcagccgctc cggcgaccgt tccttccatg gaagcgccag cagcagcgga atcagtggt    240
cacatcgtac gttccccgat ggttggtact ttctaccgca ccccaagccc ggacgcaaaa   300
gcgttcatcg aagtgggtca gaaagtcaac gtgggcgata ccctgtgcat cgttgaagcc   360
atgaaaatga tgaaccagat cgaagcggac aaatccggta ccgtgaaagc aattctggtc   420
gaaagtggac aaccggtaga atttgacgag ccgctggtcg tcatcgagta a            471
```

<210> SEQ ID NO 72
<211> LENGTH: 156
<212> TYPE: PRT
<213> ORGANISM: Escherichia coli

<400> SEQUENCE: 72

```
Met Leu Ile Arg Lys Ile Lys Lys Leu Ile Glu Leu Val Glu Glu Ser
1               5                   10                  15
Gly Ile Ser Glu Leu Glu Ile Ser Glu Gly Glu Glu Ser Val Arg Ile
            20                  25                  30
Ser Arg Ala Ala Pro Ala Ala Ser Phe Pro Val Met Gln Gln Ala Tyr
        35                  40                  45
Ala Ala Pro Met Met Gln Gln Pro Ala Gln Ser Asn Ala Ala Ala Pro
    50                  55                  60
Ala Thr Val Pro Ser Met Glu Ala Pro Ala Ala Ala Glu Ile Ser Gly
65                  70                  75                  80
His Ile Val Arg Ser Pro Met Val Gly Thr Phe Tyr Arg Thr Pro Ser
                85                  90                  95
Pro Asp Ala Lys Ala Phe Ile Glu Val Gly Gln Lys Val Asn Val Gly
            100                 105                 110
Asp Thr Leu Cys Ile Val Glu Ala Met Lys Met Met Asn Gln Ile Glu
        115                 120                 125
Ala Asp Lys Ser Gly Thr Val Lys Ala Ile Leu Val Glu Ser Gly Gln
    130                 135                 140
Pro Val Glu Phe Asp Glu Pro Leu Val Val Ile Glu
145                 150                 155
```

<210> SEQ ID NO 73
<211> LENGTH: 471
<212> TYPE: DNA
<213> ORGANISM: Escherichia coli

<400> SEQUENCE: 73

```
atgctcattc gtaagattaa aaaactgatc gagctggttg aagaatcagg catctccgaa    60
ctggaaattt ctgaaggcga agagtcagta cgcattagcc gtgcagctcc tgccgcaagt   120
ttccctgtga tgcaacaagc ttacgctgca ccaatgatgc agcagccagc tcaatctaac   180
gcagccgctc cggcgaccgt tccttccatg gaagcgccag cagcagcgga atcagtggt    240
cacatcgtac gttccccgat ggttggtact ttctaccgca ccccaagccc ggacgcaaaa   300
gcgttcatcg aagtgggtca gaaagtcaac gtgggcgata ccctgtgcat cgttgaagcc   360
atgaaaatga tgaaccagat cgaagcggac aaatccggta ccgtgaaagc aattctggtc   420
```

```
gaaagtggac aaccggtaga atttgacgag ccgctggtcg tcatcgagta a      471
```

<210> SEQ ID NO 74
<211> LENGTH: 156
<212> TYPE: PRT
<213> ORGANISM: Escherichia coli

<400> SEQUENCE: 74

```
Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
            35                  40                  45

Ala Ala Pro Met Met Gln Gln Pro Ala Gln Ser Asn Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
            115                 120                 125

Ala Asp Lys Ser Gly Thr Val Lys Ala Ile Leu Val Glu Ser Gly Gln
    130                 135                 140

Pro Val Glu Phe Asp Pro Leu Val Val Ile Glu
145                 150                 155
```

<210> SEQ ID NO 75
<211> LENGTH: 471
<212> TYPE: DNA
<213> ORGANISM: Escherichia coli

<400> SEQUENCE: 75

```
atgctcattc gtaagattaa aaaactgatc gagctggttg aagaatcagg catctccgaa    60
ctggaaattt ctgaaggcga agagtcagta cgcattagcc gtgcagctcc tgccgcaagt   120
ttccctgtga tgcaacaagc ttacgctgca ccaatgatgc agcagccagc tcaatctaac   180
gcagccgctc cggcgaccgt tccttccatg gaagcgccag cagcagcgga atcagtggt    240
cacatcgtac gttccccgat ggttggtact ttctaccgca ccccaagccc ggacgcaaaa   300
gcgttcatcg aagtgggtca gaaagtcaac gtgggcgata ccctgtgcat cgttgaagcc   360
atgaaaatga tgaaccagat cgaagcggac aaatccggta ccgtgaaagc aattctggtc   420
gaaagtggac aaccggtaga atttgacgag ccgctggtcg tcatcgagta a            471
```

<210> SEQ ID NO 76
<211> LENGTH: 156
<212> TYPE: PRT
<213> ORGANISM: Escherichia coli

<400> SEQUENCE: 76

```
Met Leu Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
```

```
                35                  40                  45
Ala Ala Pro Met Met Gln Gln Pro Ala Gln Ser Asn Ala Ala Pro
         50                  55                  60

Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
             100                 105                 110

Asp Thr Leu Cys Ile Val Glu Ala Met Lys Met Met Asn Gln Ile Glu
             115                 120                 125

Ala Asp Lys Ser Gly Thr Val Lys Ala Ile Leu Val Glu Ser Gly Gln
         130                 135                 140

Pro Val Glu Phe Asp Glu Pro Leu Val Val Ile Glu
145                 150                 155

<210> SEQ ID NO 77
<211> LENGTH: 471
<212> TYPE: DNA
<213> ORGANISM: Escherichia coli

<400> SEQUENCE: 77
atgatcattc gtaagattaa aaaactgatc gagctggttg aagaatcagg catctccgaa     60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga aatcagtggt    240
cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471

<210> SEQ ID NO 78
<211> LENGTH: 156
<212> TYPE: PRT
<213> ORGANISM: Escherichia coli

<400> SEQUENCE: 78

Met Ile Ile Arg Lys Ile Lys Lys Leu Ile Glu Leu Val Glu Glu Ser
  1               5                  10                  15

Gly Ile Ser Glu Leu Glu Ile Ser Glu Gly Glu Glu Ser Val Arg Ile
                 20                  25                  30

Ser Arg Ala Ala Pro Ala Ala Ser Phe Pro Val Met Gln Gln Ala Tyr
             35                  40                  45

Ala Ala Pro Met Met Gln Gln Pro Ala Gln Ser Asn Ala Ala Pro
         50                  55                  60

Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                 85                  90                  95

Pro Asp Ala Lys Ala Phe Ile Glu Val Gly Gln Lys Val Asn Val Gly
             100                 105                 110

Asp Thr Leu Cys Ile Val Glu Ala Met Lys Met Met Asn Gln Ile Glu
             115                 120                 125
```

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 79
<211> LENGTH: 471
<212> TYPE: DNA
<213> ORGANISM: Escherichia coli

<400> SEQUENCE: 79
atggaaattc gtaagattaa aaaactgatc gagctggttg aagaatcagg catctccgaa      60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg aagcgccag cagcagcgga atcagtggt     240 cacatcgtac gttccccgat ggttggtact ttctaccgca ccccaagccc ggacgcaaaa    300
gcgttcatcg aagtgggtca aaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471

<210> SEQ ID NO 80
<211> LENGTH: 156
<212> TYPE: PRT
<213> ORGANISM: Escherichia coli

<400> SEQUENCE: 80

Met Glu Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 81
<211> LENGTH: 471
<212> TYPE: DNA
<213> ORGANISM: Escherichia coli

<400> SEQUENCE: 81
atgtcgattc gtaagattaa aaaactgatc gagctggttg aagaatcagg catctccgaa      60
ctggaaattt ctgaaggcga agagtcagta cgcattagcc gtgcagctcc tgccgcaagt    120

```
ttccctgtga tgcaacaagc ttacgctgca ccaatgatgc agcagccagc tcaatctaac      180
gcagccgctc cggcgaccgt tccttccatg gaagcgccag cagcagcgga atcagtggt       240 cacatcgtac gttccccgat ggttggtact ttctaccgca ccccaagccc ggacgcaaaa      300
gcgttcatcg aagtgggtca gaaagtcaac gtgggcgata ccctgtgcat cgttgaagcc      360
atgaaaatga tgaaccagat cgaagcggac aaatccggta ccgtgaaagc aattctggtc      420
gaaagtggac aaccggtaga atttgacgag ccgctggtcg tcatcgagta a               471
```

<210> SEQ ID NO 82
<211> LENGTH: 156
<212> TYPE: PRT
<213> ORGANISM: Escherichia coli

<400> SEQUENCE: 82

```
Met Ser Ile Arg Lys Ile Lys Lys Leu Ile Glu Leu Val Glu Glu Ser
1               5                   10                  15

Gly Ile Ser Glu Leu Glu Ile Ser Glu Gly Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 83
<211> LENGTH: 471
<212> TYPE: DNA
<213> ORGANISM: Escherichia coli

<400> SEQUENCE: 83

```
atgtcgattc gtaagattaa aaaactgatc gagctggttg aagaatcagg catctccgaa       60
ctggaaattt ctgaaggcga agagtcagta cgcattagcc gtgcagctcc tgccgcaagt      120
ttccctgtga tgcaacaagc ttacgctgca ccaatgatgc agcagccagc tcaatctaac      180
gcagccgctc cggcgaccgt tccttccatg gaagcgccag cagcagcgga atcagtggt       240 cacatcgtac gttccccgat ggttggtact ttctaccgca ccccaagccc ggacgcaaaa      300
gcgttcatcg aagtgggtca gaaagtcaac gtgggcgata ccctgtgcat cgttgaagcc      360
atgaaaatga tgaaccagat cgaagcggac aaatccggta ccgtgaaagc aattctggtc      420
gaaagtggac aaccggtaga atttgacgag ccgctggtcg tcatcgagta a               471
```

<210> SEQ ID NO 84
<211> LENGTH: 156
<212> TYPE: PRT

<213> ORGANISM: Escherichia coli

<400> SEQUENCE: 84

Met Ser Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 85
<211> LENGTH: 471
<212> TYPE: DNA
<213> ORGANISM: Escherichia coli

<400> SEQUENCE: 85
atgtcgattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt      240 cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471

<210> SEQ ID NO 86
<211> LENGTH: 156
<212> TYPE: PRT
<213> ORGANISM: Escherichia coli

<400> SEQUENCE: 86

Met Ser Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly

```
                65                  70                  75                  80
His Ile Val Arg Ser Pro Met Val Gly Thr Phe Tyr Arg Thr Pro Ser
                    85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
                115                 120                 125

Ala Asp Lys Ser Gly Thr Val Lys Ala Ile Leu Val Glu Ser Gly Gln
            130                 135                 140

Pro Val Glu Phe Asp Glu Pro Leu Val Val Ile Glu
145                 150                 155

<210> SEQ ID NO 87
<211> LENGTH: 471
<212> TYPE: DNA
<213> ORGANISM: Escherichia coli

<400> SEQUENCE: 87
atgtcgattc gtaagattaa aaactgatc gagctggttg aagaatcagg catctccgaa      60
ctggaaattt ctgaaggcga agagtcagta cgcattagcc gtgcagctcc tgccgcaagt    120
ttccctgtga tgcaacaagc ttacgctgca ccaatgatgc agcagccagc tcaatctaac    180
gcagccgctc cggcgaccgt tccttccatg gaagcgccag cagcagcgga atcagtggt     240 cacatcgtac gttccccgat ggttggtact ttctaccgca ccccaagccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a             471

<210> SEQ ID NO 88
<211> LENGTH: 156
<212> TYPE: PRT
<213> ORGANISM: Escherichia coli

<400> SEQUENCE: 88

Met Ser Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
                20                  25                  30

Ser Arg Ala Ala Pro Ala Ala Ser Phe Pro Val Met Gln Gln Ala Tyr
            35                  40                  45

Ala Ala Pro Met Met Gln Gln Pro Ala Gln Ser Asn Ala Ala Ala Pro
        50                  55                  60

Ala Thr Val Pro Ser Met Glu Ala Pro Ala Ala Glu Ile Ser Gly
65                  70                  75                  80

His Ile Val Arg Ser Pro Met Val Gly Thr Phe Tyr Arg Thr Pro Ser
                    85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
                115                 120                 125

Ala Asp Lys Ser Gly Thr Val Lys Ala Ile Leu Val Glu Ser Gly Gln
            130                 135                 140

Pro Val Glu Phe Asp Glu Pro Leu Val Val Ile Glu
145                 150                 155
```

<210> SEQ ID NO 89
<211> LENGTH: 471
<212> TYPE: DNA
<213> ORGANISM: Escherichia coli

<400> SEQUENCE: 89

```
atgtcgattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt      240
cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471
```

<210> SEQ ID NO 90
<211> LENGTH: 156
<212> TYPE: PRT
<213> ORGANISM: Escherichia coli

<400> SEQUENCE: 90

```
Met Ser Ile Arg Lys Ile Lys Lys Leu Ile Glu Leu Val Glu Glu Ser
1               5                  10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155
```

<210> SEQ ID NO 91
<211> LENGTH: 80
<212> TYPE: DNA
<213> ORGANISM: Escherichia coli

<400> SEQUENCE: 91

```
ttgttgcaaa ttacacggtg ttgaaggtta tttacatgtt agctgttgat tatcttccct      60
gataagacca gtatttagct                                                  80
```

<210> SEQ ID NO 92
<211> LENGTH: 52
<212> TYPE: DNA
<213> ORGANISM: Escherichia coli

```
<400> SEQUENCE: 92
aatcataaaa aatttatttg ctttcaggaa aatttttctg tataatagat tc          52

<210> SEQ ID NO 93
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
aatcataaaa aatttatttg ctctcaggaa aatttttctg gataatagat tc          52

<210> SEQ ID NO 94
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
aatcataaaa aatttatctt ctctcaggaa aatttttctg tattatagat tc          52

<210> SEQ ID NO 95
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
aatcataaaa aatttatctg ccttcaggaa aatttttctg tataatagat tc          52

<210> SEQ ID NO 96
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
aatcataaaa aatttatttg ccttcaggaa aatttttctg tatagtagat tc          52

<210> SEQ ID NO 97
<211> LENGTH: 30
<212> TYPE: PRT
<213> ORGANISM: Escherichia coli

<400> SEQUENCE: 97

Gly Gln Lys Val Asn Val Gly Asp Thr Leu Cys Ile Val Glu Ala Met
1               5                   10                  15

Lys Met Met Asn Gln Ile Glu Ala Asp Lys Ser Gly Thr Val
            20                  25                  30

<210> SEQ ID NO 98
<211> LENGTH: 30
<212> TYPE: PRT
```

<213> ORGANISM: Lactobacillus brevis

<400> SEQUENCE: 98

Gly Asp His Val Glu Lys Gly Asp Val Val Cys Val Val Glu Ala Met
1               5                   10                  15

Lys Met Ile Asn Glu Val Lys Ser Asp Leu Thr Gly Thr Leu
            20                  25                  30

<210> SEQ ID NO 99
<211> LENGTH: 30
<212> TYPE: PRT
<213> ORGANISM: Stenotrophomonas maltophilia

<400> SEQUENCE: 99

Gly Gln Gln Val Lys Glu Gly Glu Thr Leu Ala Ile Ile Glu Ala Met
1               5                   10                  15

Lys Met Phe Asn Pro Ile Glu Ala Asp Thr Ser Gly Thr Ile
            20                  25                  30

<210> SEQ ID NO 100
<211> LENGTH: 30
<212> TYPE: PRT
<213> ORGANISM: Pseudomonas putida

<400> SEQUENCE: 100

Gly Gln Ser Val Lys Lys Gly Asp Thr Leu Cys Ile Val Glu Ala Met
1               5                   10                  15

Lys Met Met Asn His Ile Glu Ala Asp Ile Gly Gly Val Ile
            20                  25                  30

<210> SEQ ID NO 101
<211> LENGTH: 30
<212> TYPE: PRT
<213> ORGANISM: Bacillus subtilis

<400> SEQUENCE: 101

Gly Ser Lys Val Asn Glu Asn Thr Val Val Cys Ile Val Glu Ala Met
1               5                   10                  15

Lys Leu Phe Asn Glu Ile Glu Ala Glu Val Lys Gly Glu Ile
            20                  25                  30

<210> SEQ ID NO 102
<211> LENGTH: 30
<212> TYPE: PRT
<213> ORGANISM: Corynebacterium glutamicum

<400> SEQUENCE: 102

Gly Ala Glu Val Asn Glu Gly Asp Thr Val Val Val Leu Glu Ala Met
1               5                   10                  15

Lys Met Glu Asn Pro Val Lys Ala His Lys Ser Gly Thr Val
            20                  25                  30

<210> SEQ ID NO 103
<211> LENGTH: 30
<212> TYPE: PRT
<213> ORGANISM: Saccharomyces cerevisiae

<400> SEQUENCE: 103

Gly Glu His Ile Ile Lys Gly Gln Pro Tyr Ala Glu Ile Glu Val Met
1               5                   10                  15

Lys Met Gln Met Pro Leu Val Ser Gln Glu Asn Gly Ile Val
            20                  25                  30

<210> SEQ ID NO 104
<211> LENGTH: 141
<212> TYPE: PRT
<213> ORGANISM: Lactobacillus brevis

<400> SEQUENCE: 104

Met Lys Asn Glu Asp Ile Glu His Leu Leu Glu Lys Phe Asp His Ser
1               5                   10                  15

Ser Leu Lys Asp Phe His Leu Val Gln Asp Asp Phe Gln Leu Ser Leu
            20                  25                  30

Ser Lys Arg Glu Asp Thr Asn Val Pro Thr Pro Ala Thr Ile Asp Gln
        35                  40                  45

Pro Thr Pro Glu Pro Ala Gly Glu Thr Ala Lys Glu Ser Ala Glu Pro
    50                  55                  60

Thr Ile Thr Ala Pro Leu Val Gly Val Val Tyr Leu Ala Pro Ala Pro
65                  70                  75                  80

Glu Lys Pro Val Phe Lys Gln Ile Gly Asp His Val Glu Lys Gly Asp
                85                  90                  95

Val Val Cys Val Val Glu Ala Met Lys Met Ile Asn Glu Val Lys Ser
            100                 105                 110

Asp Leu Thr Gly Thr Leu Thr Lys Val Leu Val Thr Asp Gly Ser Met
        115                 120                 125

Val Glu Tyr Asp Glu Pro Leu Leu Gln Ile Lys Pro Asp
    130                 135                 140

<210> SEQ ID NO 105
<211> LENGTH: 159
<212> TYPE: PRT
<213> ORGANISM: Stenotrophomonas maltophilia

<400> SEQUENCE: 105

Met Asp Leu Arg Lys Ile Lys Lys Leu Ile Asp Leu Leu Glu Glu Ser
1               5                   10                  15

Asn Leu Ala Glu Ile Glu Ile Lys Glu Gly Glu Glu Ser Val Arg Leu
            20                  25                  30

Ser Arg Ala Pro Val Ala Gly Tyr Ala Ala Pro Val Ala Ala Pro Val
        35                  40                  45

Tyr Ala Ala Pro Ala Ala Pro Ala Pro Gln Ala Met Pro Met Gln Ser
    50                  55                  60

Pro Thr Glu Ala Ser Thr Gly Gly Thr Ala Lys Pro Gly Pro Ala Leu
65                  70                  75                  80

Pro Glu Gly His Val Leu Arg Ser Pro Met Val Gly Thr Phe Tyr Ala
                85                  90                  95

Ser Ser Ala Pro Asp Lys Pro Ala Phe Val Thr Val Gly Gln Gln Val
            100                 105                 110

Lys Glu Gly Glu Thr Leu Ala Ile Ile Glu Ala Met Lys Met Phe Asn
        115                 120                 125

Pro Ile Glu Ala Asp Thr Ser Gly Thr Ile Val Ala Ile Leu Gly Glu
    130                 135                 140

Asn Gly Gln Pro Val Glu Phe Asp Gln Pro Leu Phe Val Ile Gly
145                 150                 155

<210> SEQ ID NO 106
<211> LENGTH: 153
<212> TYPE: PRT
<213> ORGANISM: Pseudomonas putida

<400> SEQUENCE: 106

Met Asp Ile Arg Lys Val Lys Lys Leu Ile Glu Leu Leu Glu Glu Ser
1               5                   10                  15

Gly Ile Asp Glu Leu Glu Ile Lys Glu Gly Glu Glu Ser Val Arg Ile
            20                  25                  30

Ser Arg His Ser Lys Thr Pro Ala Ala Gln Gln Phe Tyr Ala Pro Ala
        35                  40                  45

Pro Met Ala Ala Ala Pro Ala Ala Pro Val Ala Ala Ala Ala Pro
    50                  55                  60

Ala Ala Glu Ala Thr Ala Ala Pro Ala Leu Lys Gly Thr Val Val
65                  70                  75                  80

Arg Ser Pro Met Val Gly Thr Phe Tyr Arg Lys Pro Ser Pro Thr Ser
                85                  90                  95

Pro Asn Phe Ala Glu Val Gly Gln Ser Val Lys Lys Gly Asp Thr Leu
            100                 105                 110

Cys Ile Val Glu Ala Met Lys Met Met Asn His Ile Glu Ala Asp Ile
            115                 120                 125

Gly Gly Val Ile Asp Ala Ile Leu Val Glu Asp Gly Gln Pro Val Glu
130                 135                 140

Phe Asp Gln Pro Leu Phe Thr Ile Val
145                 150

<210> SEQ ID NO 107
<211> LENGTH: 159
<212> TYPE: PRT
<213> ORGANISM: Bacillus subtilis

<400> SEQUENCE: 107

Met Leu Asn Ile Lys Glu Ile His Glu Leu Ile Lys Ala Ile Asp Glu
1               5                   10                  15

Ser Thr Ile Asp Glu Phe Val Tyr Glu Asn Glu Gly Val Ser Leu Lys
            20                  25                  30

Leu Lys Lys His Glu Ala Gly Thr Val Gln Val Met Gln Gln Ala Pro
        35                  40                  45

Ala Ala Pro Val Gln Ala Gln Ala Pro Gln Ala Val Gln Pro Gln Ala
    50                  55                  60

Gln Gln Ala Ala Pro Ala Gln Glu Ala Pro Lys Gln Asp Glu Asn
65                  70                  75                  80

Leu His Lys Ile Thr Ser Pro Met Val Gly Thr Phe Tyr Ala Ser Ser
                85                  90                  95

Ser Pro Glu Ala Gly Pro Tyr Val Thr Ala Gly Ser Lys Val Asn Glu
            100                 105                 110

Asn Thr Val Val Cys Ile Val Glu Ala Met Lys Leu Phe Asn Glu Ile
            115                 120                 125

Glu Ala Glu Val Lys Gly Glu Ile Val Glu Val Leu Val Glu Asn Gly
        130                 135                 140

Gln Leu Val Glu Tyr Gly Gln Pro Leu Phe Leu Val Lys Ala Glu
145                 150                 155

<210> SEQ ID NO 108
<211> LENGTH: 591
<212> TYPE: PRT
<213> ORGANISM: Corynebacterium glutamicum

<400> SEQUENCE: 108

```
Met Ser Val Glu Thr Arg Lys Ile Thr Lys Val Leu Val Ala Asn Arg
1               5                   10                  15

Gly Glu Ile Ala Ile Arg Val Phe Arg Ala Ala Arg Asp Glu Gly Ile
                20                  25                  30

Gly Ser Val Ala Val Tyr Ala Glu Pro Asp Ala Asp Ala Pro Phe Val
            35                  40                  45

Ser Tyr Ala Asp Glu Ala Phe Ala Leu Gly Gly Gln Thr Ser Ala Glu
        50                  55                  60

Ser Tyr Leu Val Ile Asp Lys Ile Ile Asp Ala Ala Arg Lys Ser Gly
65                  70                  75                  80

Ala Asp Ala Ile His Pro Gly Tyr Gly Phe Leu Ala Glu Asn Ala Asp
                85                  90                  95

Phe Ala Glu Ala Val Ile Asn Glu Gly Leu Ile Trp Ile Gly Pro Ser
                100                 105                 110

Pro Glu Ser Ile Arg Ser Leu Gly Asp Lys Val Thr Ala Arg His Ile
            115                 120                 125

Ala Asp Thr Ala Lys Ala Pro Met Ala Pro Gly Thr Lys Glu Pro Val
    130                 135                 140

Lys Asp Ala Ala Glu Val Val Ala Phe Ala Glu Glu Phe Gly Leu Pro
145                 150                 155                 160

Ile Ala Ile Lys Ala Ala Phe Gly Gly Gly Gly Arg Gly Met Lys Val
                165                 170                 175

Ala Tyr Lys Met Glu Glu Val Ala Asp Leu Phe Glu Ser Ala Thr Arg
            180                 185                 190

Glu Ala Thr Ala Ala Phe Gly Arg Gly Glu Cys Phe Val Glu Arg Tyr
        195                 200                 205

Leu Asp Lys Ala Arg His Val Glu Ala Gln Val Ile Ala Asp Lys His
    210                 215                 220

Gly Asn Val Val Ala Gly Thr Arg Asp Cys Ser Leu Gln Arg Arg
225                 230                 235                 240

Phe Gln Lys Leu Val Glu Glu Ala Pro Ala Pro Phe Leu Thr Asp Asp
                245                 250                 255

Gln Arg Glu Arg Leu His Ser Ser Ala Lys Ala Ile Cys Lys Glu Ala
        260                 265                 270

Gly Tyr Tyr Gly Ala Gly Thr Val Glu Tyr Leu Val Gly Ser Asp Gly
    275                 280                 285

Leu Ile Ser Phe Leu Glu Val Asn Thr Arg Leu Gln Val Glu His Pro
    290                 295                 300

Val Thr Glu Glu Thr Thr Gly Ile Asp Leu Val Arg Glu Met Phe Arg
305                 310                 315                 320

Ile Ala Glu Gly His Glu Leu Ser Ile Lys Glu Asp Pro Ala Pro Arg
                325                 330                 335

Gly His Ala Phe Glu Phe Arg Ile Asn Gly Glu Asp Ala Gly Ser Asn
            340                 345                 350

Phe Met Pro Ala Pro Gly Lys Ile Thr Ser Tyr Arg Glu Pro Gln Gly
        355                 360                 365

Pro Gly Val Arg Met Asp Ser Gly Val Val Glu Gly Ser Glu Ile Ser
    370                 375                 380

Gly Gln Phe Asp Ser Met Leu Ala Lys Leu Ile Val Trp Gly Asp Thr
385                 390                 395                 400

Arg Glu Gln Ala Leu Gln Arg Ser Arg Arg Ala Leu Ala Glu Tyr Val
                405                 410                 415

Val Glu Gly Met Pro Thr Val Ile Pro Phe His Gln His Ile Val Glu
```

```
                420             425             430
Asn Pro Ala Phe Val Gly Asn Asp Glu Gly Phe Glu Ile Tyr Thr Lys
            435                 440                 445
Trp Ile Glu Val Trp Asp Asn Pro Ile Ala Pro Tyr Val Asp Ala
450                 455                 460
Ser Glu Leu Asp Glu Asp Lys Thr Pro Ala Gln Lys Val Val
465                 470                 475                 480
Val Glu Ile Asn Gly Arg Arg Val Glu Val Ala Leu Pro Gly Asp Leu
                485                 490                 495
Ala Leu Gly Gly Thr Ala Gly Pro Lys Lys Ala Lys Lys Arg Arg
            500                 505                 510
Ala Gly Gly Ala Lys Ala Gly Val Ser Gly Asp Ala Val Ala Ala Pro
            515                 520                 525
Met Gln Gly Thr Val Ile Lys Val Asn Val Glu Gly Ala Glu Val
            530                 535                 540
Asn Glu Gly Asp Thr Val Val Leu Glu Ala Met Lys Met Glu Asn
545                 550                 555                 560
Pro Val Lys Ala His Lys Ser Gly Thr Val Thr Gly Leu Thr Val Ala
                565                 570                 575
Ala Gly Glu Gly Val Asn Lys Gly Val Val Leu Leu Glu Ile Lys
            580                 585                 590

<210> SEQ ID NO 109
<211> LENGTH: 2237
<212> TYPE: PRT
<213> ORGANISM: Saccharomyces cerevisiae

<400> SEQUENCE: 109

Met Ser Glu Glu Ser Leu Phe Glu Ser Pro Gln Lys Met Glu Tyr
1               5                   10                  15
Glu Ile Thr Asn Tyr Ser Glu Arg His Thr Glu Leu Pro Gly His Phe
                20                  25                  30
Ile Gly Leu Asn Thr Val Asp Lys Leu Glu Glu Ser Pro Leu Arg Asp
            35                  40                  45
Phe Val Lys Ser His Gly Gly His Thr Val Ile Ser Lys Ile Leu Ile
        50                  55                  60
Ala Asn Asn Gly Ile Ala Ala Val Lys Glu Ile Arg Ser Val Arg Lys
65                  70                  75                  80
Trp Ala Tyr Glu Thr Phe Gly Asp Asp Arg Thr Val Gln Phe Val Ala
                85                  90                  95
Met Ala Thr Pro Glu Asp Leu Glu Ala Asn Ala Glu Tyr Ile Arg Met
            100                 105                 110
Ala Asp Gln Tyr Ile Glu Val Pro Gly Gly Thr Asn Asn Asn Tyr
            115                 120                 125
Ala Asn Val Asp Leu Ile Val Asp Ile Ala Glu Arg Ala Asp Val Asp
        130                 135                 140
Ala Val Trp Ala Gly Trp Gly His Ala Ser Glu Asn Pro Leu Leu Pro
145                 150                 155                 160
Glu Lys Leu Ser Gln Ser Lys Arg Lys Val Ile Phe Ile Gly Pro Pro
                165                 170                 175
Gly Asn Ala Met Arg Ser Leu Gly Asp Lys Ile Ser Ser Thr Ile Val
            180                 185                 190
Ala Gln Ser Ala Lys Val Pro Cys Ile Pro Trp Ser Gly Thr Gly Val
        195                 200                 205
```

-continued

```
Asp Thr Val His Val Asp Glu Lys Thr Gly Leu Val Ser Val Asp Asp
210                 215                 220
Asp Ile Tyr Gln Lys Gly Cys Cys Thr Ser Pro Glu Asp Gly Leu Gln
225                 230                 235                 240
Lys Ala Lys Arg Ile Gly Phe Pro Val Met Ile Lys Ala Ser Glu Gly
                245                 250                 255
Gly Gly Gly Lys Gly Ile Arg Gln Val Glu Arg Glu Glu Asp Phe Ile
                260                 265                 270
Ala Leu Tyr His Gln Ala Ala Asn Glu Ile Pro Gly Ser Pro Ile Phe
                275                 280                 285
Ile Met Lys Leu Ala Gly Arg Ala Arg His Leu Glu Val Gln Leu Leu
290                 295                 300
Ala Asp Gln Tyr Gly Thr Asn Ile Ser Leu Phe Gly Arg Asp Cys Ser
305                 310                 315                 320
Val Gln Arg Arg His Gln Lys Ile Ile Glu Glu Ala Pro Val Thr Ile
                325                 330                 335
Ala Lys Ala Glu Thr Phe His Glu Met Glu Lys Ala Ala Val Arg Leu
                340                 345                 350
Gly Lys Leu Val Gly Tyr Val Ser Ala Gly Thr Val Glu Tyr Leu Tyr
                355                 360                 365
Ser His Asp Asp Gly Lys Phe Tyr Phe Leu Glu Leu Asn Pro Arg Leu
370                 375                 380
Gln Val Glu His Pro Thr Thr Glu Met Val Ser Gly Val Asn Leu Pro
385                 390                 395                 400
Ala Ala Gln Leu Gln Ile Ala Met Gly Ile Pro Met His Arg Ile Ser
                405                 410                 415
Asp Ile Arg Thr Leu Tyr Gly Met Asn Pro His Ser Ala Ser Glu Ile
                420                 425                 430
Asp Phe Glu Phe Lys Thr Gln Asp Ala Thr Lys Lys Gln Arg Arg Pro
                435                 440                 445
Ile Pro Lys Gly His Cys Thr Ala Cys Arg Ile Thr Ser Glu Asp Pro
450                 455                 460
Asn Asp Gly Phe Lys Pro Ser Gly Gly Thr Leu His Glu Leu Asn Phe
465                 470                 475                 480
Arg Ser Ser Asn Val Trp Gly Tyr Phe Ser Val Gly Asn Asn Gly
                485                 490                 495
Asn Ile His Ser Phe Ser Asp Ser Gln Phe Gly His Ile Phe Ala Phe
                500                 505                 510
Gly Glu Asn Arg Gln Ala Ser Arg Lys His Met Val Val Ala Leu Lys
                515                 520                 525
Glu Leu Ser Ile Arg Gly Asp Phe Arg Thr Thr Val Glu Tyr Leu Ile
530                 535                 540
Lys Leu Leu Glu Thr Glu Asp Phe Glu Asp Asn Thr Ile Thr Thr Gly
545                 550                 555                 560
Trp Leu Asp Asp Leu Ile Thr His Lys Met Thr Ala Glu Lys Pro Asp
                565                 570                 575
Pro Thr Leu Ala Val Ile Cys Gly Ala Ala Thr Lys Ala Phe Leu Ala
                580                 585                 590
Ser Glu Glu Ala Arg His Lys Tyr Ile Glu Ser Leu Gln Lys Gly Gln
                595                 600                 605
Val Leu Ser Lys Asp Leu Leu Gln Thr Met Phe Pro Val Asp Phe Ile
610                 615                 620
His Glu Gly Lys Arg Tyr Lys Phe Thr Val Ala Lys Ser Gly Asn Asp
```

```
                625                 630                 635                 640
        Arg Tyr Thr Leu Phe Ile Asn Gly Ser Lys Cys Asp Ile Ile Leu Arg
                        645                 650                 655

Gln Leu Ser Asp Gly Gly Leu Leu Ile Ala Ile Gly Gly Lys Ser His
                        660                 665                 670

Thr Ile Tyr Trp Lys Glu Glu Val Ala Ala Thr Arg Leu Ser Val Asp
                        675                 680                 685

Ser Met Thr Thr Leu Leu Glu Val Glu Asn Asp Pro Thr Gln Leu Arg
                690                 695                 700

Thr Pro Ser Pro Gly Lys Leu Val Lys Phe Leu Val Glu Asn Gly Glu
        705                 710                 715                 720

His Ile Ile Lys Gly Gln Pro Tyr Ala Glu Ile Glu Val Met Lys Met
                        725                 730                 735

Gln Met Pro Leu Val Ser Gln Glu Asn Gly Ile Val Gln Leu Leu Lys
                        740                 745                 750

Gln Pro Gly Ser Thr Ile Val Ala Gly Asp Ile Met Ala Ile Met Thr
                        755                 760                 765

Leu Asp Asp Pro Ser Lys Val Lys His Ala Leu Pro Phe Glu Gly Met
                770                 775                 780

Leu Pro Asp Phe Gly Ser Pro Val Ile Glu Gly Thr Lys Pro Ala Tyr
        785                 790                 795                 800

Lys Phe Lys Ser Leu Val Ser Thr Leu Glu Asn Ile Leu Lys Gly Tyr
                        805                 810                 815

Asp Asn Gln Val Ile Met Asn Ala Ser Leu Gln Gln Leu Ile Glu Val
                        820                 825                 830

Leu Arg Asn Pro Lys Leu Pro Tyr Ser Glu Trp Lys Leu His Ile Ser
                835                 840                 845

Ala Leu His Ser Arg Leu Pro Ala Lys Leu Asp Glu Gln Met Glu Glu
                850                 855                 860

Leu Val Ala Arg Ser Leu Arg Arg Gly Ala Val Phe Pro Ala Arg Gln
        865                 870                 875                 880

Leu Ser Lys Leu Ile Asp Met Ala Val Lys Asn Pro Glu Tyr Asn Pro
                        885                 890                 895

Asp Lys Leu Leu Gly Ala Val Val Glu Pro Leu Ala Asp Ile Ala His
                        900                 905                 910

Lys Tyr Ser Asn Gly Leu Glu Ala His Glu His Ser Ile Phe Val His
                        915                 920                 925

Phe Leu Glu Glu Tyr Tyr Glu Val Glu Lys Leu Phe Asn Gly Pro Asn
                930                 935                 940

Val Arg Glu Glu Asn Ile Ile Leu Lys Leu Arg Asp Glu Asn Pro Lys
        945                 950                 955                 960

Asp Leu Asp Lys Val Ala Leu Thr Val Leu Ser His Ser Lys Val Ser
                        965                 970                 975

Ala Lys Asn Asn Leu Ile Leu Ala Ile Leu Lys His Tyr Gln Pro Leu
                        980                 985                 990

Cys Lys Leu Ser Ser Lys Val Ser  Ala Ile Phe Ser Thr  Pro Leu Gln
                        995                 1000                1005

His Ile  Val Glu Leu Glu Ser  Lys Ala Thr Ala Lys  Val Ala Leu
                1010                1015                1020

Gln Ala  Arg Glu Ile Leu Ile  Gln Gly Ala Leu Pro  Ser Val Lys
                1025                1030                1035

Glu Arg  Thr Glu Gln Ile Glu  His Ile Leu Lys Ser  Ser Val Val
                1040                1045                1050
```

```
Lys Val Ala Tyr Gly Ser Ser Asn Pro Lys Arg Ser Glu Pro Asp
1055                1060                1065

Leu Asn Ile Leu Lys Asp Leu Ile Asp Ser Asn Tyr Val Val Phe
1070                1075                1080

Asp Val Leu Leu Gln Phe Leu Thr His Gln Asp Pro Val Val Thr
1085                1090                1095

Ala Ala Ala Ala Gln Val Tyr Ile Arg Arg Ala Tyr Arg Ala Tyr
1100                1105                1110

Thr Ile Gly Asp Ile Arg Val His Glu Gly Val Thr Val Pro Ile
1115                1120                1125

Val Glu Trp Lys Phe Gln Leu Pro Ser Ala Ala Phe Ser Thr Phe
1130                1135                1140

Pro Thr Val Lys Ser Lys Met Gly Met Asn Arg Ala Val Ser Val
1145                1150                1155

Ser Asp Leu Ser Tyr Val Ala Asn Ser Gln Ser Ser Pro Leu Arg
1160                1165                1170

Glu Gly Ile Leu Met Ala Val Asp His Leu Asp Asp Val Asp Glu
1175                1180                1185

Ile Leu Ser Gln Ser Leu Glu Val Ile Pro Arg His Gln Ser Ser
1190                1195                1200

Ser Asn Gly Pro Ala Pro Asp Arg Ser Gly Ser Ser Ala Ser Leu
1205                1210                1215

Ser Asn Val Ala Asn Val Cys Val Ala Ser Thr Glu Gly Phe Glu
1220                1225                1230

Ser Glu Glu Glu Ile Leu Val Arg Leu Arg Glu Ile Leu Asp Leu
1235                1240                1245

Asn Lys Gln Glu Leu Ile Asn Ala Ser Ile Arg Arg Ile Thr Phe
1250                1255                1260

Met Phe Gly Phe Lys Asp Gly Ser Tyr Pro Lys Tyr Tyr Thr Phe
1265                1270                1275

Asn Gly Pro Asn Tyr Asn Glu Asn Glu Thr Ile Arg His Ile Glu
1280                1285                1290

Pro Ala Leu Ala Phe Gln Leu Glu Leu Gly Arg Leu Ser Asn Phe
1295                1300                1305

Asn Ile Lys Pro Ile Phe Thr Asp Asn Arg Asn Ile His Val Tyr
1310                1315                1320

Glu Ala Val Ser Lys Thr Ser Pro Leu Asp Lys Arg Phe Phe Thr
1325                1330                1335

Arg Gly Ile Ile Arg Thr Gly His Ile Arg Asp Asp Ile Ser Ile
1340                1345                1350

Gln Glu Tyr Leu Thr Ser Glu Ala Asn Arg Leu Met Ser Asp Ile
1355                1360                1365

Leu Asp Asn Leu Glu Val Thr Asp Thr Ser Asn Ser Asp Leu Asn
1370                1375                1380

His Ile Phe Ile Asn Phe Ile Ala Val Phe Asp Ile Ser Pro Glu
1385                1390                1395

Asp Val Glu Ala Ala Phe Gly Gly Phe Leu Glu Arg Phe Gly Lys
1400                1405                1410

Arg Leu Leu Arg Leu Arg Val Ser Ser Ala Glu Ile Arg Ile Ile
1415                1420                1425

Ile Lys Asp Pro Gln Thr Gly Ala Pro Val Pro Leu Arg Ala Leu
1430                1435                1440
```

```
Ile Asn Asn Val Ser Gly Tyr Val Ile Lys Thr Glu Met Tyr Thr
1445                1450                1455

Glu Val Lys Asn Ala Lys Gly Glu Trp Val Phe Lys Ser Leu Gly
1460                1465                1470

Lys Pro Gly Ser Met His Leu Arg Pro Ile Ala Thr Pro Tyr Pro
1475                1480                1485

Val Lys Glu Trp Leu Gln Pro Lys Arg Tyr Lys Ala His Leu Met
1490                1495                1500

Gly Thr Thr Tyr Val Tyr Asp Phe Pro Glu Leu Phe Arg Gln Ala
1505                1510                1515

Ser Ser Ser Gln Gly Lys Asn Phe Ser Ala Asp Val Lys Leu Thr
1520                1525                1530

Asp Asp Phe Phe Ile Ser Asn Glu Leu Ile Glu Asp Glu Asn Gly
1535                1540                1545

Glu Leu Thr Glu Val Glu Arg Glu Pro Gly Ala Asn Ala Ile Gly
1550                1555                1560

Met Val Ala Phe Lys Ile Thr Val Lys Thr Pro Glu Tyr Pro Arg
1565                1570                1575

Gly Arg Gln Phe Val Val Ala Asn Asp Ile Thr Phe Lys Ile
1580                1585                1590

Gly Ser Phe Gly Pro Gln Glu Asp Glu Phe Phe Asn Lys Val Thr
1595                1600                1605

Glu Tyr Ala Arg Lys Arg Gly Ile Pro Arg Ile Tyr Leu Ala Ala
1610                1615                1620

Asn Ser Gly Ala Arg Ile Gly Met Ala Glu Glu Ile Val Pro Leu
1625                1630                1635

Phe Gln Val Ala Trp Asn Asp Ala Ala Asn Pro Asp Lys Gly Phe
1640                1645                1650

Gln Tyr Leu Tyr Leu Thr Ser Glu Gly Met Glu Thr Leu Lys Lys
1655                1660                1665

Phe Asp Lys Glu Asn Ser Val Leu Thr Glu Arg Thr Val Ile Asn
1670                1675                1680

Gly Glu Glu Arg Phe Val Ile Lys Thr Ile Ile Gly Ser Glu Asp
1685                1690                1695

Gly Leu Gly Val Glu Cys Leu Arg Gly Ser Gly Leu Ile Ala Gly
1700                1705                1710

Ala Thr Ser Arg Ala Tyr His Asp Ile Phe Thr Ile Thr Leu Val
1715                1720                1725

Thr Cys Arg Ser Val Gly Ile Gly Ala Tyr Leu Val Arg Leu Gly
1730                1735                1740

Gln Arg Ala Ile Gln Val Glu Gly Gln Pro Ile Ile Trp Tyr Arg
1745                1750                1755

Cys Leu Leu Thr Gly Ala Pro Glu Ser Thr Asn Ala Gly Arg Glu
1760                1765                1770

Val Tyr Thr Ser Asn Leu Gln Leu Gly Gly Thr Gln Ile Met Tyr
1775                1780                1785

Asn Asn Gly Val Ser His Leu Thr Ala Val Asp Asp Leu Ala Gly
1790                1795                1800

Val Glu Lys Ile Val Glu Trp Met Ser Tyr Val Pro Ala Lys Arg
1805                1810                1815

Asn Met Pro Val Pro Ile Leu Glu Thr Lys Asp Thr Trp Asp Arg
1820                1825                1830

Pro Val Asp Phe Thr Pro Thr Asn Asp Glu Thr Tyr Asp Val Arg
```

-continued

```
          1835                1840               1845

Trp Met Ile Glu Gly Arg Glu Thr Glu Ser Gly Phe Glu Tyr Gly
        1850                1855               1860

Leu Phe Asp Lys Gly Ser Phe Phe Glu Thr Leu Ser Gly Trp Ala
        1865                1870               1875

Lys Gly Val Val Gly Arg Ala Arg Leu Gly Gly Ile Pro Leu
        1880                1885               1890

Gly Val Ile Gly Val Glu Thr Arg Thr Val Glu Asn Leu Ile Pro
        1895                1900               1905

Ala Asp Pro Ala Asn Pro Asn Ser Ala Glu Thr Leu Ile Gln Glu
        1910                1915               1920

Pro Gly Gln Val Trp His Pro Asn Ser Ala Phe Lys Thr Ala Gln
        1925                1930               1935

Ala Ile Asn Asp Phe Asn Asn Gly Glu Gln Leu Pro Met Met Ile
        1940                1945               1950

Leu Ala Asn Trp Arg Gly Phe Ser Gly Gly Gln Arg Asp Met Phe
        1955                1960               1965

Asn Glu Val Leu Lys Tyr Gly Ser Phe Ile Val Asp Ala Leu Val
        1970                1975               1980

Asp Tyr Lys Gln Pro Ile Ile Ile Tyr Ile Pro Pro Thr Gly Glu
        1985                1990               1995

Leu Arg Gly Gly Ser Trp Val Val Asp Pro Thr Ile Asn Ala
        2000                2005               2010

Asp Gln Met Glu Met Tyr Ala Asp Val Asn Ala Arg Ala Gly Val
        2015                2020               2025

Leu Glu Pro Gln Gly Met Val Gly Ile Lys Phe Arg Arg Glu Lys
        2030                2035               2040

Leu Leu Asp Thr Met Asn Arg Leu Asp Asp Lys Tyr Arg Glu Leu
        2045                2050               2055

Arg Ser Gln Leu Ser Asn Lys Ser Leu Ala Pro Glu Val His Gln
        2060                2065               2070

Gln Ile Ser Lys Gln Leu Ala Asp Arg Glu Arg Glu Leu Leu Pro
        2075                2080               2085

Ile Tyr Gly Gln Ile Ser Leu Gln Phe Ala Asp Leu His Asp Arg
        2090                2095               2100

Ser Ser Arg Met Val Ala Lys Gly Val Ile Ser Lys Glu Leu Glu
        2105                2110               2115

Trp Thr Glu Ala Arg Arg Phe Phe Phe Trp Arg Leu Arg Arg Arg
        2120                2125               2130

Leu Asn Glu Glu Tyr Leu Ile Lys Arg Leu Ser His Gln Val Gly
        2135                2140               2145

Glu Ala Ser Arg Leu Glu Lys Ile Ala Arg Ile Arg Ser Trp Tyr
        2150                2155               2160

Pro Ala Ser Val Asp His Glu Asp Asp Arg Gln Val Ala Thr Trp
        2165                2170               2175

Ile Glu Glu Asn Tyr Lys Thr Leu Asp Asp Lys Leu Lys Gly Leu
        2180                2185               2190

Lys Leu Glu Ser Phe Ala Gln Asp Leu Ala Lys Lys Ile Arg Ser
        2195                2200               2205
```

```
Asp His Asp Asn Ala Ile Asp     Gly Leu Ser Glu Val     Ile Lys Met
    2210                2215                    2220

Leu Ser Thr Asp Asp Lys Glu     Lys Leu Leu Lys Thr     Leu Lys
    2225                2230                    2235
```